United States Patent
Wu et al.

(10) Patent No.: US 7,265,122 B2
(45) Date of Patent: Sep. 4, 2007

(54) PYRIDINE, PYRIMIDINE, QUINOLINE, QUINAZOLINE, AND NAPHTHALENE UROTENSIN-II RECEPTOR ANTAGONISTS

(75) Inventors: Chengde Wu, Pearland, TX (US); C. Eric Anderson, Houston, TX (US); Huong Bui, Pearland, TX (US); Brian Dupre, Houston, TX (US); Daxin Gao, Houston, TX (US); George W. Holland, Houston, TX (US); Jamal Kassir, Stafford, TX (US); Wen Li, Santa Clara, CA (US); Junmei Wang, Austin, TX (US)

(73) Assignee: Encysive Pharmaceuticals, Inc., Houston, TX (US)

( * ) Notice: Subject to any disclaimer, the term of this patent is extended or adjusted under 35 U.S.C. 154(b) by 289 days.

(21) Appl. No.: 10/783,916

(22) Filed: Feb. 20, 2004

(65) Prior Publication Data
US 2004/0186102 A1  Sep. 23, 2004

Related U.S. Application Data

(60) Provisional application No. 60/451,089, filed on Feb. 28, 2003.

(51) Int. Cl.
*C07D 401/02* (2006.01)
*A61K 31/47* (2006.01)

(52) U.S. Cl. .............. 514/256; 514/313; 514/352; 544/242; 546/159; 546/304

(58) Field of Classification Search .......... 546/159, 546/304; 544/242; 514/256, 313, 352, 353
See application file for complete search history.

(56) References Cited

U.S. PATENT DOCUMENTS

3,978,055 A * 8/1976 Fauran et al. .......... 544/122

FOREIGN PATENT DOCUMENTS

| FR | 1503443 | | 12/1966 |
|---|---|---|---|
| WO | WO 00/006254 | * | 2/2000 |
| WO | WO 02/062787 A1 | | 8/2002 |
| WO | WO 02/089740 A2 | | 11/2002 |
| WO | WO 02/089785 A1 | | 11/2002 |
| WO | WO 02/089792 A1 | | 11/2002 |
| WO | WO 02/089793 A1 | | 11/2002 |
| WO | WO 02/090337 A1 | | 11/2002 |
| WO | WO 02/090348 A1 | | 11/2002 |
| WO | WO 02/090353 A1 | | 11/2002 |
| WO | WO 03/099773 A1 | | 12/2003 |
| WO | WO 2004/026836 A2 | | 4/2004 |

OTHER PUBLICATIONS

Elslager et al, Journal of Medicinal Chemistry, vol. 24, No. 2, pp. 127-140, 1981.*
Apelt et al, Journal of Medicinal Chemistry, vol. 45, No. 5, pp. 1128-1141.*
Cain, Bruce F., Baguley, Bruce C., Denny, William A., "*Potential Antitumor Agents. 28. Deoxyribon Acid Polyintercalating Agents*" J. of Medicinal Chemistry, pp. 658-668; vol. 21, No. 7 (1978).
English Abstract of French Patent FR 1,503,443.

* cited by examiner

*Primary Examiner*—Zinna N. Davis
(74) *Attorney, Agent, or Firm*—Jones Day

(57) ABSTRACT

The present invention relates to urotensin II receptor antagonists, pharmaceutical compositions containing them and their use.

4 Claims, No Drawings

PYRIDINE, PYRIMIDINE, QUINOLINE, QUINAZOLINE, AND NAPHTHALENE UROTENSIN-II RECEPTOR ANTAGONISTS

This application claims priority of provisional U.S. Appl. No. 60/451,089, filed Feb. 28, 2003.

FIELD OF THE INVENTION

The present invention relates to urotensin II receptor antagonists, pharmaceutical compositions containing them and their use.

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis are angiotensin-II, endothelin-1, and norepinephrine, all of which function via an interaction with specific G-protein coupled receptors (GPCR). Urotensin-II, represents an important member of this neurohumoral axis.

In the fish, this peptide has significant hemodynamic and endocrine actions in diverse end-organ systems and tissues:

both vascular and non-vascular (smooth muscle contraction) including smooth muscle preparations from the gastrointestinal tract and genitourinary tract. Both pressor and depressor activity has been described upon systemic administration of exogenous peptide.

osmoregulation effects which include the modulation of transepithelial ion ($Na^+$, $Cl^-$) transport.

Although a diuretic effect has been described, such an effect is postulated to be secondary to direct renovascular effects (elevated GFR); urotensin-II influences prolactic secretion and exhibits a lipolytic effect in fish (activating triacylglycerol lipase resulting in the mobilization of non-esterified free fatty acids) (Person, et al. Proc. Natl. Acad. Sci. (U.S.A.) 1980, 77, 5021; Conlon, et al. J. Exp. Zool. 1996, 275, 226); human urotensin-II has been found to be an extremely potent and efficacious vasoconstrictor; exhibited sustained contractile activity that was extremely resistant to wash out; and had detrimental effects on cardiac performance (myocardial contractility). Human urotensin-II was assessed for contractile activity in the rat-isolated aorta and was shown to be a very potent contractile agonist. Based on the in vitro pharmacology and in vivo hemodynamic profile of human urotensin-II, it plays a pathological role in cardiovascular diseases characterized by excessive or abnormal vasoconstriction and myocardial dysfunction. (Ames et al. Nature 1990, 401, 282.)

Compounds that antagonize the urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since urotensin-II and GPR 14 are both expressed within the mammalian CNS (Ames et al. Nature 1999, 401, 282), they also may be useful in the treatment of addiction, schizophrenia, cognitive disorders/Alzheimers disease, impulsivity, anxiety, stress, depression, pain, migraine, neuromuscular function, Parkinsons, movement disorders, sleep-wake cycle, and incentive motivation.

Functional urotensin-II receptors are expressed in rhabdomyosarcomas cell lines and therefore may have oncological indications. Urotensin may also be implicated in various metabolic diseases such as diabetes and in various gastrointestinal disorders, bone, cartilage, and joint disorders (e.g., arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for compounds and pharmaceutical compositions containing them.

In a second aspect, this invention provides for the use of these compounds as antagonists of urotensin II, and as inhibitors of urotensin II.

In another aspect, this invention provides for the use of these compounds for treating conditions associated with urotensin II imbalance.

In yet another aspect, this invention provides for the use of these compounds for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhage stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and $_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula (I):

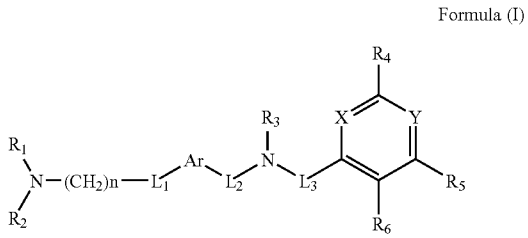

Formula (I)

wherein Ar is selected from the group consisting of aryl, heteroaryl, benzoheteroaryl, pyridone, pyridazinone, and pyrimidone;

n is 1–6;

$R_1$ and $R_2$ are independently H, alkyl or aralkyl or $R_1$ and $R_2$ along with N can form a pyrrolidine, piperadine, piperazine, morpholine, benzopyrrolidine, benzopiperadine or benzopiperazine ring or $R_1$ and $L_1$ or $R_1$ and one carbon of $(CH_2)n$ can form a 5, 6, or 7 membered ring;

$R_3$ is H, alkyl or aralkyl;

X and Y are independently C or N;

$R_4$, $R_5$, and $R_6$ are independently selected from the group consisting of H, alkyl, aralkyl, aryl, heteroaryl, benzoheteroaryl, hydroxyl, halo, haloalkyl, alkoxy, aminocarbonyl and aminosulfonyl or $R_5$ and $R_6$ together can form a 5-6 membered aromatic ring or a 5–7 membered aliphatic ring;

$L_1$ is selected from the group consisting of a single bond, O, $NR_7$, CO, $SO_2$, $NR_8CO$, $NR_9SO_2$, $NR_{10}CONR_{11}$, $NR_{12}SO_2NR_{13}$, arene, heteroarene, pyridine, pyrimidone and pyridszinone;

$L_2$ and $L_3$ are independently selected from the group consisting of a single bond, $CH_2$, $NR_{14}$, CO and $SO_2$; and $R_7$–$R_{14}$ are independently selected from the group consisting of H, alkyl, aryl and aralkyl or $R_8$ and CO and Ar can form pyridone, pyridazinone, and pyrimidone, and the pharmaceutically acceptable salts thereof.

Preferred structures of Formula II are compounds of the formula:

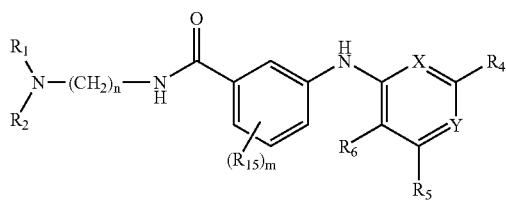

wherein each $R_{15}$ is independently H, alkyl, aralkyl, haloalkyl, aryl, heteroaryl, benzoheteroaryl, alkoxy, aminocarbonyl or aminosulfonyl; two of them can form 5-6 membered aromatic rings or 5–7 membered aliphatic rings;

m is 0–3; and $R_1$, $R_2$, $R_4$, $R_5$, $R_6$, n, X and Y are as defined above, and the pharmaceutically acceptable salts thereof.

Preferred structures of Formula I are also compounds of the formula:

$R_1$, $R_2$, $R_4$, $R_5$, $R_6$, m, n and X are defined above, and the pharmaceutically acceptable salts thereof.

Presently preferred compounds of the present invention are:

{4-Chloro-3-[2-(3,4-dihydro-1H-isoquinolin-2-yl)ethoxy]phenyl}-(2-methylquinolin-4-yl)amine.

{3-[2-(4-Benzyl-piperidin-1-yl)ethoxy]phenyl}-(2-methylquinolin-4-yl)amine.

{4-Chloro-3-[2-(4-phenylpiperidin-1-yl)ethoxy]phenyl}-(2-methylquinolin-4-yl)amine.

{3-[2-(4-Benzylpiperazin-1-yl)ethoxy]phenyl}-(2-methylquinolin-4-yl)amine.

{3-[2-(Benzylmethylamino)ethoxy]phenyl}-(2-methylquinolin-4-yl)amine.

{3-[2-(4-Benzylpiperidin-1-yl)ethoxy]-5-trifluoromethylphenyl}-(2-methylquinolin-4-yl)amine.

{3-[3-(4-Benzylpiperidin-1-yl)propoxy]phenyl}-(2-methylquinolin-4-yl)amine.

{3-[2-(1-Methyl-1-phenylethylamino)ethoxy]phenyl}-(2-methylquinolin-4-yl)amine.

[3-(2-Benzylaminoethoxy)phenyl]-(2-methylquinolin-4-yl)amine.

1-(1-{2-[3-(2-Methylquinolin-4-ylamino)phenoxy]ethyl}-4-phenylpiperidin-4-yl)ethanone.

[3-(3-Benzylaminopropoxy)phenyl]-(2-methylquinolin-4-yl)amine.

{3-[2-(2-Benzylimidazol-1-yl)ethoxy]phenyl}-(2-methylquinolin-4-yl)amine.

(1-{2-[3-(2-Methylquinolin-4-ylamino)phenoxy]ethyl}piperidin-4-yl)diphenylmethanol.

4-Benzyl-1-{2-[3-(2-tert-butylquinolin-4-ylamino)phenoxy]ethyl}piperidin-4-ol.

4-Benzyl-1-{2-[3-(2-methylquinolin-4-ylamino)-5-trifluoromethylphenoxy]ethyl}piperidin-4-ol.

{3-[2-(4-Benzylpiperidin-1-yl)ethoxy]phenyl}-(2,6-dimethylpyrimidin-4-yl)amine.

{3-[2-(5-Benzyl-2,5-diazabicyclo[2.2.1]hept-2-yl)ethoxy]phenyl}-(2-methylquinolin-4-yl)amine.

{3-[2-(4-Benzylpiperazin-1-yl)ethoxy]-5-trifluoromethylphenyl}-(2-methylquinolin-4-yl)amine.

(2-Methylquinolin-4-yl)-{3-[2-(4-phenylpiperidin-1-yl)ethoxy]-5-trifluoromethyl phenyl}amine.

{3-[3-(1-Methyl-1-phenylethylamino)propoxy]phenyl}-(2-methylquinolin-4-yl)amine.

{3-[2-(5-Benzyl-2,5-diazabicyclo[2.2.1]hept-2-yl)ethoxy]-5-trifluoromethylphenyl}-(2-methylquinolin-4-yl)amine.

N-(2-{1-[2-(3-Fluorophenyl)ethyl]-6,7-dimethoxy-3,4-dihydro-1H-isoquinolin-2-yl}ethyl)-3-(2-methylquinolin-4-ylamino)benzamide.

N-[2-(6,7-Dimethoxy-3,4-dihydro-1H-isoquinolin-2-yl)ethyl]-3-(2-methylquinolin-4-ylamino)benzamide.

N-[2-(1,3-Dihydroisoindol-2-yl)ethyl]-3-(2-methylquinolin-4-ylamino)benzamide.

N-[2-(3,4-Dihydro-1H-isoquinolin-2-yl)ethyl]-2-methyl-5-(2-methylquinolin-4-ylamino)benzamide.

N-[2-(3,4-Dihydro-1H-isoquinolin-2-yl)ethyl]-2-hydroxy-5-(2-methylquinolin-4-ylamino)benzamide.

N-[2-(3,4-Dihydro-1H-isoquinolin-2-yl)ethyl]-3-(2-trifluoromethylquinolin-4-ylamino)benzamide.

N-[2-(3,4-Dihydro-1H-isoquinolin-2-yl)ethyl]-2,4,6-trimethyl-3-(2-methylquinolin-4-ylamino)benzamide.

2-[2-(3,4-Dihydro-1H-isoquinolin-2-yl)ethyl]-4-(2-methylquinolin-4-ylamino)-2,3-dihydroisoindol-1-one.

3-(2-Methylquinolin-4-ylamino)-N-[2-(1,3,4,5-tetrahydrobenzo[c]azepin-2-yl)ethyl]benzamide.

N-[2-(3,4-Dihydro-1H-isoquinolin-2-yl)ethyl]-2,5-bis(2-methylquinolin-4-ylamino)benzamide.

3-(2-Methylquinolin-4-ylamino)-N-[2-(octahydro-cis-isoquinolin-2-yl)ethyl]benzamide.

N-(2-Azepan-1-ylethyl)-3-(2-methylquinolin-4-ylamino)benzamide.

N-(2-Benzylaminoethyl)-3-(2-methylquinolin-4-ylamino)benzamide.

4-({2-[3-(2-Methylquinolin-4-ylamino)-benzoylamino]ethylamino}methyl)benzoic acid.

N-[2-(2,2-Dimethylpropylamino)ethyl]-3-(2-methylquinolin-4-ylamino)benzamide.

N-[2-(4-Benzylpiperazin-1-yl)ethyl]-3-(2-methylquinolin-4-ylamino)benzenesulfonamide.

{3-[5-(3,4-Dihydro-1H-isoquinolin-2-ylmethyl)isoxazol-3-yl]phenyl}-(2-methylquinolin-4-yl)amine.

{3-[3-(3,4-Dihydro-1H-isoquinolin-2-yl)propyl]-4-methylphenyl}-(2-methylquinolin-4yl)amine.

$N^1$-[2-(3,4-Dihydro-1H-isoquinolin-2-yl)ethyl]-$N^7$-(2-methylquinolin-4-yl)-1,2,3,4-tetrahydronaphthalene-1,7-diamine.

[3'-(3,4-Dihydro-1H-isoquinolin-2-ylmethyl)biphenyl-4-yl]-(2-methylquinolin-4-yl)amine.

{3-[2-(4-Benzylpiperidin-1-yl)ethanesulfonyl]phenyl}-(2-methylquinolin-4-yl)amine.

N-[2-(4-Benzylpiperidin-1-yl)ethyl]-N'-(2-methylquinolin-4-yl)pyrimidine-4,6-diamine.

3-(4-Benzylpiperidin-1-yl)-1-[3-(2-methylquinolin-4-ylamino)phenyl]propan-1-one oxime.

The term "alkyl" as used herein, alone or in combination, refers to $C_1$–$C_6$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "aryl", "arene" or "aromatic" as used herein alone or in combination, refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-napthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "heteroaryl" or "heteroarene" as used herein, alone or in combination, refers to a 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "optical isomers" as used herein refers to compounds which differ only in the stereochemistry of at least one atom, including enantiomers, diastereomers and racemates.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylbeterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —N—H—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in Advanced Organic Chemistry by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, sulfonyl and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfanyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, carboxy lower alkyl, arylalkoxy, alkanoylamino, alkanoyl (lower alkyl) amino, lower alkylsufonylamino, arylsulfonylamino, alkylsulfonyl (lower alkyl) amino, arysulfonyl (lower alkyl) amino, lower alkylcarboxamide, di(lower alkyl) carboxamide, sulfonamide, lower alkylsulfonamide, di(lower alkyl sulfonamide, lower alkylsulfonyl, arylsulfonyl and alkyldithio.

As used herein, the term "composition" is intended to encompass a product comprising the specified ingredients in the specified amounts, a well as any product which results, directly or indirectly, from a combination of the specified ingredients in the specified amounts.

As used herein, the term "mammals" includes humans and other animals.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, dighiconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) hurnectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or iastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiorners on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Preferably the composition is in unit dosage form, for example a tablet, capsule or metered aerosol dose, so that the patient may administer to themselves a single dose.

Each dosage unit for oral administration contains suitably from 0.0001 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.01 mg/Kg to 40 mg/Kg, of a compound of the Formula (I) or a pharmaceutically acceptable salt thereof calculated as the free acid. The daily dosage regimen for intranasal administration and oral inhalation is suitably about 10 to 500 mg/person. The active ingredient may be administered from 1 to 6 times a day, sufficient to exhibit the desired activity.

These compounds may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis, atheroscloerosis, dyslipidemia, addiction, schizophrenia, cognitice disorders/Alzheimers disease, impulsivity, anxiety, stress, depression, pain, neuromuscular function, diabetes, gastric reflux, gastric motility disorders, ulcers and genitourinary diseases.

The urotension antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and I-adrenoceptor antagonists.

The biological activity of the compounds of Formula (I) are demonstrated by the following tests:

1) Inhibition of Human [$^{125}$I]-Urotensin-II Binding to Urotensin-II Receptor Binding of human [$^{125}$I]-urotensin-II to human urotensin-II receptor (UTR) was done using cell membranes from either TE-671 rhabdomyosarcoma cells or CHO cells stably expressing recombinant UTR, in a homogeneous Scintillation Proximity Assay (SPA).

The UTR cells membranes were pre-coupled overnight at 4° C. to WGA-PVT beads (Amersham RPNQ0001) at a ratio of 5–25 μg membrane to 0.5 mg beads/assay. Assay was performed in 96-well microtiter Optiplates (Packard 6005290) by mixing coupled beads and 0.1 nM [$^{125}$I U-II (2200 Ci/mmol, NEN NEX379), in a total volume of 100 μl 20 mM HEPES, 5 mM MgCl$_2$, pH 7.4. Test compounds were diluted in DMSO and were put in the assay at a final concentration of 1% DMSO. Incubation was done for 3 hours at 37° C. followed by reading in a TopCount scintillation microplate reader. Nonspecific binding was determined by adding 100 nM unlabeled human U-II (Phoenix Pharmaceuticals, 071-05) to the assay mixture. Analysis of the assay was performed using nonlinear least square fitting.

1) Inhibition of Human Urotensin-II-induced Ca$^{2+}$ mobilization in UTR Cells:

The function of urotensin-II was determined by measuring ligand-induced mobilization of intracellular Ca$^{2+}$ in a Flex-Station scanning fluorometer (Molecular Devices). UTR cells were plated overnight at 50,000 cells/well in 96-well black/clear plates (Costar brand, Fisher 07-200-588). Cells were labeled with fluo-4AM dye (Molecular Probes, F-14201) in Hank's balanced salt solution (HBSS), 20 mM HEPES, 25 mM probenecid, pH 7.4, and then were washed with buffer. During the assay, cells were continuously monitored in the FlexStation and exposed to test compounds at a final concentration of 0.1% DMSO, followed by the addition of 1 nM human U-II. Fluorescence was read every 2 seconds for 2 minutes. The excitation and emission wavelengths used were 485 nm and 525 nm. Inhibition of the urotensin-II-induced signal was calculated using a nonlinear least square fitting program. Compounds of the present invention are active in these assays and have an $IC_{50}$ of <10 μM (Example 7 $IC_{50}$=6.5 μM).

The following Examples are illustrative but not limiting of the present invention:

EXAMPLE 1

N-(2-Dimethylamino-ethyl)-3-(2-methyl-quinolin-4-ylamino)-benzenesulfonamide

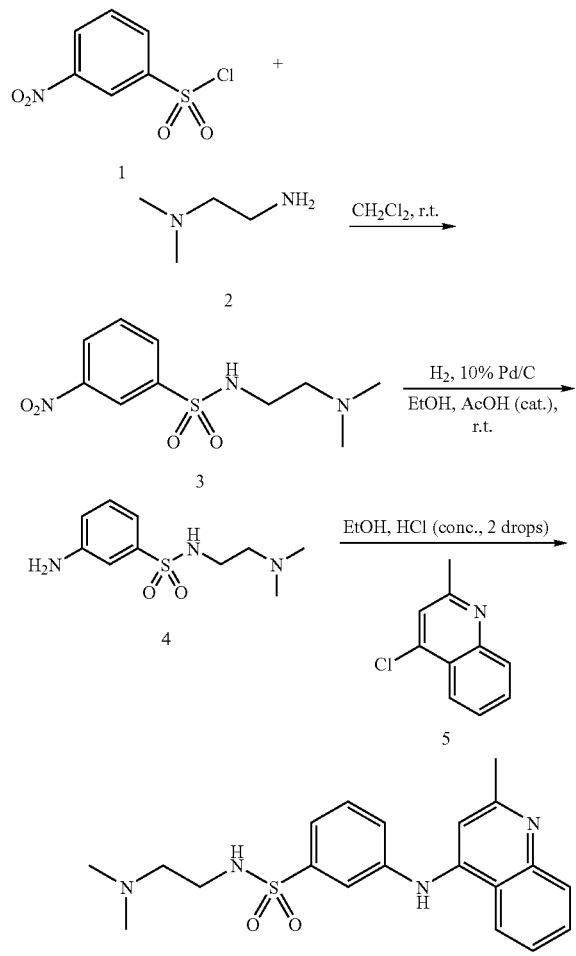

Example 1

Step 1. N-(2-Dimethylamino-ethyl)-3-nitro-benzenesulfonamide (3).

To a solution of 3-nitrobenzenesulfonyl chloride (1, 1.0 g, 4.51 mmol) in anhydrous $CH_2Cl_2$ (9.0 mL) was added N,N-dimethyl-ethylenediamine (2, 0.5 mL, 4.55 mmol) dropwise. The resulting solution was stirred at room temperature overnight before it was diluted with EtOAc (80 mL). The organic mixture was washed with saturated $NaHCO_3$ (90 mL), brine (90 mL), and dried over $MgSO_4$. The solids were filtered and the filtrate was concentrated on a rotavap to give 3 as a foam (0.8 g) which was used in the next step without further purification.

Step 2. 3-Amino-N-(2-dimethylamino-ethyl)-benzenesulfonamide (4).

A solution of 3 (0.8 g) in ethanol (10 mL) was subjected to catalytic hydrogenation (10% Pd/C, Degussa, 0.8 g, 3 drops of AcOH, 1 atm.) overnight. To work up, the solids were filtered the filtrate was dried under vacuum to afford 4 as a solid (0.71 g) which was used in the next step without further purification.

Step 3. N-(2-Dimethylamino-ethyl)-3-(2-methyl-quinolin-4-ylamino)-benzenesulfonamide.

To a solution of 4 (0.3 g, 1.23 mmol) and 4-chloroquinaldine (5, 0.26 mL, 1.29 mmol) in ethanol (10 mL) were added 2 drops of conc. HCl. The resulting mixture was heated under reflux overnight before ethanol was removed under reduced pressure. The residue was basified with saturated $NaHCO_3$ (aq. 20 mL) and the basic solution was extracted with EtOAc (2×20 mL). The combined organic layers were dried over $MgSO_4$, the solids were filtered and the filtrate was concentrated on a rotavap. The residue was purified on Florisil® to give the title compound as an orange solid (15 mg).

EXAMPLE 2

N-(2-Dimethylamino-ethyl)-3-(2-methyl-quinolin-4-yl-amino)-benzamide

The title compound was synthesized in the same manner as for Example 1 except that 3-nitrobenzoyl chloride was used instead of 1 in Step 1. It was obtained as a pale yellow solid.

EXAMPLE 3

(3-(2-Dimethylamino-ethoxy)-4-methyl-phenyl)-(2-methyl-quinolin-4-yl)-amine

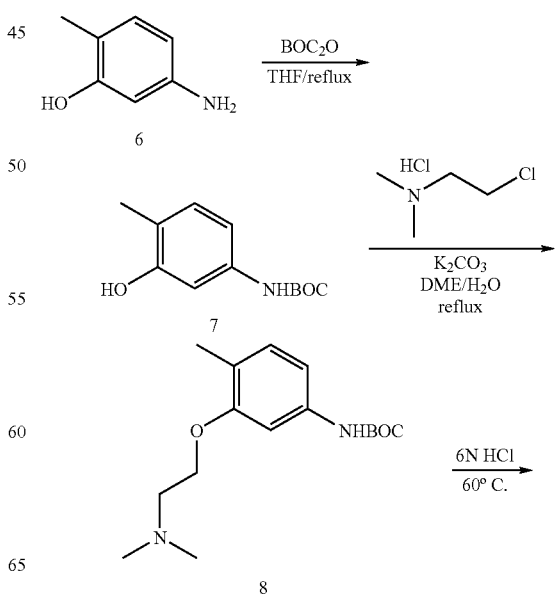

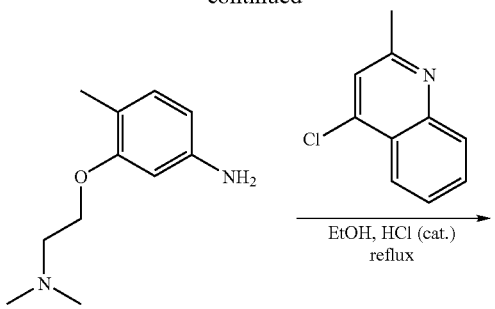

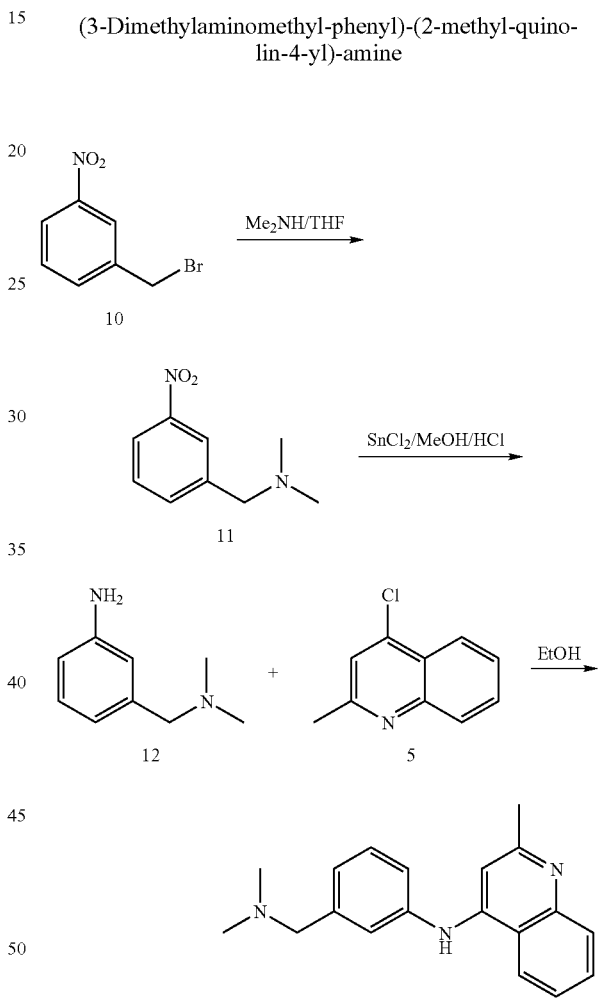

Example 3

Step 1. tert-Butyl (3-hydroxy-4-methyl-phenyl)-carbamate (7).

A solution of 5-amino-2-methylphenol (6, 1.0 g, 8.12 mmol) and di-tert-butyl dicarbonate (1.95 g, 8.93 mmol) in THF (25 mL) was heated under reflux overnight. After cooling to room temperature, the solution was diluted with EtOAc (75 mL) and the resulting mixture was washed with water (70 mL), 1N HCl (2×70 mL) and brine (70 mL). The organic layer was then dried over $MgSO_4$, the solids were filtered, and the filtrate was concentrated under reduced pressure. The desired product 7 was obtained as an oil (2.16 g) and was carried on to the next step without further purification.

Step 2. tert-Butyl (3-(2-dimethylamino-ethoxy)-4-methyl-phenyl)-carbamate (8).

A mixture of 7 (2.16 g, 9.68 mmol), 2-(dimethylamino)-ethyl chloride hydrochloride (1.53 g, 10.6 mmol) and $K_2CO_3$ (5.35 g, 3.87 mmol) in DME (28 mL)/$H_2O$ (7 mL) was heated under reflux overnight. After cooling to room temperature, the solution was diluted with EtOAc (100 mL) and the resulting solution was washed with $H_2O$ (2×100 mL) and brine (100 mL).

The organic layer was dried over $MgSO_4$, the solids were filtered, and the filtrate was concentrated under reduced pressure. The residue was purified on silica gel to give 8 as an oil (1.15 g) which upon standing became a solid.

Step 3. 3-(2-Dimethylamino-ethoxy)-4-methylaniline (9).

A solution of 8 (1.15 g) in 6N HCl (10 mL) was heated at 60° C. for 4 hours. After cooling to room temperature, the solution was neutralized with 6N NaOH solution. The aqueous mixture was extracted with EtOAc (2×30 mL), the combined organic layers were washed with brine (1×50 mL) and dried over $MgSO_4$. The solids were filtered, and the filtrate was concentrated under reduced pressure to give the desired product as an oil (0.68 g).

Step 4. (3-(2-Dimethylamino-ethoxy)-4-methyl-phenyl)-(2-methyl-quinolin-4-yl)-amine.

To a solution of 9 (0.25 g, 1.29 mmol) and 5 (0.29 ml, 1.44 mmol) in EtOH (8 mL) were added 2 drops of conc. HCl. The mixture was heated under reflux overnight. After cooling to room temperature, EtOH was removed under reduced pressure. The residue was partitioned between sat. $NaHCO_3$ (aq.) and EtOAc (100 mL each) and the aqous layer was extracted with EtOAc (2×50 mL). The combined organic layers were dried over $MgSO_4$, the solids were filtered, and the filtrate was concentrated under reduced pressure. The residue was purified on Florisil® (50% EtOAc/Hexanes to 15% MeOH/EtOAc) to yield the title compound as a light yellow solid (0.25 g).

The compounds of Examples 4–11 were synthesized in the same manner as Example 3.

EXAMPLE 12

(3-Dimethylaminomethyl-phenyl)-(2-methyl-quinolin-4-yl)-amine

Example 12

Step 1. Dimethyl-(3-nitrobenzyl)-amine (11).

A solution of 3-nitrobenzyl bromide (10, 1.67 g, 7.73 mmol) and N,N-dimethylamine (4.25 mL, 2M in THF) in anhydrous THF (30 mL) was heated at 40° C. overnight. The reaction mixture was diluted with 1N HCl (30 mL, aq.), the aqueous layer separated, and extracted with EtOAc (30 mL). The pH of the aqueous layer was then adjusted to 9 using saturated $Na_2CO_3$ (aq.) and the aqueous layer was extracted with EtOAc (50 mL). The organic layer was washed with water (40 mL), brine (40 mL), and dried over $Na_2SO_4$. The solids were filtered and the filtrate was concentrated on a rotavap to give 11 (1.2 g).

Step 2. 3-Dimethylaminomethylaniline (12)

To a solution of 11 (1.2 g, 6.67 mmol) in methanol (100 mL) were sequentially added conc. HCl (10 mL) and SnCl$_2$ (5 g, 26.67 mmol). The reaction mixture was stirred at room temperature overnight before it was partitioned between water and EtOAc (200 mL each). The organic layer was separated and washed with water (150 mL), brine (150 mL) and dried over Na$_2$SO$_4$. The solids were filtered and the filtrate was concentrated on a rotavap to give 12 (500 mg).

Step 3. (3-Dimethylaminomethyl-phenyl)-(2-methyl-quinolin-4-yl)-amine.

The title compound was synthesized in the same manner as shown in Step 3 of Example 1 and it was obtained as a yellowish solid (230 mg)

EXAMPLE 13

(4-Chloro-3-(2-(1-(2-(3,4-dimethoxy-phenyl)-ethyl)-6,7-dimethoxy-3,4-dihydro-1H-isoquinolin-2-yl)-ethoxy)-phenyl)-(2-methyl-quinolin-4-yl)-amine.

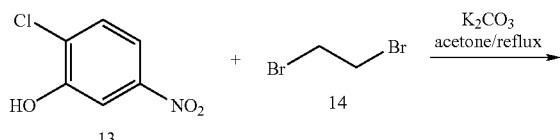

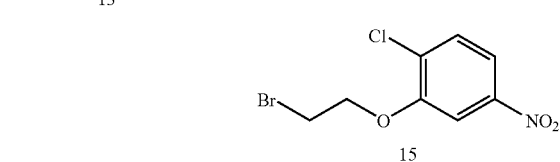

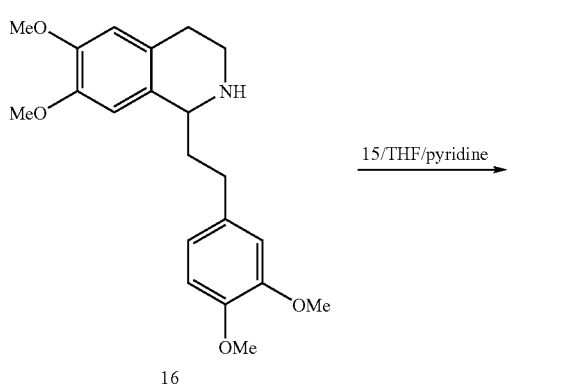

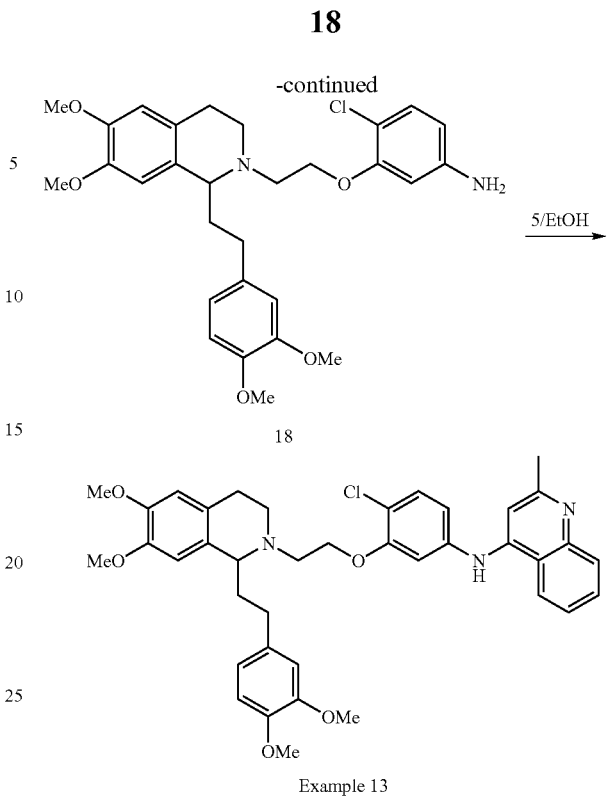

Example 13

Step 1. 2-(2-Bromo-ethoxy)-1-chloro-4-nitrobenzene (15)

To a solution of 2-chloro-5-nitro-phenol (13, 0.87 g, 5 mmol) in acetone (10 mL) were sequentially added 1,2-dibromoethane (14, 0.85 ml, 10 mmol) and K$_2$CO$_3$ (1.45 g, 10.5 mmol). The mixture was heated under reflux over night. To work up, the solids were filtered and the filtrate was concentrated. The residue was purified by chromatography (silica gel) eluting with hexanes first, then EtOAc to yield 15 (600 mg).

Step 2. 2-(2-(2-Chloro-5-nitro-phenoxy)-ethyl)-1-(2-(3,4-dimethoxy-phenyl)-ethyl)-6,7-dimethoxy-1,2,3,4-tetrahydro-isoquinoline (17)

To a solution of 15 (315 mg, 1.13 mmol) in anhydrous THF (3 mL) were sequentially added 1-(2-(3,4-dimethoxy-phenyl)-ethyl)-6,7-dimethoxy-1,2,3,4-tetrahydro-isoquinoline (16, Morimoto et al, Heterocycles 1996 43:2557; Brossi et al, Helv Chim Acta 1960 43:1459; Meyers et al, Tetrahedron Lett 1981 22:5115; Meyers et al, J Am Chem Soc 1983 105:117) (404 mg, 1.13 mmol) and pyridine (0.3 mL). The reaction mixture was heated under reflux for 2 days before it was partitioned between EtOAc and water (20 mL each). The organic layer was separated, washed with water (15 mL), brine (15 mL), and dried over Na$_2$SO$_4$. The solids were filtered and the filtrate was purified by chromatography (silica gel) eluting with hexanes:EtOAc (1:1) to give 17 (205 mg)

Step 3. 4-Chloro-3-(1-(2-(3,4-dimethoxy-phenyl)-ethyl)-6,7-dimethoxy-1,2,3,4-tetrahydro-isoquinolin-2-yl)-ethoxy)aniline (18)

To a solution of 17 (205 mg, 0.369 mmol) in methanol (10 mL) were sequentially added conc. HCl (0.5 mL) and SnCl$_2$ (280 mg, 1.48 mmol). The mixture was stirred at room temperature for 8 hours before it was diluted with water (100 mL) and the pH was adjusted to 10 using 2N NaOH. The mixture was extracted with EtOAc (150 mL) and the organic layer was washed with water and brine (100 mL each) and then dried over Na$_2$SO$_4$. The solids were filtered and the filtrate was concentrated on a rotavap to give 18 (170 mg).

Step 4. (4-Chloro-3-(2-(1-(2-(3,4-dimethoxy-phenyl)-ethyl)-6,7-dimethoxy-3,4-dihydro-The title compound was synthesized in the same manner as shown in Example 1/Step 3 using 5 and 18. It was obtained as a yellow solid (79 mg).

EXAMPLE 14

1-(4-Chloro-3-(2-dimethylamino-ethoxy)-phenyl)-3-(2-methyl-quinolin-4-yl)-urea

To a solution containing 4-aminoquinaldine (74 mg, 0.46 mmol) in anhydrous THF (5.0 Ml) was added triethylamine (0.2 Ml, 1.4 mmol). The solution was cooled to 0° C. followed by the addition of triphosgene (45.0 mg, 0.18 mmol). The reaction mixture was stirred at 0° C. for 10 minutes before the addition of a solution of 4-chloro-3-(2-dimethylamino-ethoxy)aniline (100.0 mg, 0.46 mmol, for its synthsis see Steps 1–3 for Example 1) in THF (2 Ml). The ice bath was removed and the mixture was heated at 65° C. for 2 hours before it was poured into a mixture of CH$_2$Cl$_2$/MeOH (20 Ml, 7:1 ratio). The resulting mixture was washed with 10% sodium bicarbonate (aq. 15.0 Ml). The organic layer was dried over MgSO$_4$ and concentrated. The oily residue was chromatographed over silica gel (eluent: 20% MeOH in EtOAc) to give the desired product as an off-white solid (82.0 mg, 45% yield).

The compounds of Example 15 and 16 were synthesized in the same manner as for Example 2.

TABLE 1

| Example | Structure | Name | Physical Description | M + H |
|---|---|---|---|---|
| 1 | 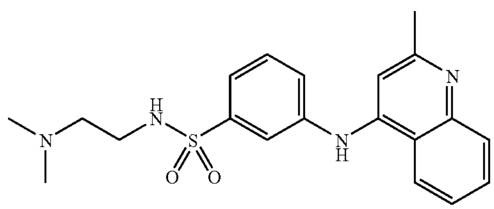 | N-(2-dimethylamino-ethyl)-3-(2-methyl-quinolin-4-ylamino)-benzenesulfonamide | orange solid | 385.27 |
| 2 | 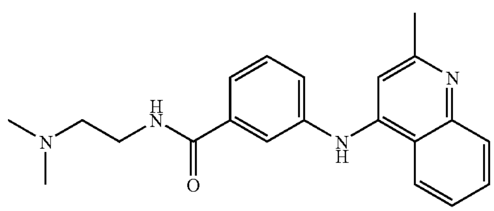 | N-(2-dimethylamino-ethyl)-3-(2-methyl-quinolin-4-ylamino)-benzamide | pale yellow solid | 349.29 |
| 3 | 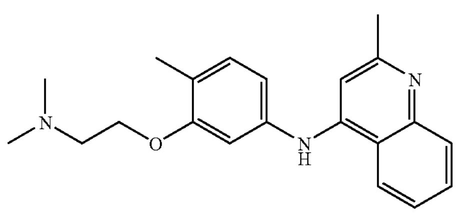 | (3-(2-dimethylamino-ethoxy)-4-methyl-phenyl)-(2-methyl-quinolin-4-yl)-amine | light yellow solid | 336.25 |
| 4 | 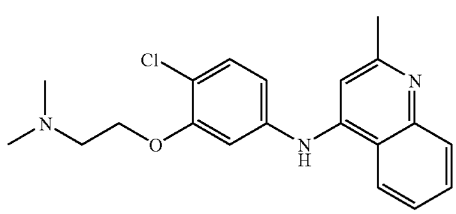 | (4-chloro-3-(2-dimethyl amino-ethoxy)-phenyl)-(2-methyl-quinolin-4-yl)-amine | yellow solid | 355.19 |
| 5 | 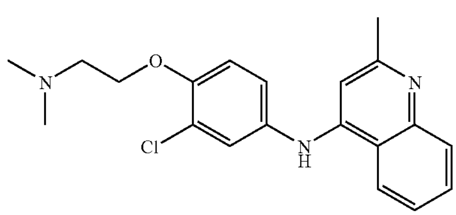 | (3-chloro-4-(2-dimethyl amino-ethoxy)-phenyl)-(2-methyl-quinolin-4-yl)-amine | yellow solid | 356.24 |

TABLE 1-continued

| Example | Structure | Name | Physical Description | M + H |
|---|---|---|---|---|
| 6 | 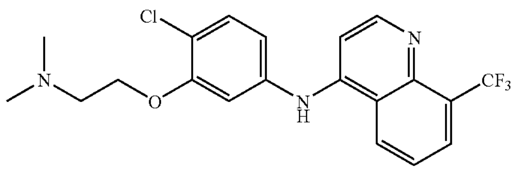 | (4-chloro-3-(2-dimethyl amino-ethoxy)-phenyl)-(8-trifluoromethyl-quinolin-4-yl)-amine | white solid | 410.18 |
| 7 | 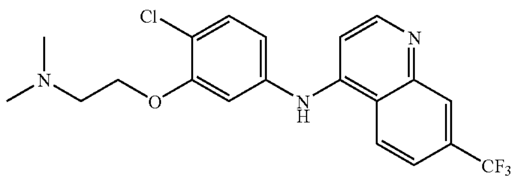 | (4-chloro-3-(2-dimethyl amino-ethoxy)-phenyl)-(7-trifluoromethyl-quinolin-4-yl)-amine | yellow solid | 410.12 |
| 8 | 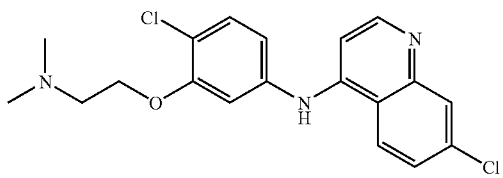 | (4-chloro-3-(2-dimethyl amino-ethoxy)-phenyl)-(7-chloro-quinolin-4-yl)-amine | yellow solid | 376.22 |
| 9 | 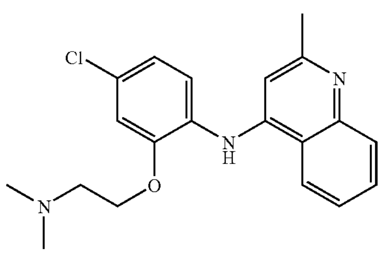 | (4-chloro-2-(2-dimethyl amino-ethoxy)-phenyl)-(2-methyl-quinolin-4-yl)-amine | yellow oil | 356.18 |
| 10 | 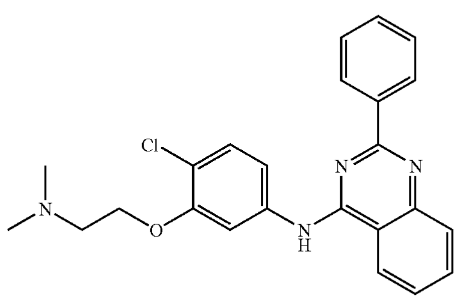 | 4-chloro-3-(2-dimethyl amino-ethoxy)-phenyl)-(2-phenyl-quinazolin-4-yl)-amine | yellow solid | 419.24 |
| 11 | 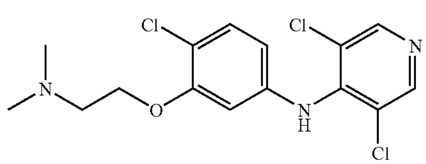 | (4-chloro-3-(2-dimethyl amino-ethoxy)-phenyl)-(3,5-dichloro-pyridin-4-yl)-amine | oil | 360.11 |
| 12 | 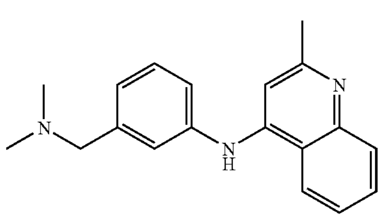 | (3-dimethyl aminomethyl-phenyl)-(2-methyl-quinolin-4-yl)-amine | yellowish solid | 291.27 |

TABLE 1-continued

| Example | Structure | Name | Physical Description | M + H |
|---------|-----------|------|---------------------|-------|
| 13 | 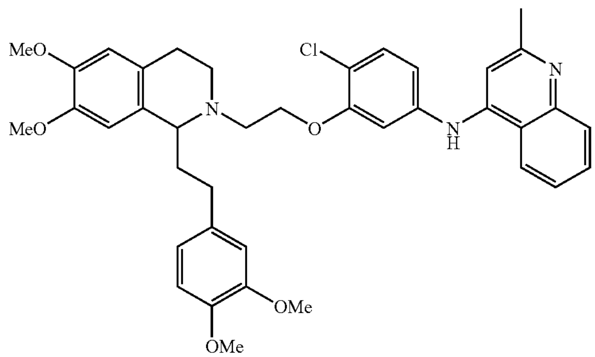 | (4-chloro-3-(2-(1-(2-(3,4-dimethoxy-phenyl)-ethyl)-6,7-dimethoxy-3,4-dihydro-1H-isoquinolin-2-yl)-ethoxy)-phenyl)-(2-methyl-quinolin-4-yl)-amine | yellow solid | 668.35 |
| 14 | 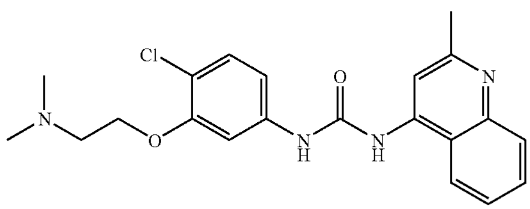 | 1-(4-chloro-3-(2-dimethyl amino-ethoxy)-phenyl)-3-(2-methyl-quinolin-4-yl)-urea | off-white solid | 399.23 |
| 15 | 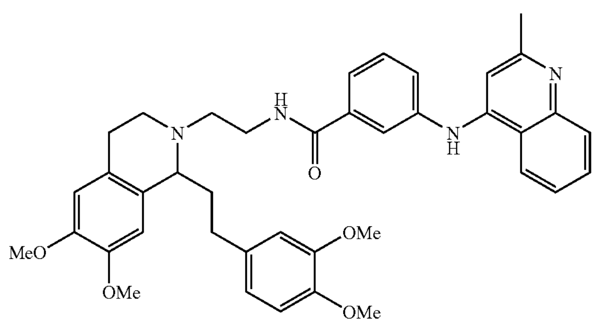 | N-(2-(1-(2-(3,4-dimethoxy-phenyl)-ethyl)-6,7-dimethoxy-3,4-dihydro-1H-isoquinolin-2-yl)-ethyl) 3-(2-methyl-quinolin-4-yl)amino-benzamide | light yellow solid | 661.39 |
| 16 | 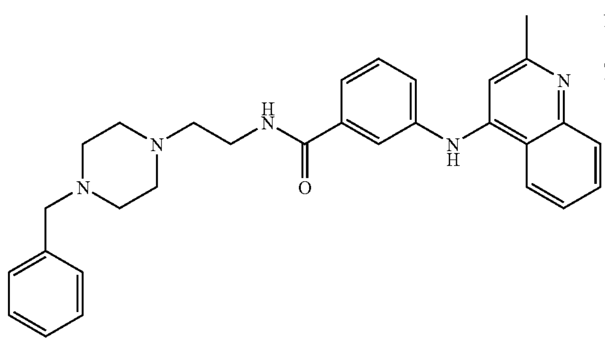 | N-(2-(4-benzyl-piperazin-1-yl)-ethyl)-3-(2-methyl-quinolin-4-yl)-amino-benzamide | light yellow foam | 480.37 |

The structures, chemical names, physical descriptions and M+H data for the compounds of Examples 17–76 are set forth in Table 2.

The compound of Example 17 was synthesized by methylating the compound of Example 3 using a standard method (NaH/DMF/MeI).

The compounds of Examples 18 and 19 were synthesized in the same manner as the compound of Example 3.

The compounds of Examples 20 to 32 were synthesized in the same manner as the compound of Example 13.

The compound of Example 33 was synthesized in the same manner as the compound of Example 13 except that 3-nitro-5-trifluoromethylphenol was used instead of 13. 3-Nitro-5-trifluoromethylphenol was synthesized by demethylating 3-nitro-5-trifluoromethylanisole using a standard method (BBr$_3$/CH$_2$Cl$_2$).

The compound of Example 34 was synthesized by hydrolysis of the compound of Example 32 using a standard method (NaOH/MeOH/THF).

The compounds of Examples 35 to 44 were synthesized in the same manner as the compound of Example 13.

The preparation of the compound of Example 45 is shown.

The compounds of Examples 46 to 54 were synthesized in the same manner as the compound of Example 13.

The preparation of the compound of Example 55 is shown.

The compounds of Examples 56 and 57 were synthesized in the same manner as the compound of Example 13.

The compound of Example 58 was synthesized in the same manner as the compound of is Example 13 except that 4-chloro-2-tert-butylquinoline (C Wolf, R Lerebours: J Org Chem 2003, 68:7077–7084) was used instead of 4-chloro-2-methylquinoline.

The compound of Example 59 was synthesized in the same manner as the compound of Example 13.

The compound of Example 60 was synthesized by acylating the compound of Example 21 using a standard method (NaH/DMF/AcCl).

The compound of Example 61 was synthesized in the same manner as the compound of Example 13.

The compound of Example 62 was synthesized in the same manner as the compound of Example 33.

The compounds of Examples 63 to 65 were synthesized in the same manner as the compound of Example 13.

The compound of Example 66 was synthesized in the same manner as the compound of Example 13 and it was obtained as the dehydration product of the intended (1-{2-[3-(2-methylquinolin-4-ylamino)phenoxy]ethyl}piperidin-4-yl)diphenylmethanol.

The compound of Example 67 was synthesized in the same manner as the compound of Example 33.

The compound of Example 68 was synthesized by the hydrolysis of the compound of Example 65 (NaOH/MeOH/THF/65° C./2 days).

The compound of Example 69 was synthesized by the hydrolysis of the compound of Example 36 (NaOH/MeOHWTHF).

The compounds of Examples 70 and 71 were synthesized in the same manner as the compound of Example 33.

The compounds of Examples 72 and 73 were synthesized in the same manner as the compound of Example 13.

The compound of Example 74 was synthesized in the same manner as the compound of Example 33.

The compounds of Examples 75 and 76 were synthesized in the same manner as the compound of Example 13.

EXAMPLE 45

{3-[2-(4-Benzenesulfonylpiperazin-1-yl)ethoxy]phenyl}-(2-methylquinolin-4-yl)amine

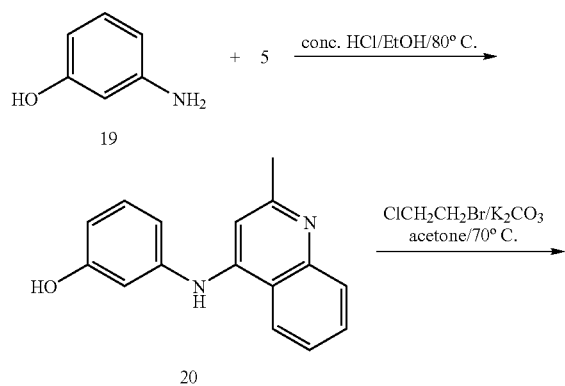

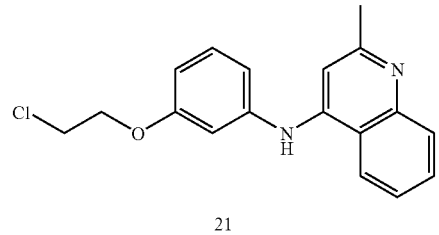

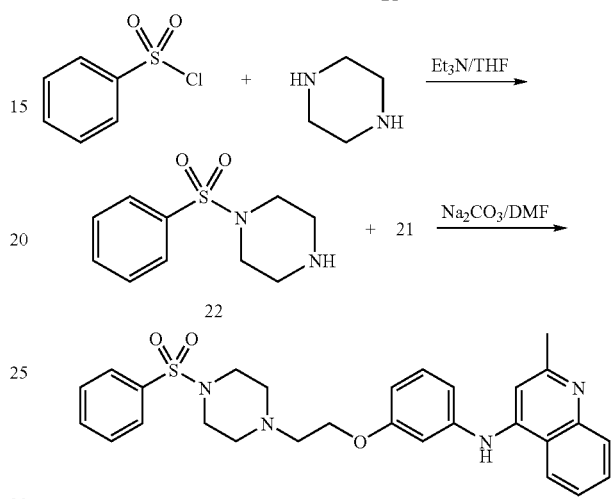

Example 45

Step 1. 3-(2-Methylquinolin-4-ylamino)phenol (20).
20 is prepared by the procedure of Example 1 Step 3.

Step 2. [3-(2-Chloroethoxy)phenyl]-(2-methylquinolin-4-yl)amine (21).

To a heterogeneous mixture of 20 (2.16 g, 6.90 mmol) in acetone (22 mL) were sequentially added 1-bromo-2-chloroethane (7.2 mL, 86.50 mmol) and potassium carbonate (3.00 g, 21.71 mmol). The reaction was stirred and heated at 70° C. for 17 hours before it was allowed to cool to room temperature and was filtered. The solids were rinsed with a 3:1 mixture of dichloromethane/methanol (25 mL×3), and the filtrate was isolated and evaporated to give the crude product. Column chromatography on silica (dichloromethane to 20/1 to 15/1 to 5/1 dichloromethane/methanol) gave 21 as a pale yellow solid (0.96 g, 35.5%).

Step 3. 1-Benzenesulfonylpiperazine (22).

To a solution of benzenesulfonyl chloride (1 g, 5.66 mmol) in THF (20 mL) were sequentially added triethylamine (1.97 mL, 14.15 mmol) and piperazine (2.92 g, 33.9 mmol). The reaction was stirred at room temperature for 1 hour before it was extracted with ethyl acetate and washed with water and brine. The ethyl acetate extracts were dried over anhydrous magnesium sulfate and concentrated. The residue was chromatographed on silica gel (1:1 hexanes/ethyl acetate to 10/1 dichloromethane/methanol) to give 22 as a yellow oil.

Step 4. {3-[2-(4-Benzenesulfonylpiperazin-1-yl)ethoxy]phenyl}-(2-methylquinolin-4-yl)amine.

To a solution of 21 (250 mg, 0.67 mmol) in DMF (5 mL) were sequentially added sodium carbonate (149 mg, 1.41 mmol). and 22 (183 mg, 0.808 mmol). The reaction was placed under a $N_2$ atmosphere and heated at 90° C. for 16 hours. After cooling to room temperature, the reaction mixture was extracted with ethyl acetate and washed with water and brine. The ethyl acetate extracts were dried over anhydrous magnesium sulfate and evaporated. The residue was purified via reversed phase HPLC to yield the title compound as a pale yellow solid (20 mg, 6%).

EXAMPLE 55

{3-[2-(2-Benzylimidazol-1-yl)ethoxy]phenyl}-(2-methylquinolin-4-yl)amine

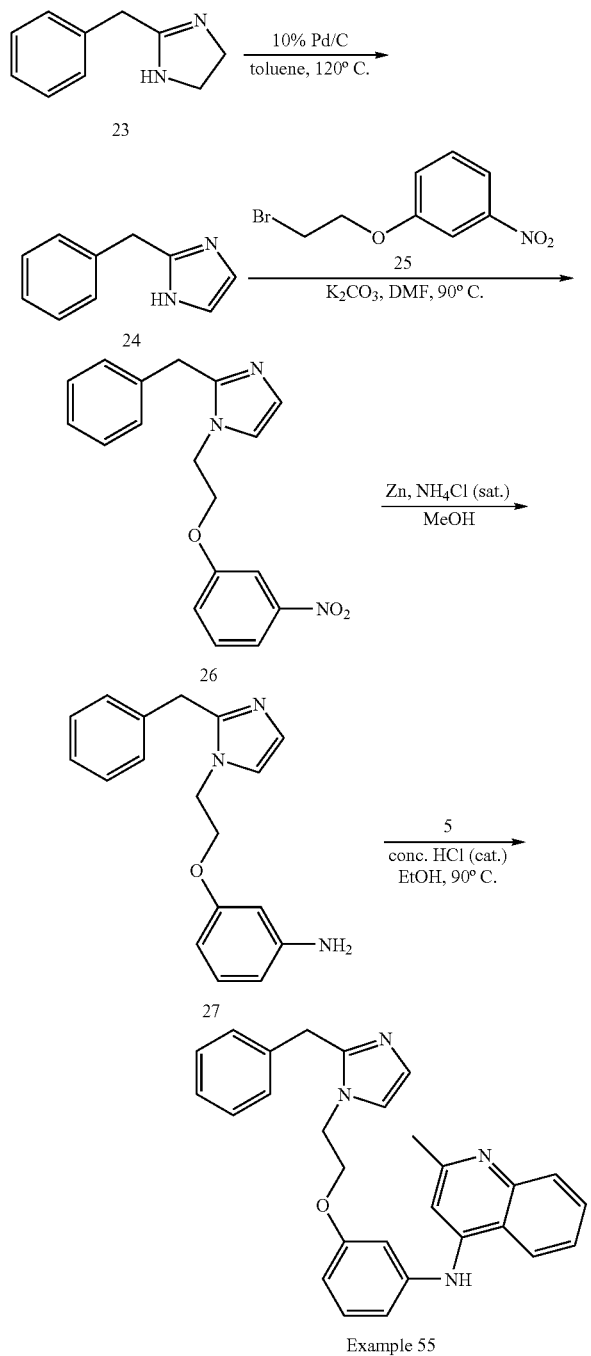

Example 55

Step 1. 2-Benzyl-1H-imidazole (24).

A mixture of 23 (0.78 g, 4.8 mmol) and 10% Pd/C (0.78 g) in toluene (25 mL) was heated at 120° C. for 48 hours. It was allowed to cool to room temperature and the solids were filtered off. The filtrate was concentrated in vaccuo and the residue was purified on silica gel column to give 24 (0.16 g, 21%).

Step 2. 2-Benzyl-1-[2-(3-nitrophenoxy)ethyl]-1H-imidazole (26).

26 is prepared from 24 and 25 by the procedure of Example 45 Step 4.

Step 3. 3-[2-(2-Benzylimidazol-1-yl)ethoxy]phenylamine (27).

27 is prepared from 26 by the procedure of Example 110 Step 4.

Step 4. {3-[2-(2-Benzylimidazol-1-yl)ethoxy]phenyl}-(2-methylquinolin-4-yl)amine.

The title compound is prepared by the procedure of Example 1 Step 3.

EXAMPLE 67

Methyl 4-benzyl-1-{2-[3-(2-methylquinolin-4-ylamino)-5-trifluoromethylphenoxy]ethyl}piperidine-4-carboxylate.

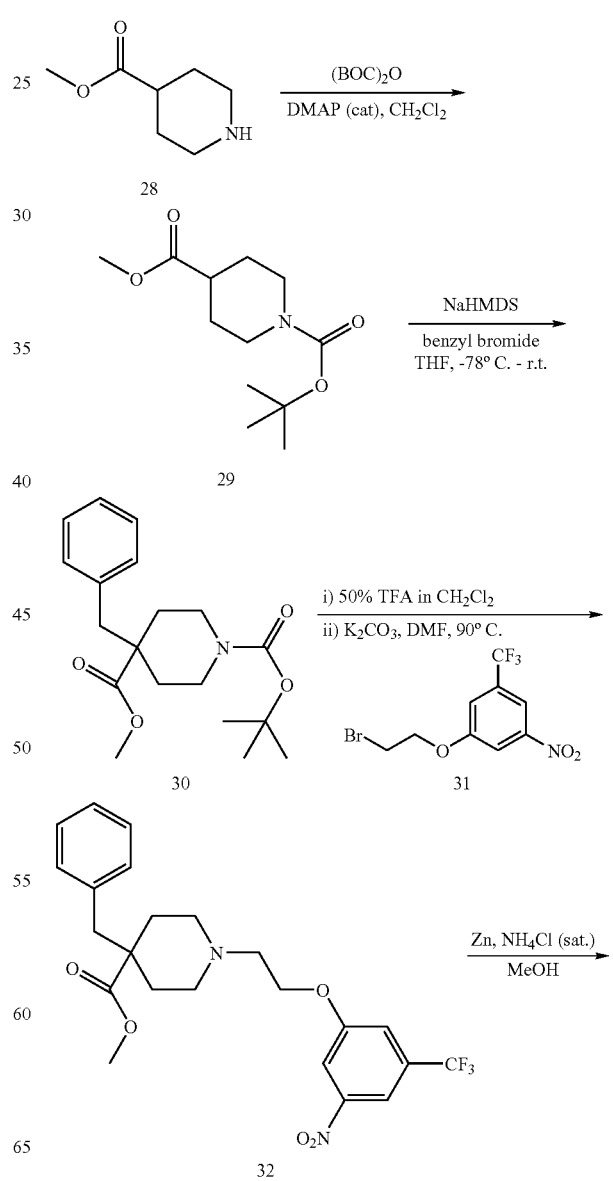

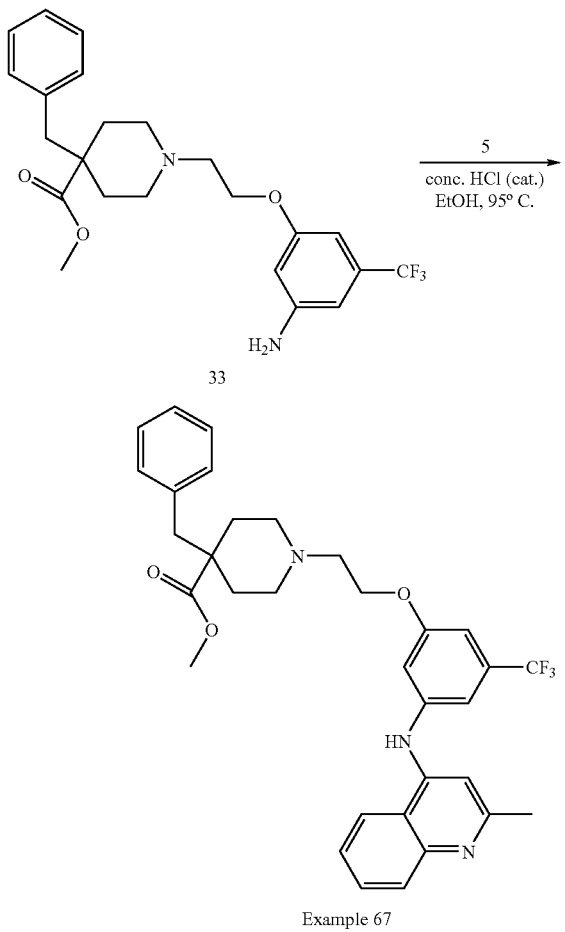

Example 67

Step 1. 1-tert-Butyl 4-methyl piperidine-1,4-dicarboxylate (29).

To a solution of methyl isonipecotate (28) (2.84 g, 19.84 mmol) and DMAP (cat.) in anhydrous CH$_2$Cl$_2$ (25 mL) at 0° C. was added di-tert-butoxycarbonate (5.20 g, 23.82 mmol). The mixture was heated under reflux for 5 hours before it was allowed to cool to room temperature and diluted with dichloromethane (100 mL). After washing with 1 N HCl (2×100 mL) and water (100 mL), the organic layer was dried over Na$_2$SO$_4$, and concentrated to provide 29 (4.64 g, 97%).

Step 2. 1-tert-Butyl 4-methyl 4-benzylpiperidine-1,4-dicarboxylate (30).

To a solution of 29 (4.64 g, 19.08 mmol) in anhydrous THF (20 mL) at −78° C. was added NaHMDS (1.0 M in THF, 22.90 mL, 22.90 mmol) slowly. It was stirred at −78° C. for 30 minutes before the addition of benzyl bromide (3.91 g, 22.87 mmol). The cold bath was removed and the reaction was allowed to warm to room temperature and stirred overnight. The mixture was diluted with EtOAc (150 mL) and washed with water (2×100 mL) and brine (100 mL). The organic layer was dried (Na$_2$SO$_4$), concentrated in vacuo, and the residue was purified by flash column chromatography to afford 30 (4.5 g, 71%).

Step 3. Methyl 4-benzylpiperidine-4-carboxylate

A solution of 30 (4.5 g, 13.5 mmol) in TFA (25 mL) and CH$_2$Cl$_2$ (25 mL) was stirred at room temperature for 40 minutes. The mixture was concentrated and the residue diluted with EtOAc (100 mL). Upon sequential washings with 1 N NaOH (2×100 mL) and water (100 mL), the organic solution was dried (Na$_2$SO$_4$) and concentrated to dryness to afford the desired product as a yellow solid (2.9 g, 92%).

Step 4. Methyl 4-benzyl-1-[2-(3-nitro-5-trifluoromethylphenoxy)ethyl]piperidine-4-carboxylate (32).

32 is prepared from 30 and 31 by the procedures of Example 45 Step 4.

Step 5. Methyl 1-[2-(3-amino-5-trifluoromethylphenoxy)ethyl]-4-benzylpiperidine-4-carboxylate (33).

33 is prepared by the procedure of Example 110 Step 4.

Step 6. Methyl 4-benzyl-1-{2-[3-(2-methylquinolin-4-ylamino)-5-trifluoromethylphenoxy]ethyl}piperidine-4-carboxylate.

The title compound is prepared from 33 by the procedure of Example 1 Step 3.

TABLE 2

| Example | Structure | Chemical name | Physical description[a] | [M + H]+ |
|---|---|---|---|---|
| 17 | 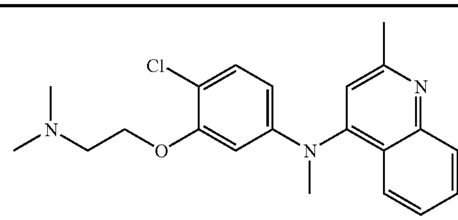 | [4-Chloro-3-(2-dimethylamino-ethoxy)phenyl]-methyl-(2-methylquinolin-4-yl)amine | yellow solid[b] | 370.34 |
| 18 | 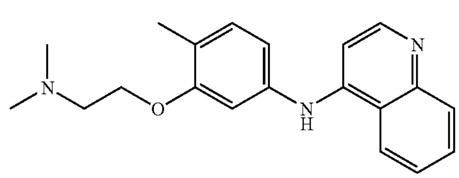 | [3-(2-Dimethylamino-ethoxy)-4-methylphenyl]-quinolin-4-ylamine | pale yellow solid | 322.24 |

TABLE 2-continued

| Example | Structure | Chemical name | Physical description[a] | [M + H]+ |
|---|---|---|---|---|
| 19 | 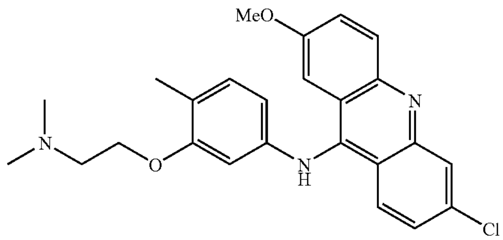 | (6-Chloro-2-methoxyacridin-9-yl)-[3-(2-dimethylamino-ethoxy)-4-methylphenyl]amine | orange-yellow solid[b] | 436.27 |
| 20 | 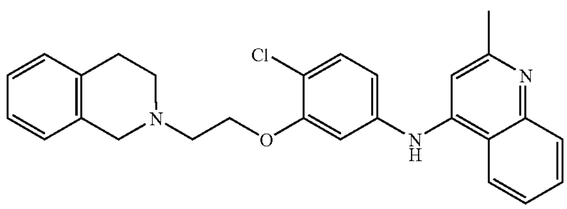 | {4-Chloro-3-[2-(3,4-dihydro-1H-isoquinolin-2-yl)ethoxy]phenyl}-(2-methylquinolin-4-yl)amine | yellowish solid | 444.20 |
| 21 | 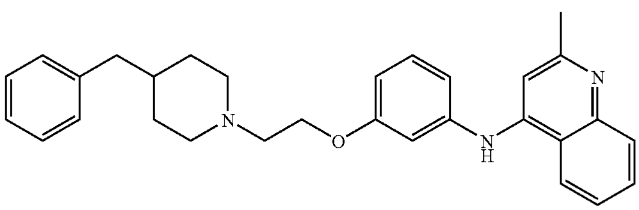 | {3-[2-(4-Benzyl-piperidin-1-yl)ethoxy]phenyl}-(2-methylquinolin-4-yl)amine | yellow solid | 452.34 |
| 22 | 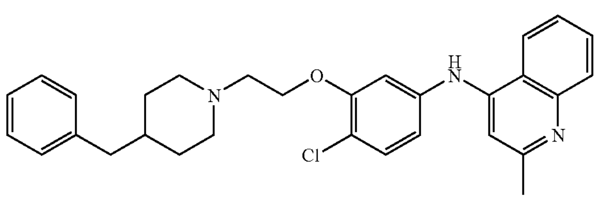 | {3-[2-(4-Benzyl-piperidin-1-yl)ethoxy]-4-chlorophenyl}-(2-methylquinolin-4-yl)amine | off-white solid | 486.30 |
| 23 | 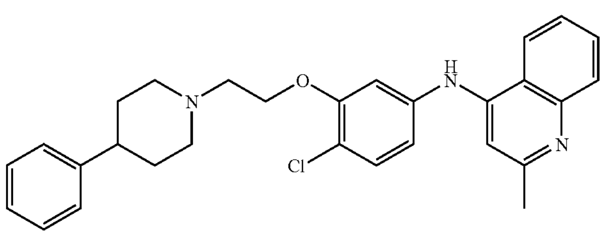 | {4-Chloro-3-[2-(4-phenylpiperidin-1-yl)ethoxy]phenyl}-(2-methylquinolin-4-yl)amine | white solid[b] | 472.22 |
| 24 | 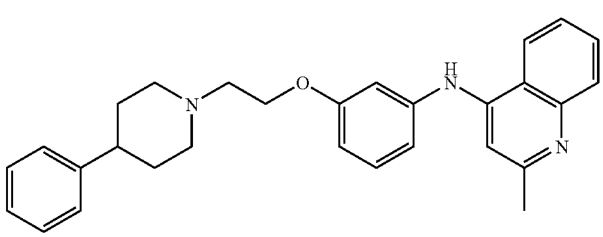 | (2-Methylquinolin-4-yl)-{3-[2-(4-phenyl-piperidin-1-yl)ethoxy]phenyl}amine | brown solid[b] | 438.26 |

TABLE 2-continued

| Example | Structure | Chemical name | Physical description[a] | [M + H]+ |
|---|---|---|---|---|
| 25 | 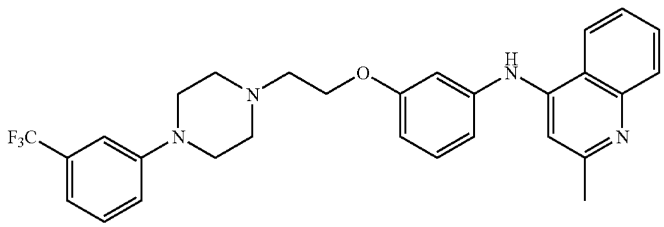 | (2-Methylquinolin-4-yl)-(3-{2-[4-(3-trifluoromethyl-phenyl)piperazin-1-yl]ethoxy}phenyl)amine | brown solid | 551.31[c] |
| 26 | 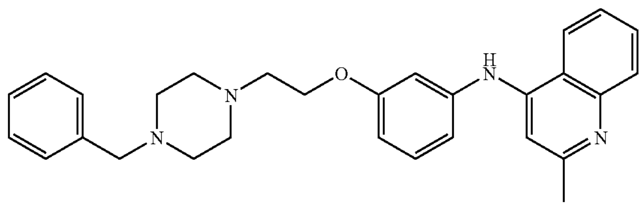 | {3-[2-(4-Benzylpiperazin-1-yl)ethoxy]phenyl}-(2-methylquinolin-4-yl)amine | yellow solid[b] | 453.29 |
| 27 | 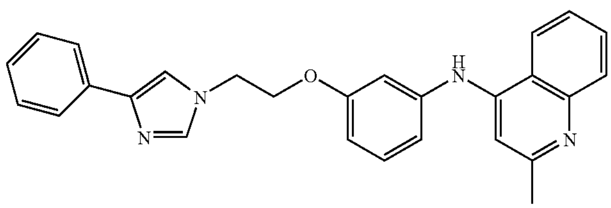 | (2-Methylquinolin-4-yl)-{3-[2-(4-phenylimidazol-1-yl)ethoxy]phenyl}amine | yellow solid | 420.32 |
| 28 | 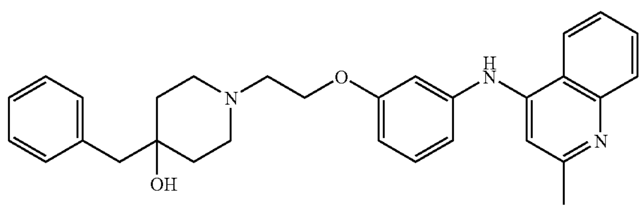 | 4-Benzyl-1-{2-[3-(2-methyl quinolin-4-ylamino)phenoxy]ethyl}piperidin-4-ol | yellow solid | 468.27 |
| 29 | 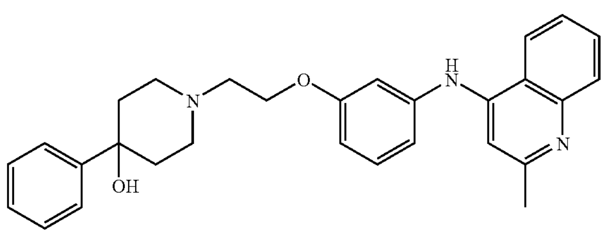 | 1-{2-[3-(2-Methylquinolin-4-yl amino)phenoxy]ethyl}-4-phenylpiperidin-4-ol | yellow solid | 454.23 |
| 30 | 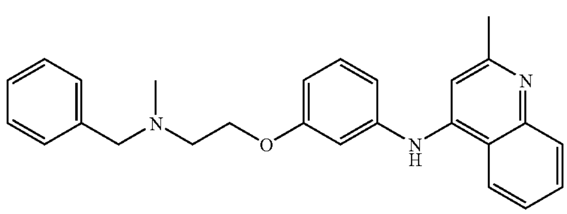 | {3-[2-(Benzylmethylamino)ethoxy]phenyl}-(2-methyl quinolin-4-yl)amine | yellow solid | 398.24 |
| 31 | 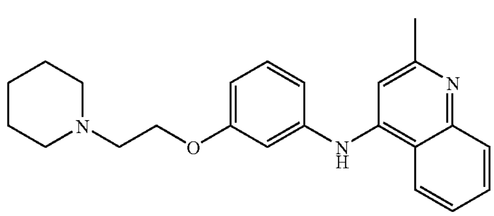 | (2-Methylquinolin-4-yl)-[3-(2-piperidin-1-yl ethoxy)phenyl]amine | yellow solid | 362.23 |

TABLE 2-continued

| Example | Structure | Chemical name | Physical description[a] | [M + H]+ |
|---|---|---|---|---|
| 32 | 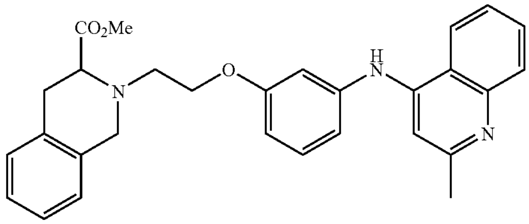 | Methyl 2-{2-[3-(2-methyl quinolin-4-ylamino)phenoxy] ethyl}-1,2,3,4-tetrahydro isoquinoline-3-carboxylate | white solid[b] | 468.23 |
| 33 | 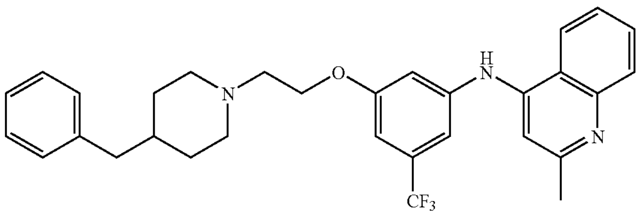 | {3-[2-(4-Benzylpiperidin-1-yl)ethoxy]-5-trifluoromethyl phenyl}-(2-methylquinolin-4-yl)amine | yellow solid | 520.25 |
| 34 | 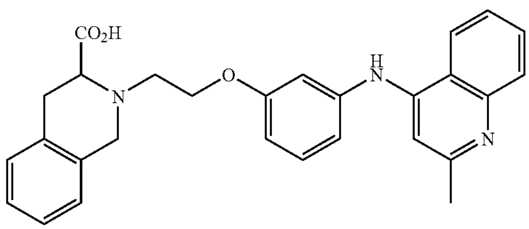 | 2-{2-[3-(2-Methylquinolin-4-yl amino)phenoxy]ethyl}-1,2,3,4-tetrahydroisoquinoline-3-carboxylic acid | yellow solid[e] | 454.22 |
| 35 | 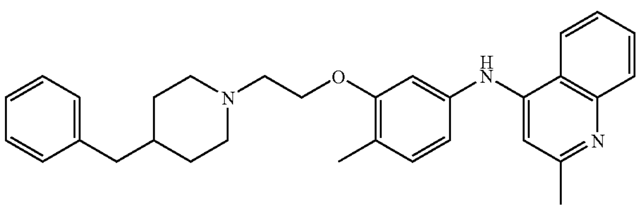 | {3-[2-(4-Benzylpiperidin-1-yl)ethoxy]-4-methyl]phenyl}-2-methylquinolin-4-yl)amine | yellow solid | 466.31 |
| 36 | 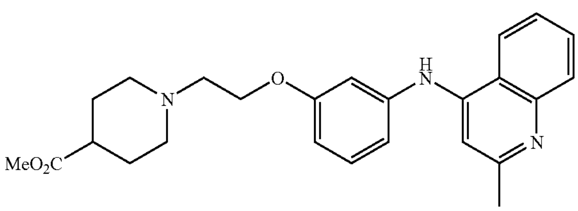 | Methyl 1-{2-[3-(2-methyl quinolin-4-ylamino)phenoxy]ethyl}piperidine-4-carboxylate | yellow solid | 420.26 |
| 37 | 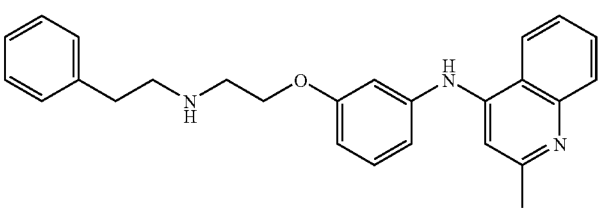 | (2-Methylquinolin-4-yl)-[3-(2-phenethylaminoethoxy)phenyl]amine | yellow solid[b] | 398.26 |
| 38 | 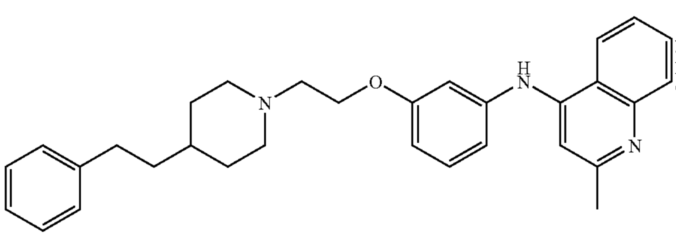 | (2-Methylquinolin-4-yl)-{3-[2-(4-phenethylpiperidin-1-yl)-ethoxy]phenyl}amine | yellow solid[b] | 467.29 |

TABLE 2-continued

| Example | Structure | Chemical name | Physical description[a] | [M + H]+ |
|---|---|---|---|---|
| 39 | 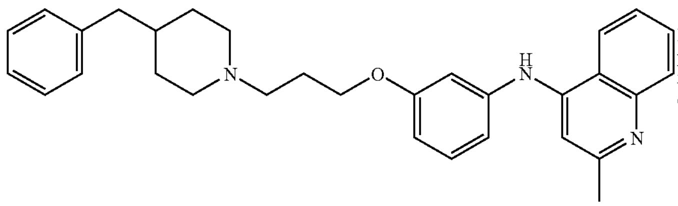 | {3-[3-(4-Benzylpiperidin-1-yl)propoxy]phenyl}-(2-methyl quinolin-4-yl)amine | yellow solid | 466.37 |
| 40 | 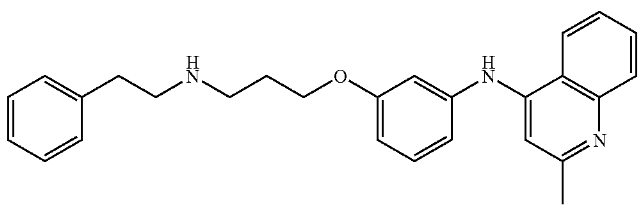 | (2-Methylquinolin-4-yl)-[3-(3-phenethylamino propoxy)phenyl]amine | yellow solid | 412.33 |
| 41 | 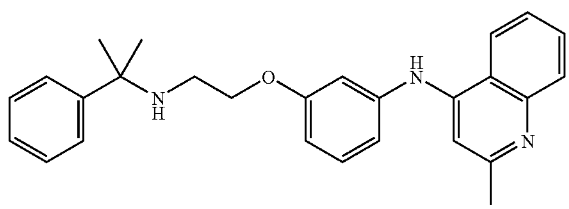 | {3-[2-(1-Methyl-1-phenyl ethyl-amino)ethoxy]phenyl}-(2-methylquinolin-4-yl)amine | yellow solid | 412.20 |
| 42 | 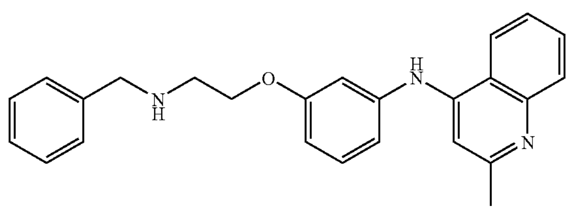 | [3-(2-Benzylaminoethoxy)phenyl]-(2-methyl quinolin-4-yl)amine | pale yellow solid | 384.25 |
| 43 | 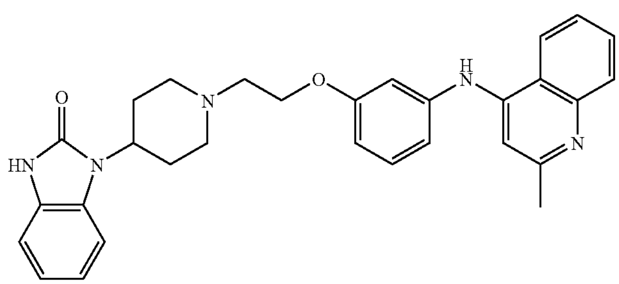 | 1-(1-{2-[3-(2-Methylquinolin-4-ylamino)phenoxy]ethyl}piperidin-4-yl)-1,3-dihydro benzoimidazol-2-one | pale yellow solid | 494.28 |
| 44 | 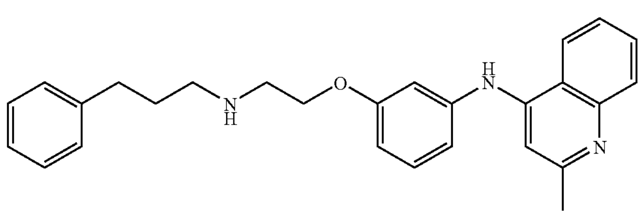 | (2-Methylquinolin-4-yl)-{3-[2-(3-phenylpropylamino)ethoxy]phenyl}amine | yellow solid[b] | 412.29 |
| 45 | 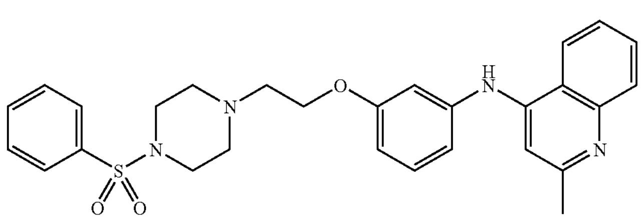 | {3-[2-(4-Benzenesulfonyl piperazin-1-yl)ethoxy]phenyl}-(2-methyl quinolin-4-yl)amine | yellow solid[b] | 503.34 |

TABLE 2-continued

| Example | Structure | Chemical name | Physical description[a] | [M + H]+ |
|---|---|---|---|---|
| 46 | 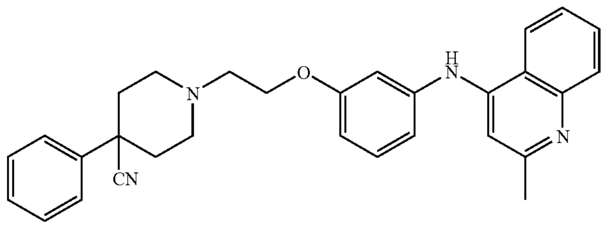 | 1-{2-[3-(2-Methylquinolin-4-yl amino)phenoxy]ethyl}-4-phenylpiperidine-4-carbonitrile | yellow solid | 463.32 |
| 47 | 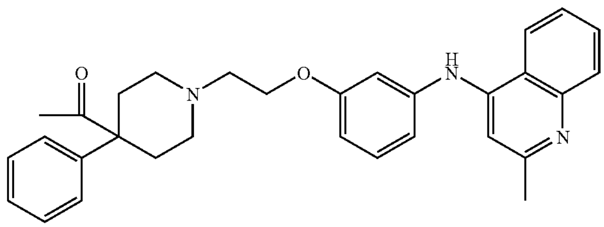 | 1-(1-{2-[3-(2-Methylquinolin-4-ylamino)phenoxy]ethyl}phenylpiperidin-4-yl)ethanone | yellow solid | 480.32 |
| 48 | 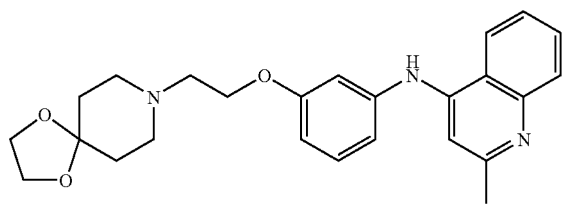 | {3-[2-(1,4-Dioxa-8-aza spiro[4.5]dec-8-phenyl}-(2-methyl quinolin-4-yl)amine | pale yellow solid[b] | 420.26 |
| 49 | 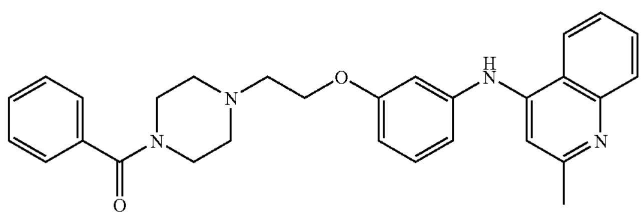 | 1-Benzoyl-4-{2-[3-(2-methyl quinolin-4-ylamino)phenoxy]ethyl}piperazine | yellow solid[b] | 467.33 |
| 50 | 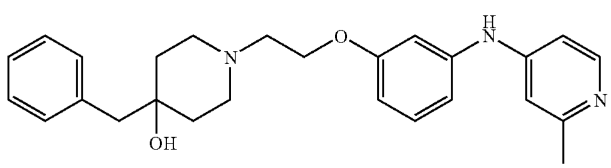 | 4-Benzyl-1-{2-[3-(2-methyl pyridin-4-ylamino)phenoxy]ethyl}piperidin-4-ol | white solid | 418.28 |
| 51 | 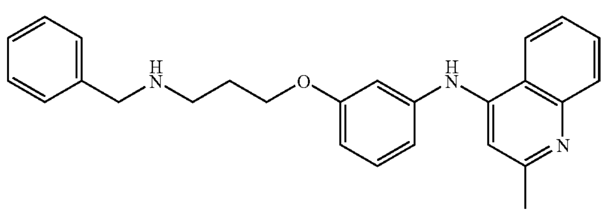 | [3-(3-Benzylaminopropoxy)phenyl]-(2-methyl quinolin-4-yl)amine | yellow solid | 398.26 |
| 52 | 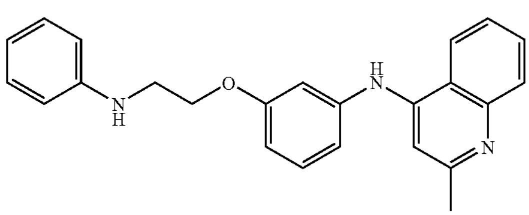 | (2-Methylquinolin-4-yl)-[3-(2-phenylaminoethoxy)phenyl]amine | yellow solid | 370.26 |

TABLE 2-continued

| Example | Structure | Chemical name | Physical description[a] | [M + H]+ |
|---|---|---|---|---|
| 53 | 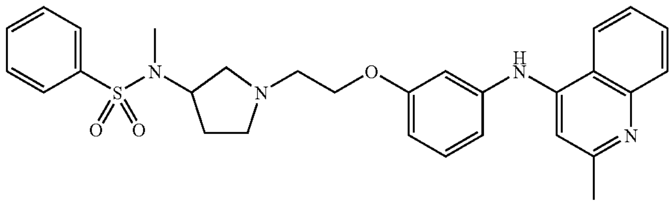 | N-Methyl-N-(1-{2-[3-(2-methyl quinolin-4-ylamino)phenoxy] ethyl}pyrrolidin-3-yl) benzenesulfonamide | pale yellow solid | 517.28 |
| 54 | 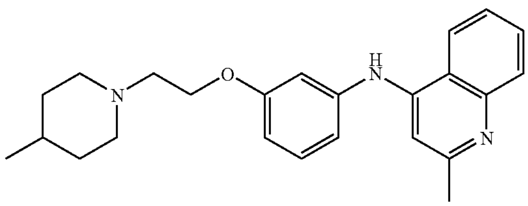 | {3-[2-(4-Methylpiperidin-1-yl) ethoxy]phenyl}-(2-methyl quinolin-4-yl)amine | pale yellow solid | 376.25 |
| 55 | 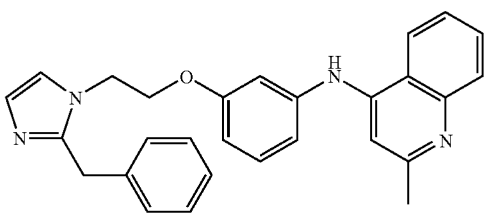 | {3-[2-(2-Benzylimidazol-1-yl) ethoxy]phenyl}-(2-methyl quinolin-4-yl)amine | off-white foam[b] | 435.29 |
| 56 | 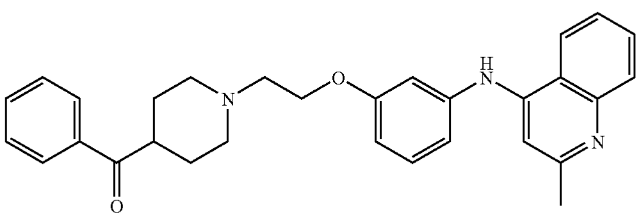 | (1-{2-[3-(2-Methylquinolin-4-yl amino)phenoxy]ethyl} piperidin-4-yl)phenylmethanone | off-white solid | 466.29 |
| 57 | 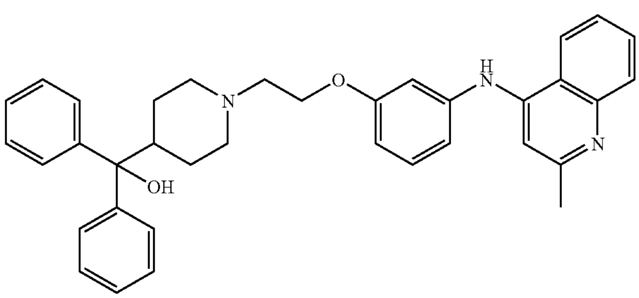 | (1-{2-[3-(2-Methylquinolin-4-yl amino)phen-oxy]ethyl}piperidin-4-yl)diphenylmethanol | yellow solid | 544.30 |
| 58 | 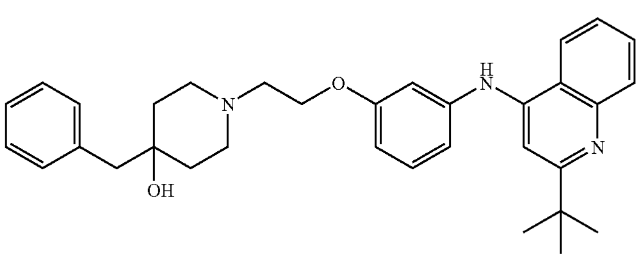 | 4-Benzyl-1-{2-[3-(2-tert-butyl quinolin-4-ylamino)phenoxy] ethyl}piperidin-4-ol | yellow solid | 510.39 |

TABLE 2-continued

| Example | Structure | Chemical name | Physical description[a] | [M + H]+ |
|---|---|---|---|---|
| 59 | 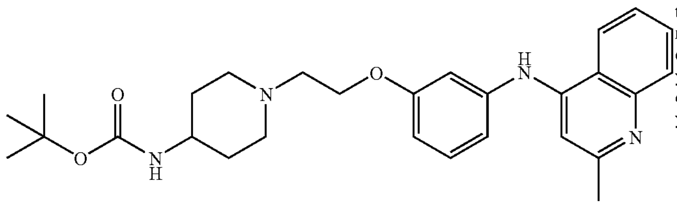 | tert-Butyl (1-{2-[3-(2-methyl quinolin-4-ylamino)phenoxy] ethyl}piperidin-4-yl)carbamate | pale yellow solid | 477.25 |
| 60 | 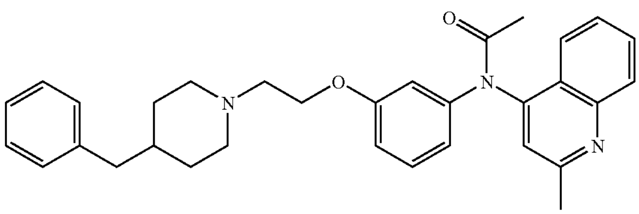 | N-{3-[2-(4-Benzylpiperidin-1-yl) ethoxy]phenyl}-N-(2-methyl quinolin-4-yl)acetamide | pale yellow solid[b] | 494.19 |
| 61 | 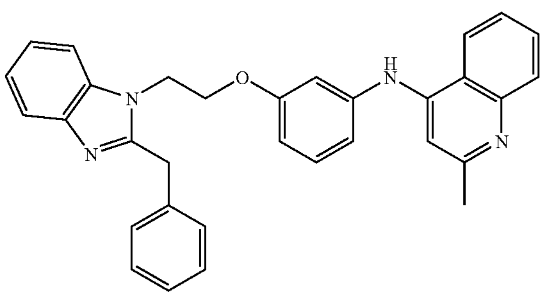 | {3-[2-(2-Benzylbenzo imidazol-1-yl)ethoxy]phenyl}-(2-methylquinolin-4-yl)amine | white solid | 485.29 |
| 62 | 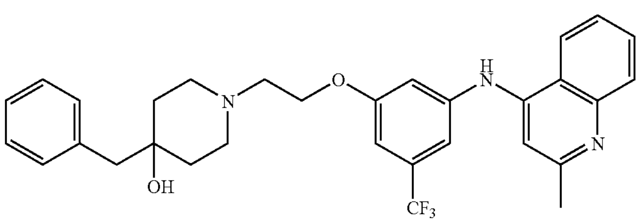 | 4-Benzyl-1-{2-[3-(2-methyl quinolin-4-ylamino)-5-trifluoromethylphenoxy] ethyl}piperidin-4-ol | yellow solid | 536.28 |
| 63 | 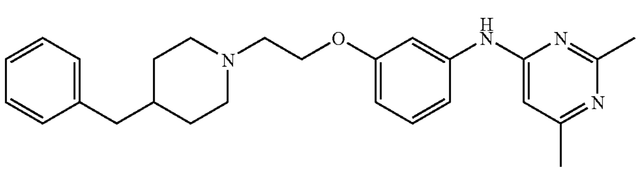 | {3-[2-(4-Benzylpiperidin-1-yl) ethoxy]phenyl}-(2,6-dimethyl pyrimidin-4-yl)amine | white solid[b] | 417.29 |
| 64 | 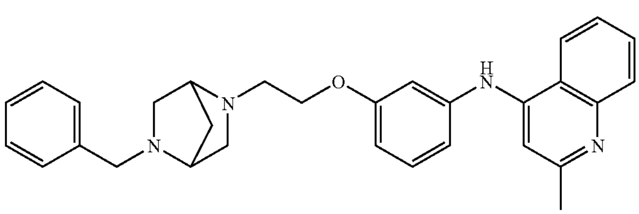 | {3-[2-(5-Benzyl-2,5-diaza bicyclo[2.2.1]hept-2-yl) ethoxy]phenyl}-(2-methyl quinolin-4-yl)amine | white amorphous solid[b] | 465.24 |

TABLE 2-continued

| Example | Structure | Chemical name | Physical description[a] | [M + H]+ |
|---|---|---|---|---|
| 65 | 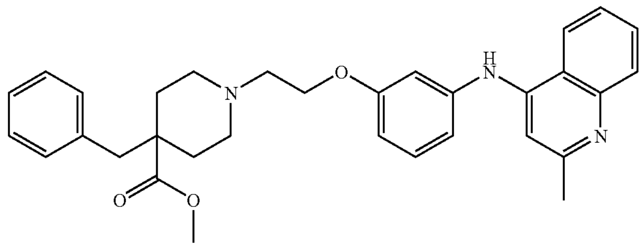 | Methyl 4-benzyl-1-{2-[3-(2-methylquinolin-4-ylamino)phenoxy]ethyl}piperidine-4-carboxylate | yellow powder | 510.25 |
| 66 | 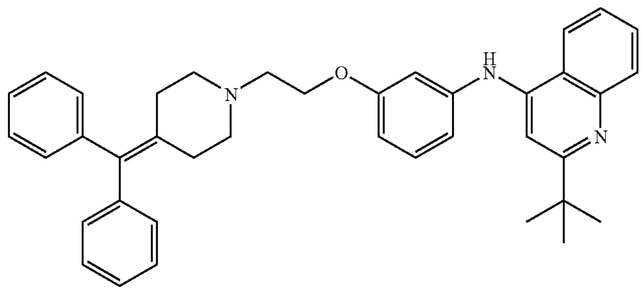 | {3-[2-(4-Benzhydrylidene piperidin-1-yl)ethoxy]phenyl}(2-tert-butylquinolin-4-yl)amine | yellow amorphous solid | 568.33 |
| 67 | 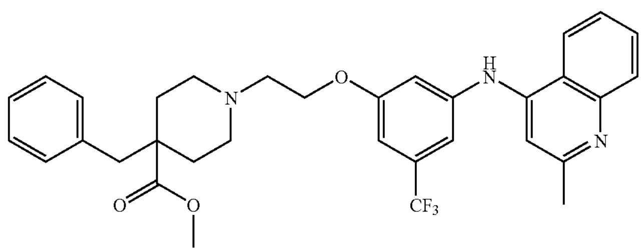 | Methyl 4-benzyl-1-{2-[3-(2-methylquinolin-4-ylamino)-5-trifluoro-methylphenoxy]ethyl}piperidine-4-carboxylate | pale yellow solid | 578.24 |
| 68 | 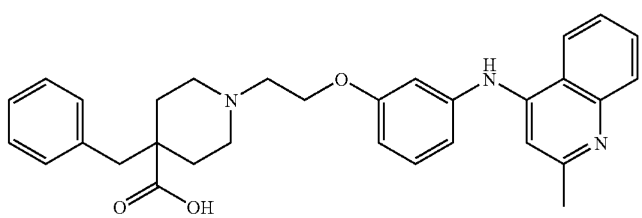 | 4-Benzyl-1-{2-[3-(2-methyl quinolin-4-ylamino)phenoxy]ethyl}piperidine-4-carboxylic acid | yellow powder | 496.25 |
| 69 | 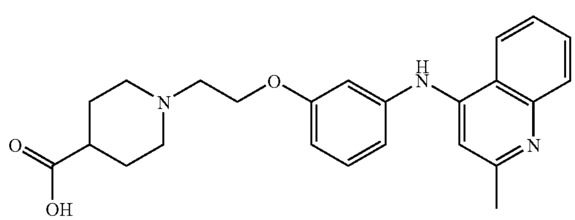 | 1-{2-[3-(2-Methylquinolin-4-yl amino)phenoxy]ethyl}piperidine-4-carboxylic acid | yellow solid[c] | 406.13 |
| 70 | 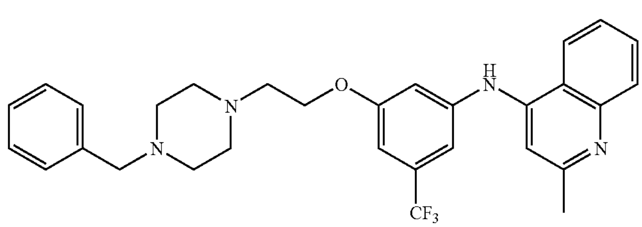 | {3-[2-(4-Benzylpiperazin-1-yl)ethoxy]-5-trifluoromethyl phenyl}-(2-methyl quinolin-4-yl)amine | yellow solid | 521.23 |

TABLE 2-continued

| Example | Structure | Chemical name | Physical description[a] | [M + H]+ |
|---|---|---|---|---|
| 71 | 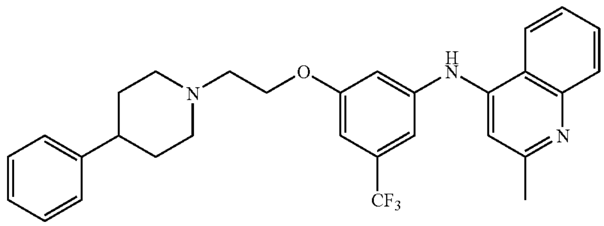 | (2-Methylquinolin-4-yl)-{3-[2-(4-phenylpiperidin-1-yl)ethoxy]-5-trifluoromethyl phenyl}amine | yellow solid | 506.23 |
| 72 | 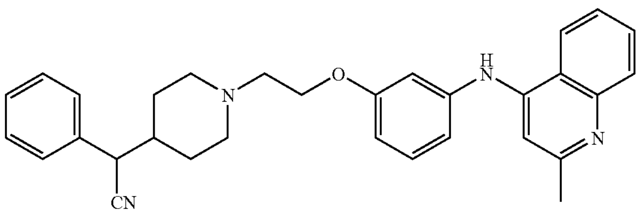 | (1-{2-[3-(2-Methylquinolin-4-yl amino)phenoxy]ethyl}piperidin-4-yl)phenyl acetonitrile | yellow solid | 477.30 |
| 73 | 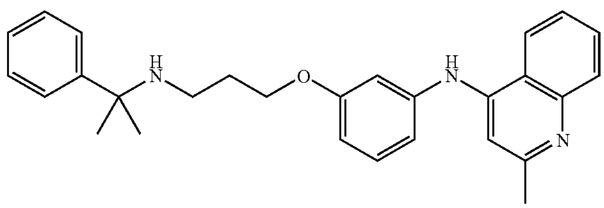 | {3-[3-(1-Methyl-1-phenyl ethylamino)propoxy]phenyl}-(2-methyl-quinolin-4-yl)amine | yellow solid | 426.15 |
| 74 | 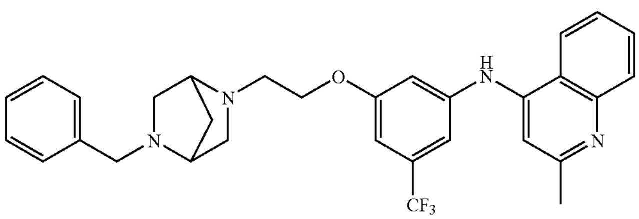 | {3-[2-(5-Benzyl-2,5-diaza bicyclo[2.2.1]hept-2-yl)ethoxy]-5-trifluoromethyl phenyl}-(2-methyl quinolin-4-yl)amine | yellow solid[f] | 533.26 |
| 75 | 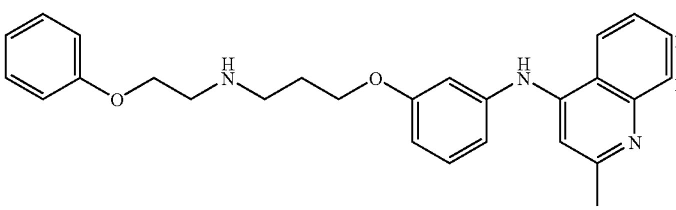 | (2-Methylquinolin-4-yl)-{3-[3-(2-phenoxyethylamino)propoxy]phenyl}amine | pale yellow solid | 428.27 |
| 76 | 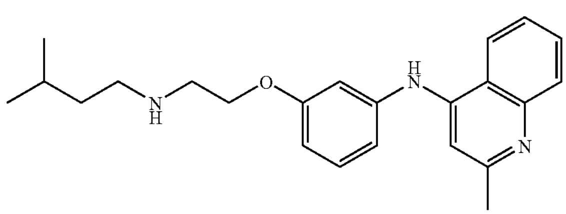 | {3-[2-(3-Methylbutylamino)ethoxy]phenyl}-(2-methyl quinolin-4-yl)amine | yellow oil[b] | 364.23 |

[a]DiHCl salt unless otherwise noted
[b]Parent
[c]+CO$_2$ compound
[e]sodium salt
[f]TriHCl salt The compound of Example 77 was synthesized by benzylation of the compound of Example 2 using a standard method (NaH/BnBr/DMF). The synthesis of Example 2 is the same as for Example 1 except that 3-nitrobenzoyl chloride was used instead of 3-nitrobenzenesulfonyl chloride.

The compounds of Examples 78 to 101 were synthesized in the same manner as the compound of Example 2.

The compound of Example 102 was synthesized by demethylation of the compound of Example 99 using a standard method ($BBr_3/CH_2Cl_2$).

The compound of Example 103 was synthesized in the same manner as the compound of Example 2.

The compound of Example 104 was synthesized in the same manner as the compound of Example 2 except that the last step was a standard coupling with 2,4-dimethoxybenzenesulfonyl chloride.

The compound of Example 105 was synthesized in the same manner as the compound of Example 2.

The structures, chemical names and physical descriptions for the compounds of Examples 77–173 are set forth in Table 3.

The compound of Example 106 was synthesized by demethylation of the compound of Example 103 using a standard method ($BBr_3/CH_2Cl_2$).

The compound of Example 107 was synthesized in the same manner as the compound of Example 2 using 2,4,6-trimethyl-3-nitrobenzoyl chloride instead of 3-nitrobenzoyl chloride. 2,4,6-Trimethyl-3-nitrobenzoyl chloride was synthesized by treatment of 2,4,6-trimethyl-3-nitrobenzoic acid (C Wu et al: J Med Chem 1999, 42:4485–4499) with $POCl_3$.

The compounds of Examples 108 and 109 were synthesized in the same manner as the compound of Example 2.

The preparation of the compound of Example 110 is shown.

The compound of Example 111 was synthesized in the same manner as the compound of Example 79 except that 2,3,4,5-tetrahydro-1H-benzo[c]azepine (A I Meyers, R H Hutchings: Tetrahedron 1993, 49:1807–1820) was used instead of 1,2,3,4-tetrahydro-isoquinoline.

The compound of Example 112 is shown.

The compound of Example 113 was synthesized in the same manner as the compound of Example 110.

The preparation of Example 114 is shown.

The compound of Example 115 was synthesized in a 3-step sequence: coupling of 36 with 2-amino-5-nitrobenzoic acid (EDCI/HOBT/DIPEA/DMF), then steps 4 and 5 of Example 45.

The compounds of Examples 116 to 118 were synthesized in the same manner as the compound of Example 2.

The compound of Example 119 was synthesized in the same manner as the compound of Example 79 except that 7-phenyl-1,2,3,4-tetrahydroisoquinoline was used instead of 1,2,3,4-tetrahydroisoquinoline. 7-Phenyl-1,2,3,4-tetrahydroisoquinoline was synthesized by a standard Suzuki coupling between phenylboronic acid and 7-bromo-1,2,3,4-tetrahydroisoquinoline (G E Stokker: Tetrahedron Lett 1996: 5453–5456).

The compound of Example 120 was synthesized in the same manner as the compound of Example 79 except that 7-fluoro-1,2,3,4-tetrahydroisoquinoline (G E Stokker: Tetrahedron Lett 1996:5453–5456) was used instead of 1,2,3,4-tetrahydroisoquinoline.

The compounds of Examples 121 to 122 were synthesized in the same manner as the compound of Example 120.

The compound of Example 123 was synthesized in the same manner as the compound of Example 2.

The compound of Example 124 was synthesized in the same manner as the compound of Example 120.

The compound of Example 125 was synthesized in the same manner as the compound of Example 79 except that the last step was a Buchwald coupling (Buchwald et al: Tetrahedron Lett 1995 36:3609) with 5-bromo-m-xylene instead of the acid catalyzed coupling with 5.

The compound of Example 126 was synthesized in the same manner as the compound of Example 2.

The compounds of Examples 127 and 128 were synthesized in the same manner as the compound of Example 120.

The compounds of Examples 129 and 130 were synthesized in the same manner as the compound of Example 2.

The compound of Example 131 was synthesized in the same manner as the compound of Example 120.

The compound of Examples 132 to 135 were synthesized in the same manner as the compound of Example 2.

The compound of Example 136 was synthesized in the same manner as the compound of Example 120.

The compounds of Examples 137 to 140 were synthesized in the same manner as the compounds of Example 2.

The compound of Example 141 was synthesized by a Buchwald coupling (Buchwald et al: Tetrahedron Lett 1995 36:3609) between 3-bromo-N-[2-(3,4-dihydro-1H-isoquinolin-2-yl)ethyl]benzamide and 4-amino-2-dimethylaminopyridine (Hnschberger A et al, Tetrahedron 2000, 56:1361–1367).

The compound of Example 142 was synthesized in the same manner as the compound of Example 125.

The compound of Example 143 was synthesized in the same manner as the compound of Example 2.

The preparation of Example 144 is shown.

The compounds of Examples 145 and 146 were synthesized in the same manner as the compound of Example 2.

The compound of Example 147 was synthesized in the same manner as the compound of Example 144.

The compound of Example 148 was synthesized in the same manner as the compound of Example 2.

The compound of Example 149 was synthesized in the same manner as the compound of Example 141.

The compound of Example 150 was synthesized in the same manner as the compound of Example 2.

The compound of Example 151 was synthesized in the same manner as the compound of Example 144.

The compound of Example 152 was synthesized by hydrolysis (1 eq $NaOH/THF/MeOH/H_2O$) of methyl 4-({2-[3-(2-methyl quinolin-4-ylamino)benzoylamino]ethylamino}-methyl)benzoate which was synthesized in the same manner as for Example 144.

The compound of Example 153 was synthesized in the same manner as the compound of Example 2.

The compound of Example 154 was synthesized by hydrolysis (1 eq $NaOH/THF/MeOH/H_2O$) of the compound of Example 151.

The compound of Example 155 was synthesized in the same manner as the compound of Example 141.

The compound of Example 156 was synthesized in the same manner as the compound of Example 2.

The compound of Example 157 was synthesized in the same manner as the compound of Example 151 and during the reductive amination step the lactam ring was formed.

The compound of Example 158 was synthesized in the same manner as the compound of Example 12 except that 2-bromo-2-methyl-N-(3-nitrobenzyl)propionamide and 40 were used instead of 3-nitrobenzyl bromide and dimethylamine, respectively. 2-Bromo-2-methyl-N-(3-nitrobenzyl)propionamide was synthesized by a standard coupling (HOBt/EDCI/DIPEA/DMF) of 2-bromo-2-methylpropionic acid and 3-nitroaniline.

The compounds of Examples 159 to 161 were synthesized in the same manner as the compound of Example 2.

The compounds of Examples 162 to 168 were synthesized in the same manner as the compound of Example 144.

The preparation of the compound of Example 169 is shown.

The compounds of Examples 170 to 173 were synthesized in the same manner as the compound of Example 144.

EXAMPLE 110

2-[2-(3,4-Dihydro-1H-isoquinolin-2-yl)ethyl]-4-(2-methylquinolin-4-ylamino)-2,3-dihydroisoindol-1-one

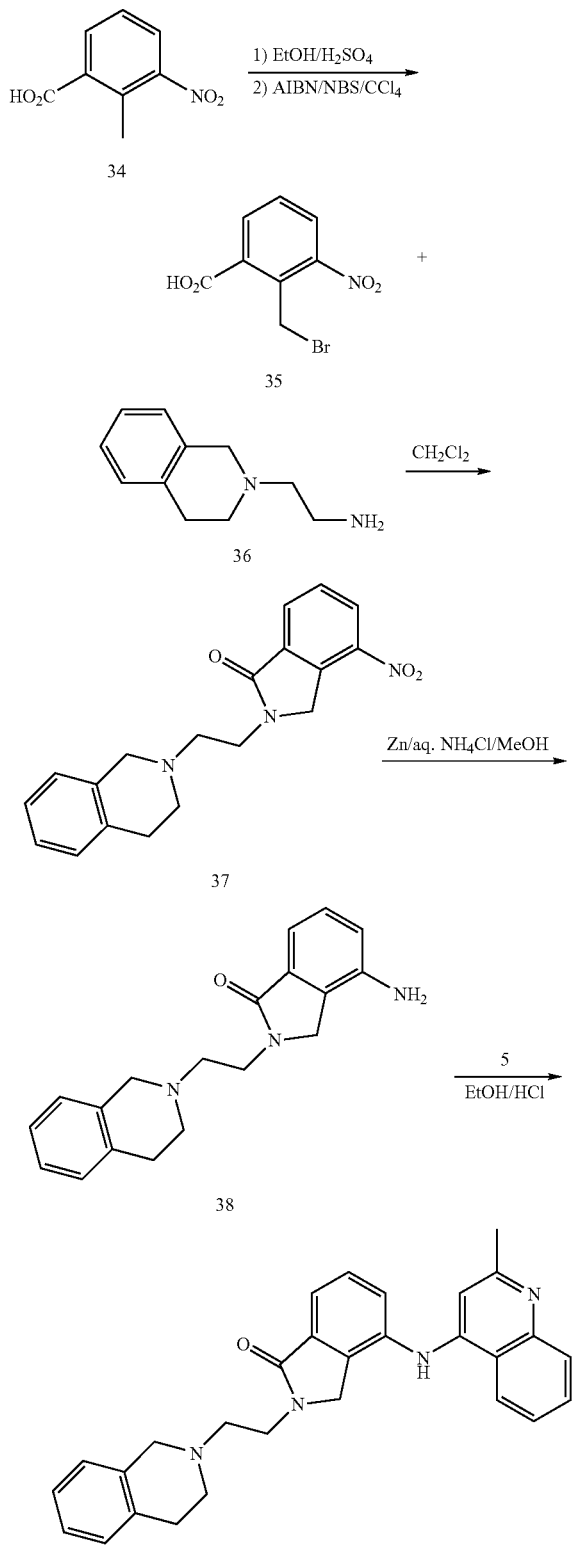

Example 110

Step 1. Ethyl 2-methyl-3-nitrobenzoate.

To a solution of 2-methyl-3-nitrobenzoic acid (34) (3.4 g, 18.8 mmol) in EtOH (60 mL) was added conc $H_2SO_4$ (1 mL) dropwise. The resulting solution was heated at 75° C. for 72 hours before the solvent was evaporated. The residue was basified with saturated aq. $NaHCO_3$ and extracted with EtOAc, washed with water, brine. The organic layer was dried over $MgSO_4$ and concentrated to give the desired ethyl ester (3.9 g, ~quantitative).

Step 2. Ethyl 2-bromomethyl-3-nitrobenzoate (35).

To a solution of ethyl 2-methyl-3-nitrobenzoate (3.9 g, 18.6 mmol) in $CCl_4$ (56 mL) were sequentially added AIBN (0.61 g, 20% mol) and NBS (3.5 g, 19.5 mmol). The mixture was heated at 80° C. for 72 hours before it was allowed to cool to room temperature. The resulting precipitate was filtered through a plug of silica gel, washed with dichloromethane, and the filtrate was concentrated to give a 1:1 mixture of 35 (3.1 g, 58%) and the starting material.

Step 3. 2-[2-(3,4-Dihydro-1H-isoquinolin-2-yl)ethyl]-4-nitro-2,3-dihydroisoindol-1-one (37).

To a solution of 2-(3,4-dihydro-1H-isoquinolin-2-yl)ethylamine (36) (0.36 g, 2.0 mmol) in dichloromethane (4 mL) was added the bromide 35 (0.75 g, 2.6 mmol) in dichloromethane (5 mL) at 0° C. The mixture was allowed to warm to room temperature and stirred for 16 hours before it was poured into saturated $NaHCO_3$ (aq. 50 mL) and extracted with dichloromethane (2×50 mL). The combined organic layers were washed with water (70 mL), brine (70 mL), dried over $MgSO_4$, and concentrated on a rotavap. The residue was chromatographed on silica gel eluting with 3:1 to 1:1 hexanes/EtOAc to give 37 (0.39 g, 57%).

Step 4. 4-Amino-2-[2-(3,4-dihydro-1H-isoquinolin-2-yl)ethyl]-2,3-dihydroisoindol-1-one (38).

To a solution of 37 (0.38 g, 1.1 mmol) in methanol (6 mL) was added a solution of ammonium chloride (0.13 g, 2.42 mmol) in water (1.5 mL). Zinc powder (0.49 g, 7.4 mmol) was then added portionwise and the resulting mixture was stirred for 2 hours. The solids were filtered and washed with methanol, the filtrate was basified with saturated sodium bicarbonate (aq.), and the resulting mixture was extracted with EtOAc. The organic layer was dried over $MgSO_4$ and concentrated to give 38 (0.31 g, 88%).

Step 5. 2-[2-(3,4-Dihydro-1H-isoquinolin-2-yl)ethyl]-4-(2-methylquinolin-4-ylamino)-2,3-dihydroisoindol-1-one.

The title compound was prepared from 38 by the procedure of Example 1 Step 3.

EXAMPLE 112

N-[2-(3,4-Dihydro-1H-isoquinolin-2-yl)-1,1-dimethylethyl]-3-(2-methylquinolin-4-ylamino)benzamide

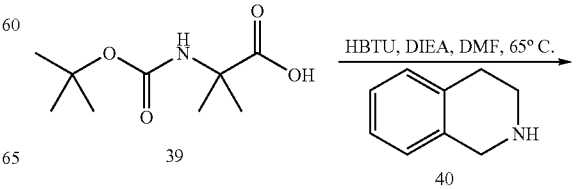

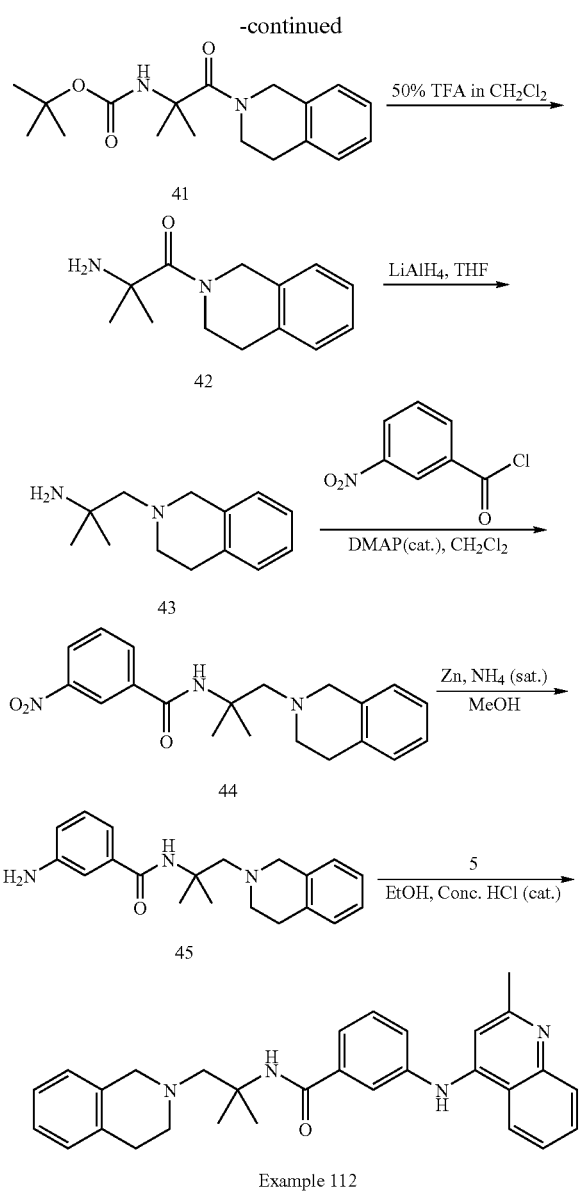

washings with 1 N NaOH (2×50 mL) and brine (50 mL), the organic solution was dried (Na$_2$SO$_4$) and concentrated to afford 42 (0.20 g, 77%).

Step 3. 2-(3,4-Dihydro-1H-isoquinolin-2-yl)-1,1-dimethyl-ethylamine (43).

To a solution of 42 (0.20 g, 0.91 mmol) in anhydrous THF (4 mL) at 0° C. was added LiAlH$_4$ (1.0 M in THF, 3.0 mL, 3.0 mmol). The resulting mixture was heated under reflux overnight before it was allowed to cool to room temperature. Excess LiAlH$_4$ was destroyed with slow addition of Na$_2$SO$_4$.10H$_2$O at 0° C. until gas evolution ceased. The solids were filtered off and the filtrate was concentrated to give 43 (0.14 g, 79%).

Step 4. N-[2-(3,4-Dihydro-1H-isoquinolin-2-yl)-1,1-dimethylethyl]-3-nitrobenzamide (44).

To a solution of 3-nitrobenzoylchloride (0.14 g, 0.75 mmol) and 43 (0.15 g, 0.76 mmol) in anhydrous CH$_2$Cl$_2$ (7 mL) was added DMAP (10 mg). The reaction was stirred at room temperature overnight before it was diluted with EtOAc (100 mL). Upon sequential washings with 1 N NaOH (2×100 mL), water (200 mL), the organic mixture was dried (Na$_2$SO$_4$) and concentrated under reduced pressure to give 44 (0.31 g,~100%) as a thick dark oil.

Step 5. 3-Amino-N-[2-(3,4-dihydro-1H-isoquinolin-2-yl)-1,1-dimethylethyl]benzamide (45).

45 was prepared from 44 by the procedure of Example 110 Step 4.

Step 6. N-[2-(3,4-Dihydro-1H-isoquinolin-2-yl)-1,1-dimethylethyl]-3-(2-methylquinolin-4-ylamino)benzamide.

The title compound was prepared from 45 by the procedure of Example 1 Step 3.

EXAMPLE 114

N-[2-(3,4-Dihydro-1H-isoquinolin-2-yl)-2-methylpropyl]-3-(2-methylquinolin-4-ylamino)benzamide Step 1. tert-Butyl [2-(3,4-dihydro-1H-isoquinolin-2-yl)-1,1-dimethyl-2-oxoethyl]carbamate (41).

To a solution of 39 (0.28 g, 1.38 mmol), 1,2,3,4-tetrahydroisoquinoline (40) (0.18 g, 1.38 mmol) and diisopropylethylamine (0.50 g, 3.85 mmol) in anhydrous DMF (5 mL) was added HBTU (0.72 g, 1.90 mmol). The mixture was heated at 65° C. overnight before it was allowed to cool to room temperature, and diluted with EtOAc (100 mL). The resulting solution was sequentially washed with 1N HCl (2×100 mL), 1N NaOH (2×100 mL) and brine (100 mL). The residue after drying (Na$_2$SO$_4$) and concentration of the organic layer was purified on silica gel column to give 41 (0.36 g, 82%).

Step 2. 2-Amino-1-(3,4-dihydro-1H-isoquinolin-2-yl)-2-methylpropan-1-one (42).

A solution of 41 (0.36 g, 1.1 mmol) in TFA (5 mL) and CH$_2$Cl$_2$ (5 mL) was stirred at room temperature for 40 minutes. The mixture was concentrated in vacuo and the residue was dissolved in EtOAc (50 mL). Upon sequential -continued

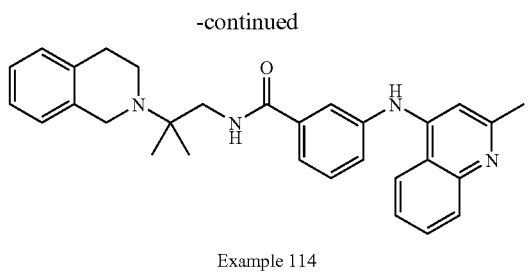

Example 114

Step 1. (3,4-Dihydro-1H-isoquinolin-2-yl)acetonitrile (46).

46 was prepared from 40 by the procedure of Example 13 Step 2.

Step 2. 2-(3,4-Dihydro-1H-isoquinolin-2-yl)-2-methylpropionitrile (47).

To a solution of 46 (1.27 g, 7.38 mmol) in anhydrous THF (20 mL) was slowly added LDA (2.0 M in THF, 8.1 mL, 16.2 mmol) at −78° C. The resulting mixture was stirred at −78° C. for 30 minutes before the addition of iodomethane (4.20 g, 29.6 mmol). The cold bath was removed and the reaction was allowed to warm up to room temperature and stirred overnight. To work up, the mixture was diluted with EtOAc (150 mL), the resulting solution washed with 1 N NaOH (2×100 mL) and brine (100 mL). The organic layer was dried ($Na_2SO_4$), concentrated, and the residue purified on a silica gel column to afford 47 (0.38 g, 26%).

Step 3. 2-(3,4-Dihydro-1H-isoquinolin-2-yl)-2-methylpropylamine (48).

48 was prepared from 47 by the procedure of Example 112 Step 3.

Step 4. N-[2-(3,4-Dihydro-1H-isoquinolin-2-yl)-2-methylpropyl]-3-(2-methylquinolin-4-ylamino)benzamide.

48 and 49 were reacted in the presence of $AlMe_3$ and $ClCH_2CH_2Cl$ at 80° by the procedure of Lipton, M F; Basha, A; Weinreb, M: *Organic Syntheses,* 1988, 6, 492–495.

EXAMPLE 144

N-(2-Benzylaminoethyl)-3-(2-methylquinolin-4-ylamino)benzamide

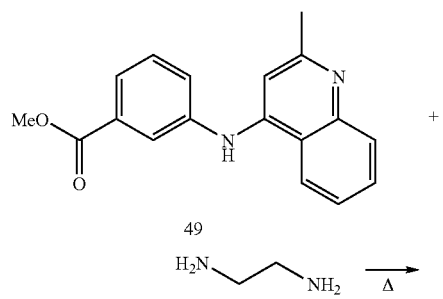

49

-continued

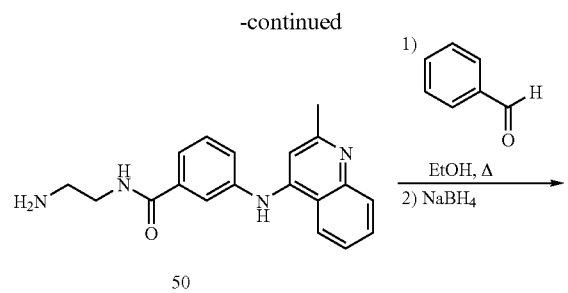

50

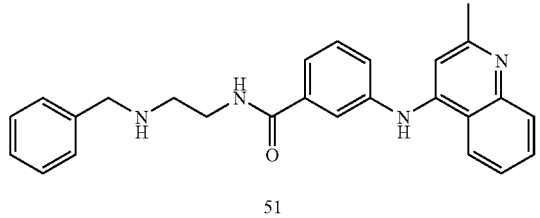

51

Step 1. N-(2-Aminoethyl)-3-(2-methylquinolin-4-ylamino)benzamide (50).

A mixture of methyl ester 49 (2.0 g, 6.8 mmol) and ethylenediamine (30 mL) was heated at 110° C. for 2 hours before it was poured into ice water (300 mL). The precipitate was filtered and dried under high vaccum to give 50 (2.0 g, 91%) as an off-white solid, which was used without further purification.

Step 2. N-(2-Benzylaminoethyl)-3-(2-methylquinolin-4-ylamino)benzamide.

A solution of amine 50 (0.22 g, 0.68 mmol) and benzyaldehyde (0.07 mL, 0.08 mmol) in EtOH (3.0 mL) was heated at reflux overnight before it was allowed to cool to room temperature. Sodium borohydride (0.04 g, 0.80 mmol) was added and the reaction was stirred at room temperature for 1 hour. The mixture was mixed with 2N NaOH (3.0 mL), brine (2.0 mL), and extracted with 7:3 $CH_2Cl_2$/MeOH (3×5.0 mL). The combined organic layers were dried ($K_2CO_3$) and concentrated under reduced pressure. The residue was purified by flash chromatography ($SiO_2$, gradient elution, 3:1 hexanes/EtOAc to 7:3 $CH_2Cl_2$/MeOH) to yield the desired product (0.15 g, 62%) as a pale yellow solid.

EXAMPLE 169

3-(2-Methylquinolin-4-ylamino)-N-[2-(4-phenyl-3,4-dihydro-1H-isoquinolin-2-yl)ethyl]benzamide.

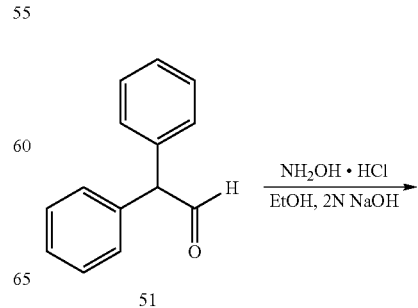

51

-continued

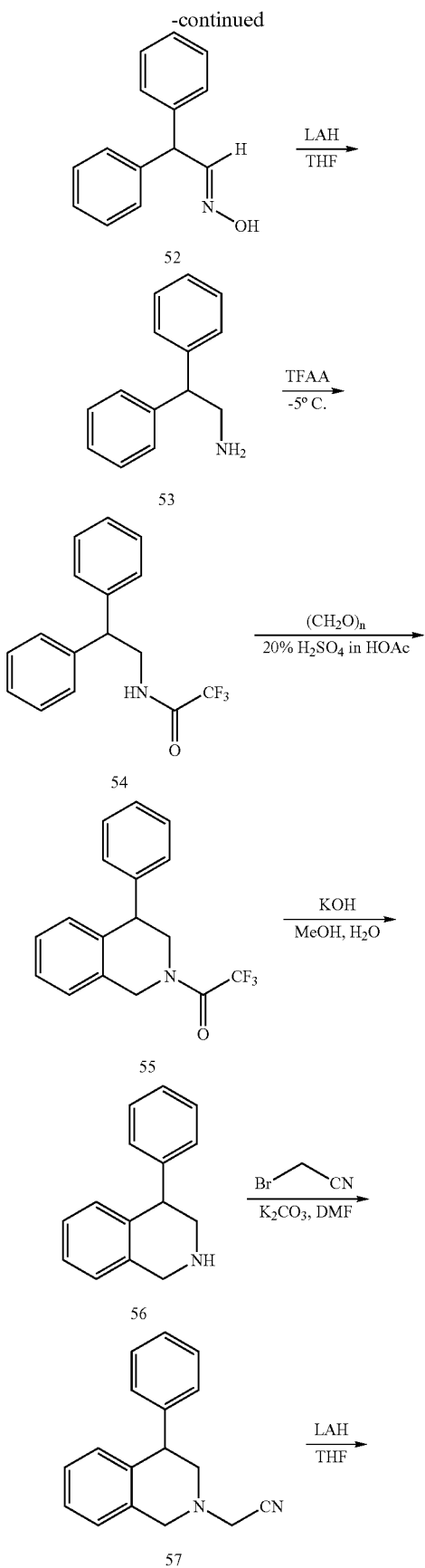

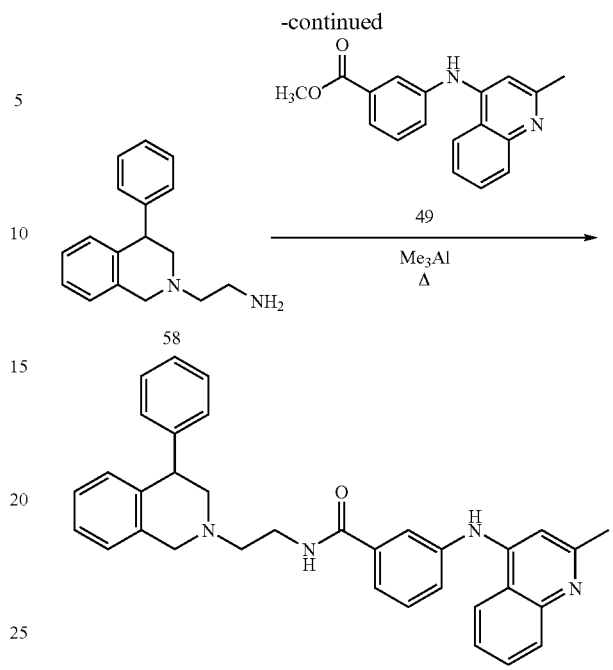

Example 169

Step 1. Diphenylacetaldehyde oxime (52).

To a solution of diphenylacetaldehyde (51) (4.0 g, 20.3 mmol) in EtOH (50 mL) were sequentially added hydroxylamine hydrochloride (1.41 g, 20.3 mmol) and 2 N NaOH (aq. 5 mL). The reaction was stirred at room temperature overnight followed by removal of EtOH under reduced pressure. The residue was washed with water (50 mL) and extracted with EtOAc (3×50 mL). The combined organic layers were dried (MgSO$_4$) and concentrated under reduced pressure to give 52 (4.0 g, 93%).

Step 2. 2,2-Diphenylethylamine (53).

To a solution of oxime 52 (4.0 g, 18.9 mmol) in THF (50 mL) was added LiAlH$_4$ (1.0 M solution in THF, 28.3 mL, 28.3 mmol) at 0° C. and the mixture was stirred at room temperature for 4 hours. Sodium sulfate decahydrate was added and the reaction was stirred for an additional hour. The solids were filtered and the filtrate was concentrated under reduced pressure to give 53 (3.14 g, 84%) as a yellow oil.

Step 3. N-(2,2-Diphenylethyl)-2,2,2-trifluoroacetamide (54).

To neat TFAA (14.9 g, 63.6 mmol) at −5° C. was added amine 53 (3.14 g, 15.9 mmol) dropwise over a 10 minute period and the resulting mixture was stirred for 2 hours. The crude mixture was poured into ice water and extracted with ethyl acetate (3×60 mL). The combined organic layers were dried (MgSO$_4$) and concentrated under reduced pressure. Purification by recrystallization (hexanes/ethyl acetate) provided 54 (1.5 g, 32%) as a yellow solid.

Step 4. 4-Pheny-1-trifluoroacetyl-3,4-dihydro-1H-isoquinoline (55).

Compound 54 (1.5 g, 5.11 mmol) and paraformaldehyde (1.2 g, 7.67 mmol) were added in small portions simultaneously to a solution of H$_2$SO$_4$ (4 mL) in HOAc (16 mL).

The reaction mixture was stirred for 12 hours and then poured into ice water. The aqueous mixture was extracted with ethyl acetate (3×50 mL) and the combined organic layers were dried (MgSO$_4$) and concentrated under reduced pressure to yield 55 (1.0 g, 66%) a yellow solid.

Step 5. 4-Phenyl-1,2,3,4-tetrahydroisoquinoline (56).

To a solution of 55 (0.9 g, 2.94 mmol) in MeOH (10 mL) were added water (2 mL), KOH (0.33 g, 5.89 mmol), and the reaction was stirred at room temperature for 12 hours. The mixture was washed with a saturated sodium chloride solution and extracted with 7:3 CH$_2$Cl$_2$/MeOH (3×10 mL). The combined organic layers were dried (K$_2$CO$_3$) and concentrated under reduced pressure to give 56 (0.70 g.~100%) as a yellow oil.

Step 6. (4-Phenyl-3,4-dihydro-1H-isoquinolin-2-yl)acetonitrile (57).

57 was prepared from 56 by the procedure of Example 13 Step 2.

Step 7. 2-(4-Phenyl-3,4-dihydro-1H-isoquinolin-2-yl)ethylamine (58).

58 was prepared from 57 by the procedure of Example 112 Step 3.

Step 8. 3-(2-Methylquinolin-4-ylamino)-N-[2-(4-phenyl-3,4-dihydro-1H-isoquinolin-2-yl)ethyl]benzamide.

The title compound was prepared by reacting 58 with 49 by the procedure of Lipton, M F; Basha, A; Weinreb, M: *Organic Syntheses*, 1988, 6, 492–495.

TABLE 3

| Example | Structure | Chemical Name | Physical Description[a] | [M + H]$^+$ |
|---|---|---|---|---|
| 77 | 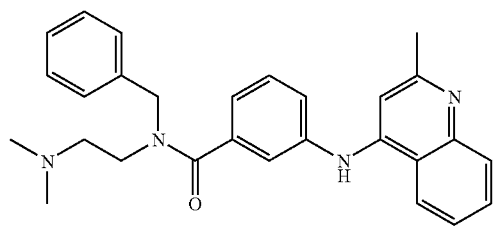 | N-Benzyl-N-(2-dimethyl aminoethyl)-3-(2-methylquinolin-4-yl amino)-benzamide | yellow solid[b] | 439.28 |
| 78 | 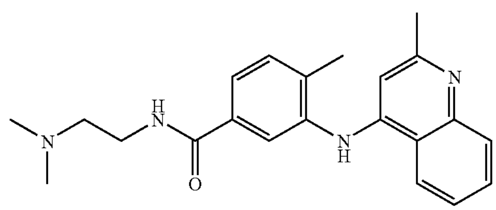 | N-(2-Dimethyl-aminoethyl)-4-methyl-3-(2-methylquinolin-4-yl amino)benzamide | Light yellow solid[d] | 363.32 |
| 79 | 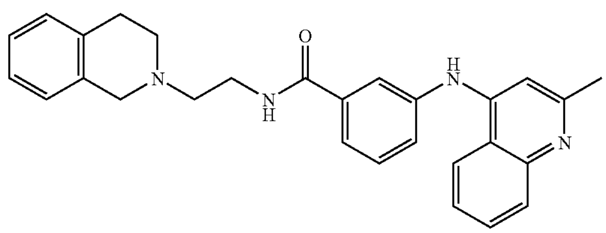 | N-[2-(3,4-Dihydro-1H-iso quinolin-2-yl)ethyl]-3-(2-methyl quinolin-4-ylamino)benzamide | Light yellow solid | 437.22 |
| 80 | 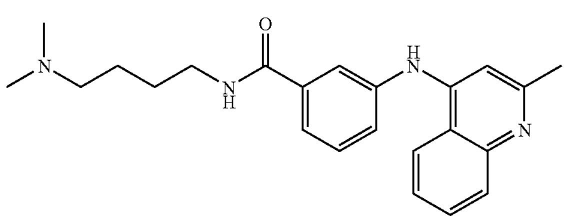 | N-(4-Dimethlaminobutyl)-3-(2-methylquinolin-4-ylamino) benzamide | yellowish solid[b] | 377.26 |
| 81 | 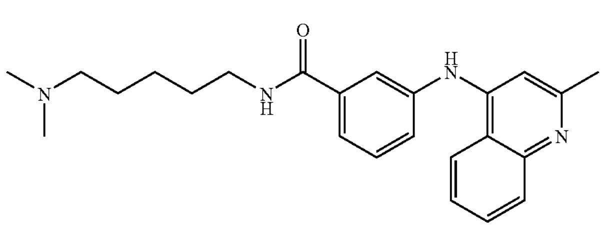 | N-(5-Dimethyl-aminopentyl)-3-(2-methylquinolin-4-ylamino)benzamide | yellow oil[b] | 391.28 |

TABLE 3-continued

| Example | Structure | Chemical Name | Physical Description[a] | [M + H]+ |
|---|---|---|---|---|
| 82 | 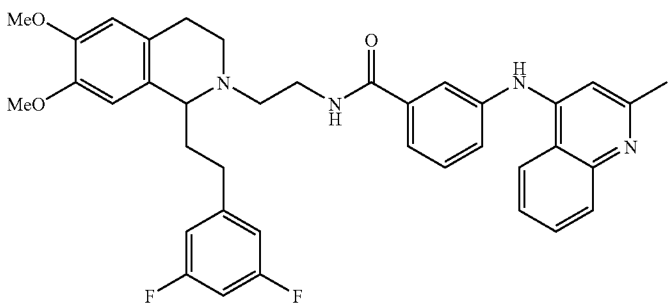 | N-(2-{1-[2-(3,5-Difluorophenyl)ethyl]-6,7-dimethoxy-3,4-dihydro-1H-isoquinolin-2-yl}ethyl)-3-(2-methyl quinolin-4-ylamino)benzamide | off-white solid[b] | 637.31 |
| 83 | 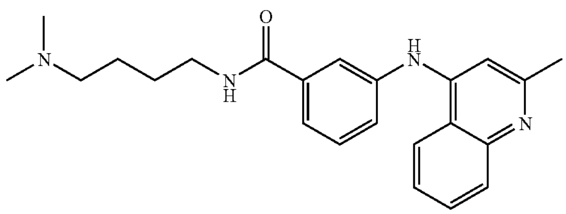 | N-(3-Dimethylaminopropyl)-3-(2-methylquinolin-4-ylamino)benzamide | yellow solid | 363.31 |
| 84 | 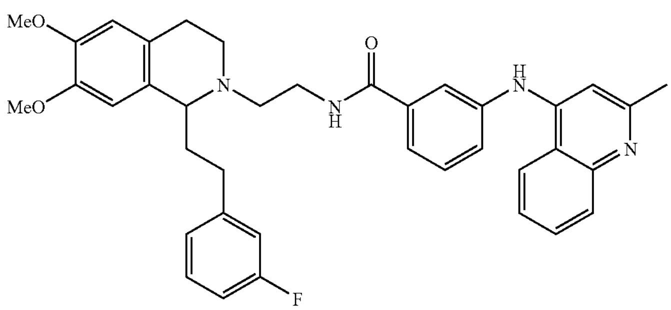 | N-(2-{1-[2-(3-Fluorophenyl)ethyl]-6,7-dimethoxy-3,4-dihydro-1H-isoquinolin-2-yl}ethyl)-3-(2-methyl quinolin-4-ylamino)benzamide | white solid[d] | 619.38 |
| 85 | 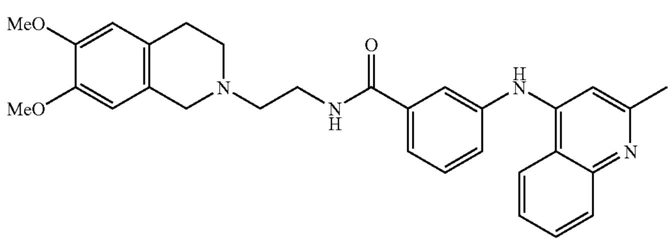 | N-[2-(6,7-Dimethoxy-3,4-dihydro-1H-isoquinolin-2-yl)ethyl]-3-(2-methylquinolin-4-ylamino)benzamide | yellow foam[b] | 497.34 |
| 86 | 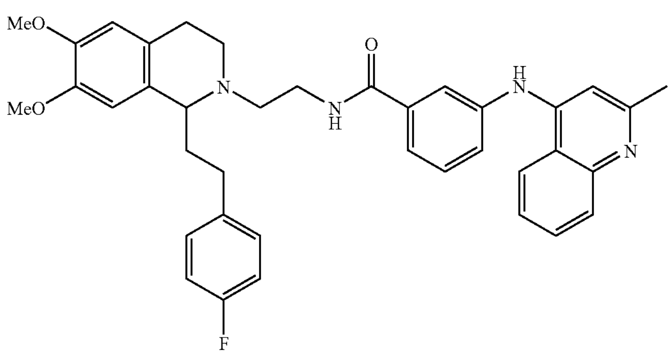 | N-(2-{1-[2-(4-Fluorophenyl)ethyl]-6,7-dimethoxy-3,4-dihydro-1H-isoquinolin-2-yl}ethyl)-3-(2-methyl quinolin-4-ylamino)benzamide | yellow solid | 619.37 |

TABLE 3-continued

| Example | Structure | Chemical Name | Physical Description[a] | [M + H]+ |
|---|---|---|---|---|
| 87 | 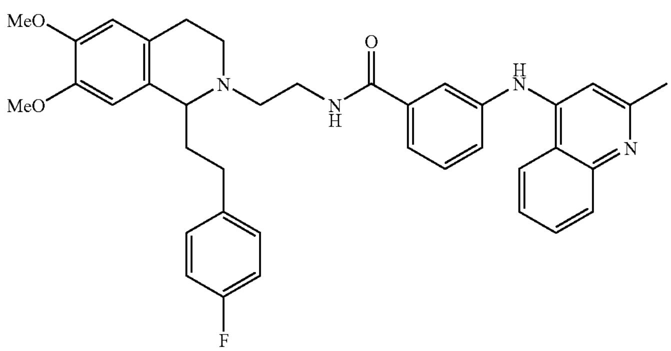 | 3-(2-Methylquinolin-4-ylamino)-N-(2-piperidin-1-yl-ethyl)benzamide | yellowish solid | 389.32 |
| 88 | 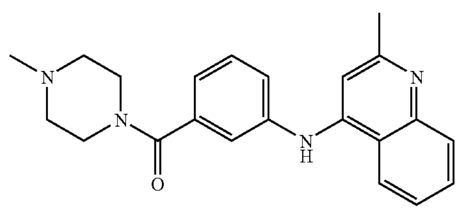 | 1-Methyl-4-[3-(2-methylquinolin-4-yl amino)benzoyl]piperazine | yellow solid | 361.32 |
| 89 | 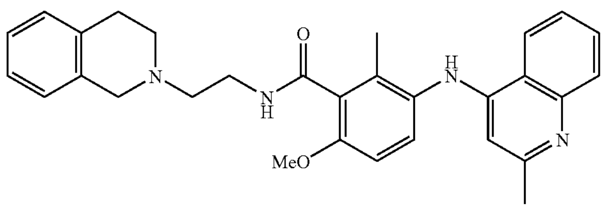 | N-(1-Benzylpiperidin-4-yl)-3-(2-methylquinolin-4-ylamino)benzamide | yellow solid | 451.41 |
| 90 | 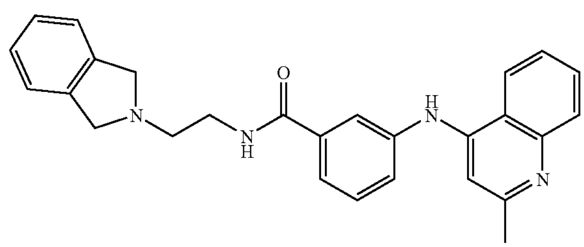 | N-[2-(1,3-Dihydroisoindol-2-yl)ethyl]-3-(2-methylquinolin-4-yl amino)benzamide | off-white solid | 423.35 |
| 91 | 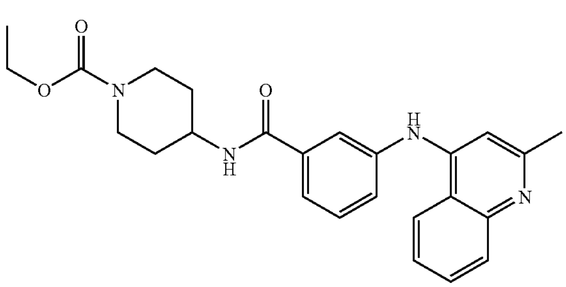 | Ethyl 4-[3-(2-methylquinolin-4-yl amino)benzoylamino]piperidine-1-carboxylate | yellow solod | 433.40 |

TABLE 3-continued

| Example | Structure | Chemical Name | Physical Description[a] | [M + H]+ |
|---|---|---|---|---|
| 92 | 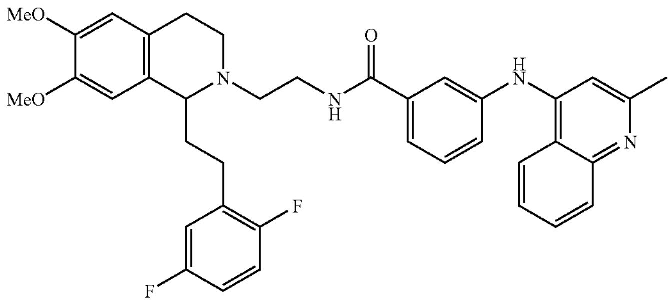 | N-(2-{1-[2-(2,5-Difluorophenyl)ethyl]-6,7-dimethoxy-3,4-dihydro-1H-isoquinolin-2-yl}ethyl)-3-(2-methylquinolin-4-ylamino)benzamide | white solid | 637.39 |
| 93 | 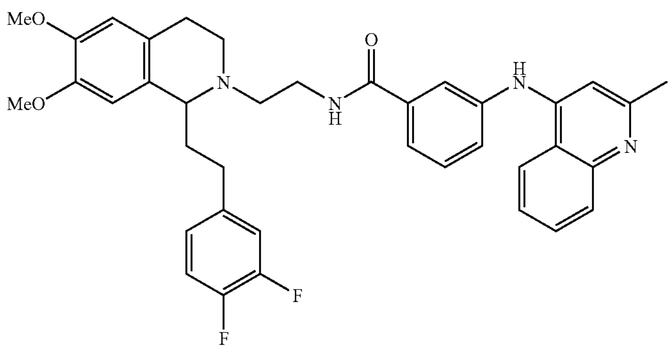 | N-(2-{1-[2-(3,4-Difluorophenyl)ethyl]-6,7-dimethoxy-3,4-dihydro-1H-isoquinolin-2-yl}ethyl)-3-(2-methylquinolin-4-ylamino)benzamide | yellow solid | 637.33 |
| 94 | 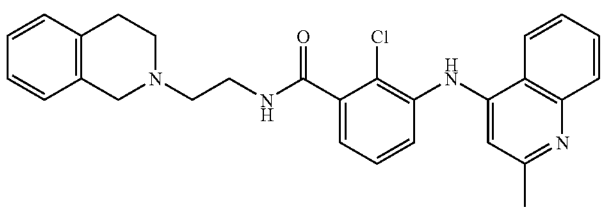 | 2-Chloro-N-[2-(3,4-dihydro-1H-isoquinolin-2-yl)ethyl]-3-(2-methyl-quinolin-4-ylamino)benzamide | white solid | 471.29 |
| 95 | 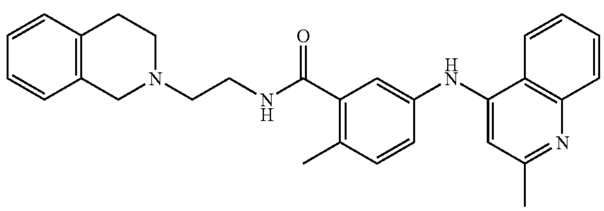 | N-[2-(3,4-Dihydro-1H-isoquinolin-2-yl)ethyl]-2-methyl-5-(2-methyl quinolin-4-ylamino)benzamide | white solid | 451.37 |
| 96 | 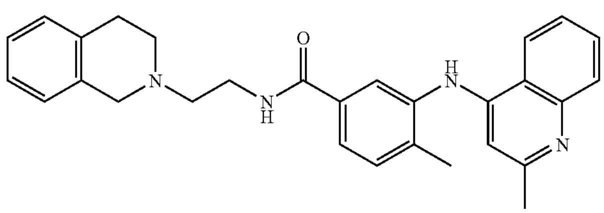 | N-[2-(3,4-Dihydro-1H-isoquinolin-2-yl)ethyl]-4-methyl-3-(2-methyl quinolin-4-ylamino)benzamide | off-white solid | 451.34 |
| 97 | 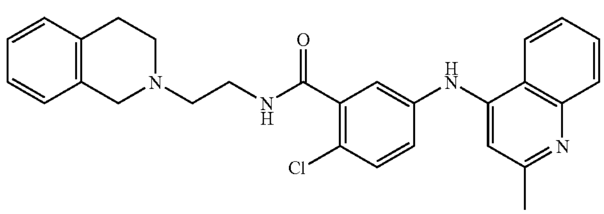 | 2-Chloro-N-[2-(3,4-dihydro-1H-isoquinolin-2-yl)ethyl]-5-(2-methyl quinolin-4-ylamino)benzamide | yellow solid | 471.38 |

TABLE 3-continued

| Example | Structure | Chemical Name | Physical Description[a] | [M + H]+ |
|---|---|---|---|---|
| 98 | 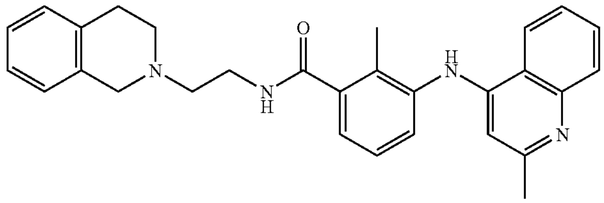 | N-[2-(3,4-Dihydro-1H-isoquinolin-2-yl)ethyl]-2-methyl-3-(2-methyl quinolin-4-ylamino)benzamide | yellowish solid | 451.25 |
| 99 | 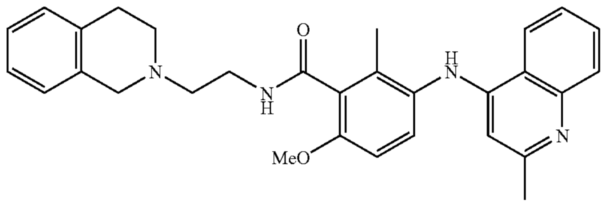 | N-[2-(3,4-Dihydro-1H-isoquinolin-2-yl)ethyl]-2-methoxy-5-(2-methyl quinolin-4-ylamino)benzamide | yellow solid | 467.33 |
| 100 | 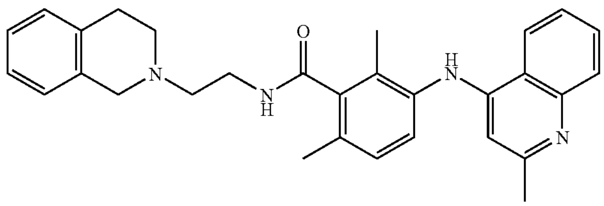 | N-[2-(3,4-Dihydro-1H-isoquinolin-2-yl)ethyl]-2,6-dimethyl-3-(2-methyl quinolin-4-ylamino)benzamide | white solid | 465.37 |
| 101 | 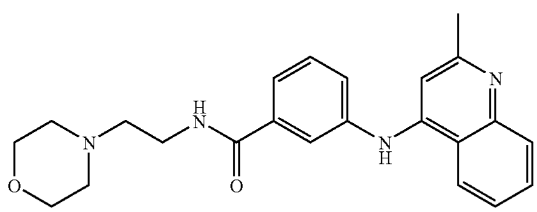 | 3-(2-Methylquinolin-4-ylamino)-N-(2-morpholin-4-ylethyl)benzamide | yellow solid[b] | 391.32 |
| 102 | 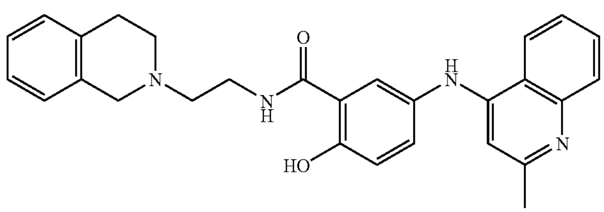 | N-[2-(3,4-Dihydro-1H-isoquinolin-2-yl)ethyl]-2-hydroxy-5-(2-methyl quinolin-4-ylamino)benzamide | yellow solid | 453.29 |
| 103 | 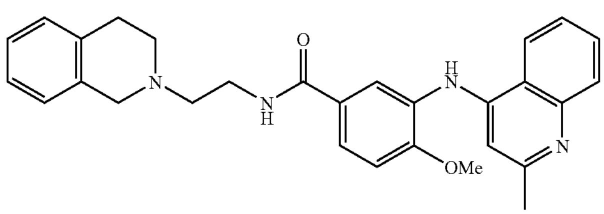 | N-[2-(3,4-Dihydro-1H-isoquinolin-2-yl)ethyl]-4-methoxy-3-(2-methyl quinolin-4-ylamino)benzamide | yellow solid | 467.34 |
| 104 | 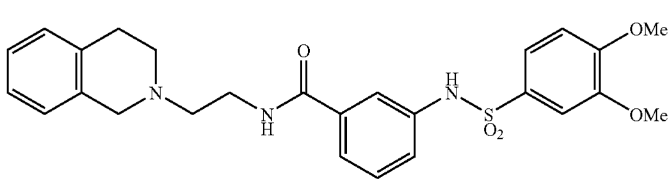 | N-[2-(3,4-Dihydro-1H-isoquinolin-2-yl)ethyl]-3-(3,4-dimethoxy benzenesulfonyl-amino)benzamide | off-white solid[b] | 496.26 |

TABLE 3-continued

| Example | Structure | Chemical Name | Physical Description[a] | [M + H]+ |
|---|---|---|---|---|
| 105 | 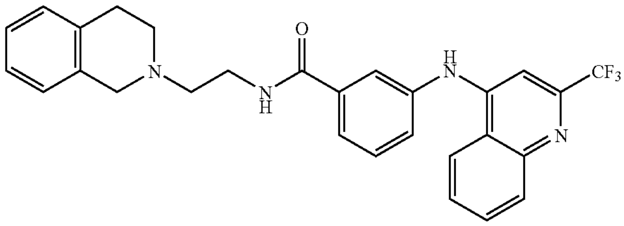 | N-[2-(3,4-Dihydro-1H-isoquinolin-2-yl)ethyl]-3-(2-trifluoromethyl quinolin-4-ylamino)benzamide | yellow solid | 491.22 |
| 106 | 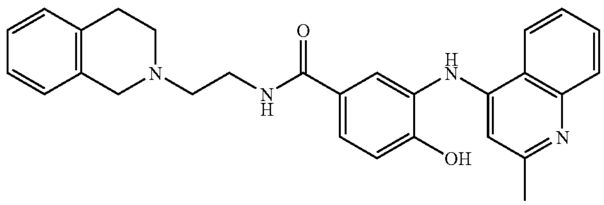 | N-[2-(3,4-Dihydro-1H-isoquinolin-2-yl)ethyl]-4-hydroxy-3-(2-methyl quinolin-4-ylamino)benzamide | yellow solid | 453.20 |
| 107 | 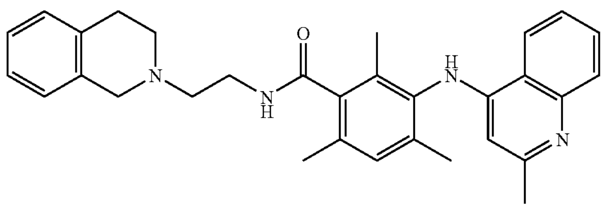 | N-[2-(3,4-Dihydro-1H-isoquinolin-2-yl)ethyl]-2,4,6-trimethyl-3-(2-methylquinolin-4-ylamino)benzamide | pink solid | 479.27 |
| 108 | 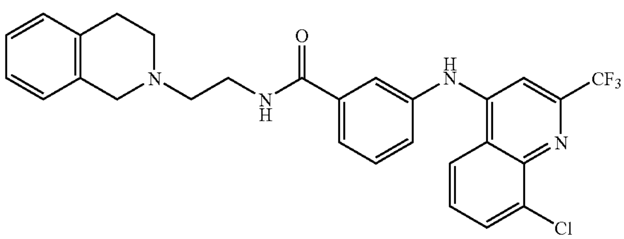 | 3-(8-Chloro-2-trifluoromethyl quinolin-4-ylamino)-N-[2-(3,4-dihydro-1H-isoquinolin-2-yl)ethyl] benzamide | yellow solid | 525.21 |
| 109 | 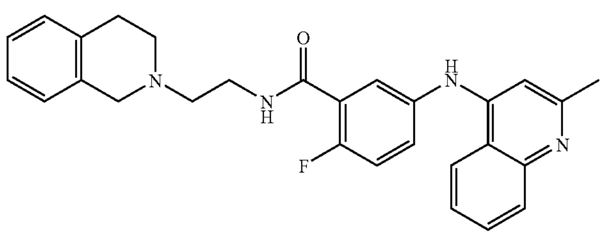 | N-[2-(3,4-Dihydro-1H-isoquinolin-2-yl)ethyl]-2-fluoro-5-(2-methyl quinolin-4-ylamino)benzamide | white solid | |
| 110 | 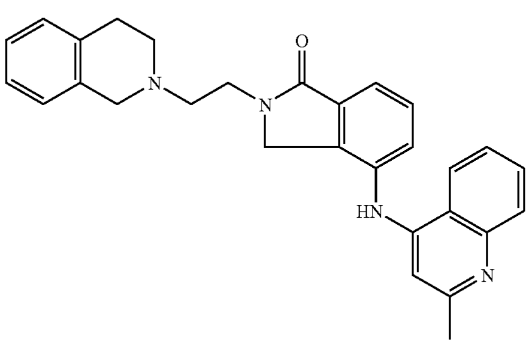 | 2-[2-(3,4-Dihydro-1H-isoquinolin-2-yl)ethyl]-4-(2-methylquinolin-4-yl amino)-2,3-dihydroisoindol-1-one | off-white solid | 449.21 |

TABLE 3-continued

| Example | Structure | Chemical Name | Physical Description[a] | [M + H]+ |
|---|---|---|---|---|
| 111 | 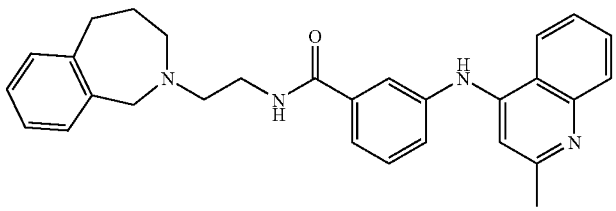 | 3-(2-Methylquinolin-4-ylamino)-N-[2-(1,3,4,5-tetrahydrobenzo[c]azepin-2-yl)ethyl]benzamide | yellow solid | 451.23 |
| 112 | 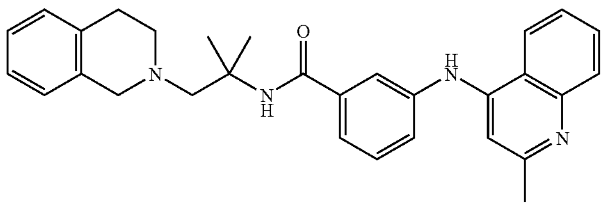 | N-[2-(3,4-Dihydro-1H-isoquinolin-2-yl)-1,1-dimethylethyl]-3-(2-methylquinolin-4-ylamino)benzamide | light yellow solid | 465.25 |
| 113 | 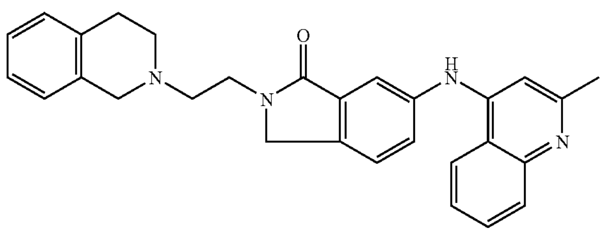 | 2-[2-(3,4-Dihydro-1H-isoquinolin-2-yl)ethyl]-6-(2-methylquinolin-4-ylamino)-2,3-dihydroisoindol-1-one | yellow solid | 449.26 |
| 114 | 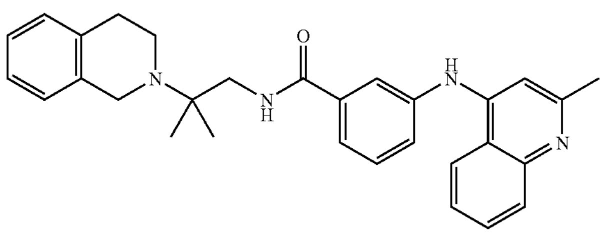 | N-[2-(3,4-Dihydro-1H-isoquinolin-2-yl)-2-methylpropyl]-3-(2-methylquinolin-4-ylamino)benzamide | light yellow solid | 465.23 |
| 115 | 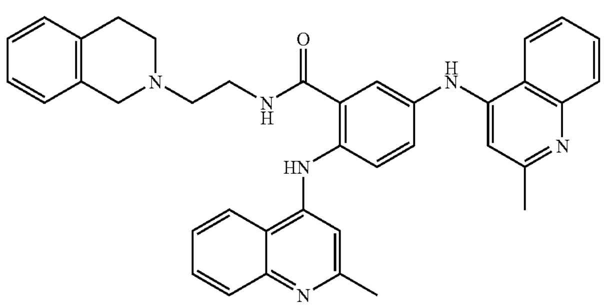 | N-[2-(3,4-Dihydro-1H-isoquinolin-2-yl)ethyl]-2,5-bis(2-methylquinolin-4-ylamino)benzamide | yellowish solid | 452.18 |
| 116 | 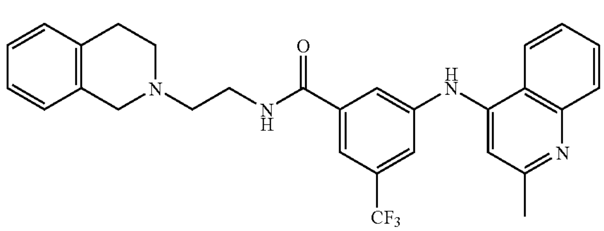 | N-[2-(3,4-Dihydro-1H-isoquinolin-2-yl)ethyl]-3-(2-methylquinolin-4-ylamino)-5-trifluoromethylbenzamide | off-white solid | 505.19 |

TABLE 3-continued

| Example | Structure | Chemical Name | Physical Description[a] | [M + H]+ |
|---|---|---|---|---|
| 117 | 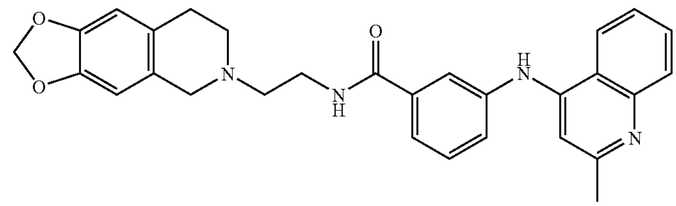 | N-[2-(7,8-Dihydro-5H-[1,3]dioxolo[4,5-g]isoquinolin-6-yl)ethyl-3-(2-methylquinolin-4-ylamino)benzamide | pale yellow solid | 481.20 |
| 118 | 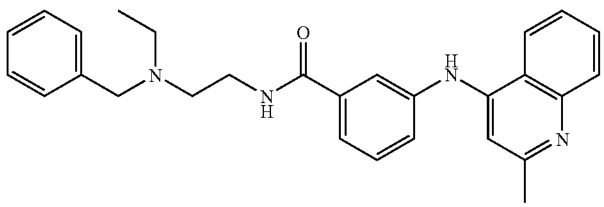 | N-[2-(Benzylethylamino)ethyl]-3-(2-methylquinolin-4-ylamino)benzamide | pale yellow | 439.18 |
| 119 | 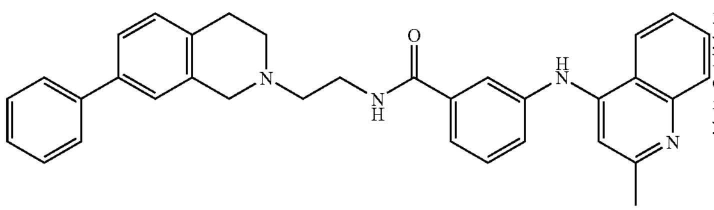 | 3-(2-Methylquinolin-4-ylamino)-N-[2-(7-phenyl-3,4-dihydro-1H-isoquinolin-2-yl)ethyl]benzamide | yellow solid | 513.29 |
| 120 | 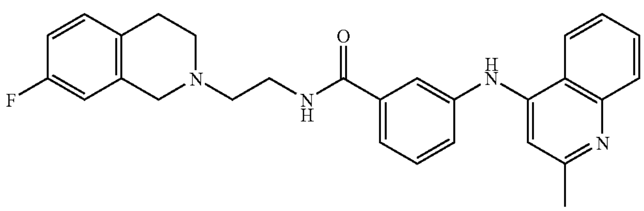 | N-[2-(7-Fluoro-3,4-dihydro-1H-isoquinolin-2-yl)ethyl]-3-(2-methylquinolin-4-ylamino)benzamide | yellow solid | 455.18 |
| 121 | 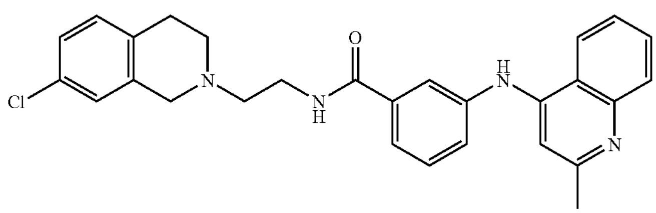 | N-[2-(7-Chloro-3,4-dihydro-1H-isoquinolin-2-yl)ethyl]-3-(2-methylquinolin-4-ylamino)benzamide | off-white solid | 471.16 |
| 122 | 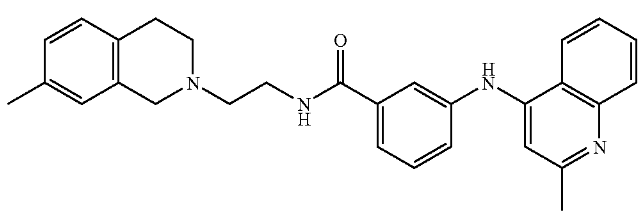 | N-[2-(7-Methyl-3,4-dihydro-1H-isoquinolin-2-yl)ethyl]-3-(2-methylquinolin-4-ylamino)benzamide | yellow solid | 451.22 |
| 123 | 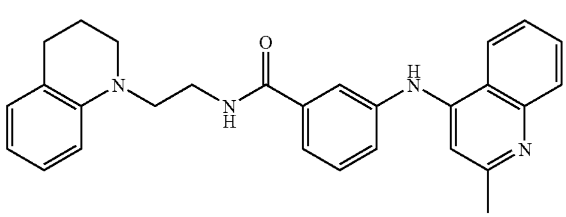 | N-[2-(3,4-Dihydro-2H-quinolin-1-yl)ethyl]-3-(2-methylquinolin-4-ylamino)benzamide | yellow solid | 437.25 |

TABLE 3-continued

| Example | Structure | Chemical Name | Physical Description[a] | [M + H]+ |
|---|---|---|---|---|
| 124 | 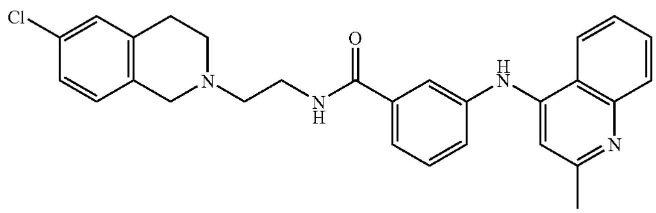 | N-[2-(6-Chloro-3,4-dihydro-1H-isoquinolin-2-yl)ethyl]-3-(2-methyl quinolin-4-ylamino)benzamide | off-white solid | |
| 125 | 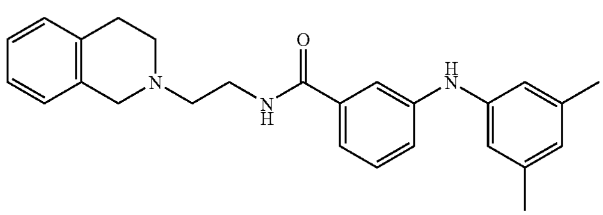 | N-[2-(3,4-Dihydro-1H-isoquinolin-2-yl)ethyl]-3-(3,5-dimethyl-phenylamino)benzamide | white solid[b] | 400.18 |
| 126 | 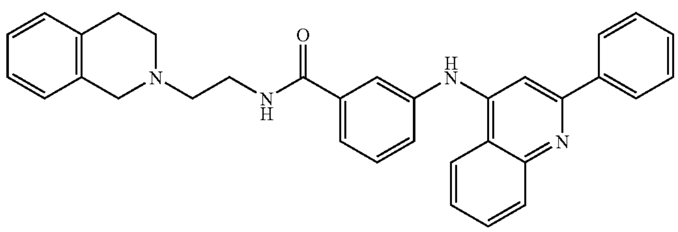 | N-[2-(3,4-Dihydro-1H-isoquinolin-2-yl)ethyl]-3-(2-phenylquinolin-4-yl amino)benzamide | yellow solid | 499.24 |
| 127 | 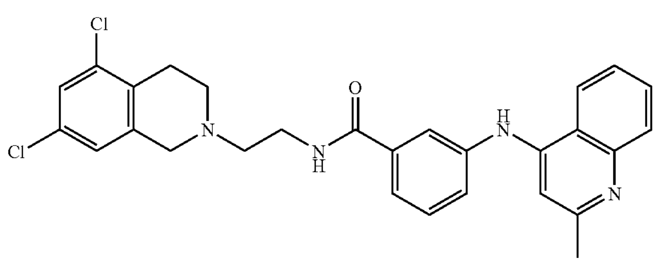 | N-[2-(5,7-Dichloro-3,4-dihydro-1H-isoquinolin-2-yl)ethyl]-3-(2-methyl quinolin-4-ylamino)benzamide | yellow solid[b] | 505.08 |
| 128 | 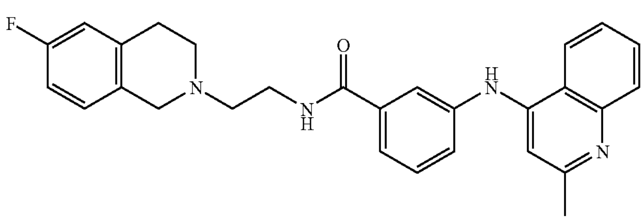 | N-[2-(6-Fluoro-3,4-dihydro-1H-isoquinolin-2-yl)ethyl]-3-(2-methyl quinolin-4-ylamino)benzamide | yellow solid | 455.25 |
| 129 | 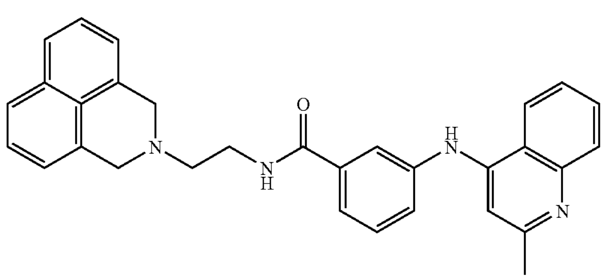 | N-[2-(1H,3H-Benzo[de]isoquinolin-2-yl)ethyl]-3-(2-methylquinolin-4-yl amino)benzamide | yellow solid | 773.20 |

TABLE 3-continued

| Example | Structure | Chemical Name | Physical Description[a] | [M + H]+ |
|---|---|---|---|---|
| 130 | 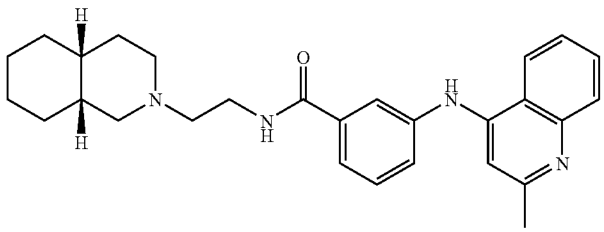 | 3-(2-Methylquinolin-4-ylamino)-N-[2-(octahydro-cis-isoquinolin-2-yl)ethyl]benzamide | yellow solid | 443.26 |
| 131 | 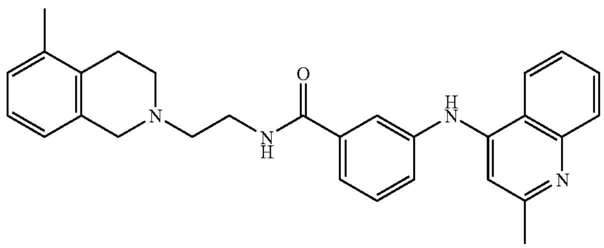 | N-[2-(5-Methyl-3,4-dihydro-1H-isoquinolin-2-yl)ethyl]-3-(2-methyl quinolin-4-ylamino)benzamide | yellow solid | 451.24 |
| 132 | 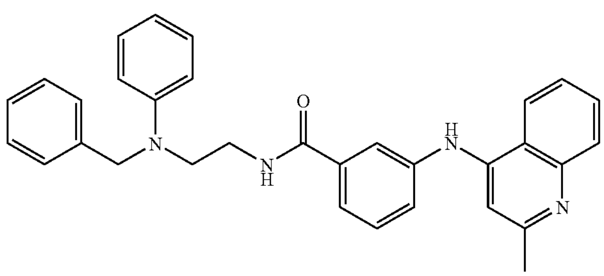 | M-[2-(Benzylphenyl-amino)ethyl]-3-(2-methylquinolin-4-ylamino) benzamide | pale yellow solid[b] | 487.24 |
| 133 | 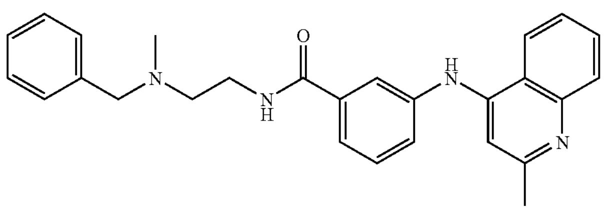 | N-[2-(Benzylmethyl-amino)ethyl]-3-(2-methylquinolin-4-ylamino) benzamide | pale yellow solid | 425.21 |
| 134 | 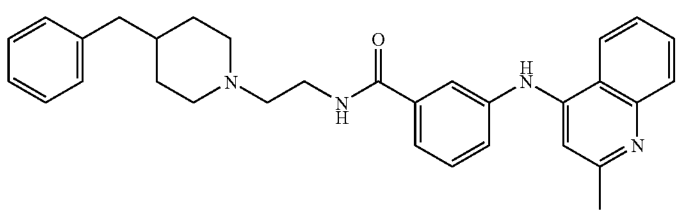 | N-[2-(4-Benzylpiperidin-1-yl)ethyl]-3-(2-methylquinolin-4-ylamino) benzamide | yellow solid | 479.24 |
| 135 | 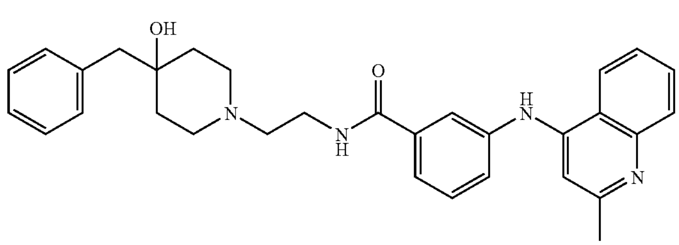 | N-[2-(4-Benzyl-4-hydroxy piperidin-1-yl)ethyl]-3-(2-methyl quinolin-4-ylamino)benzamide | yellow solid | 495.20 |

TABLE 3-continued

| Example | Structure | Chemical Name | Physical Description[a] | [M + H]+ |
|---|---|---|---|---|
| 136 | 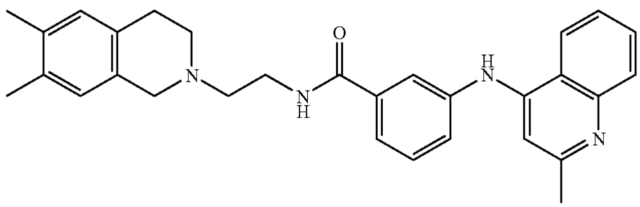 | N-[2-(6,7-Dimethyl-3,4-dihydro-1H-(2-methyl quinolin-4-ylamino)benzamide | yellow solid | |
| 137 | 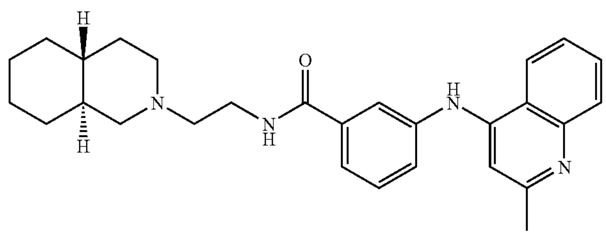 | 3-(2-Methylquinolin-4-ylamino)-N-[2-(octahydro-trans-isoquinolin-2-yl)ethyl]benzamide | brown solid | 443.31 |
| 138 | 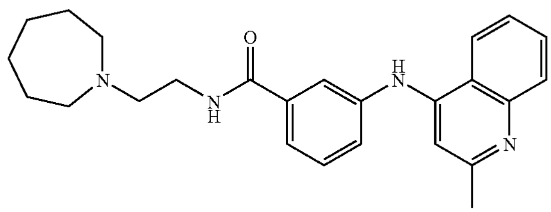 | N-(2-Azepan-1-ylethyl)-3-(2-methylquinolin-4-ylamino)benzamide | yellow solid | 403.23 |
| 139 | 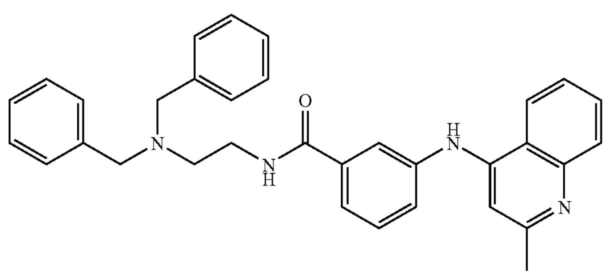 | N-(2-Dibenzylaminoethyl)-3-(2-methylquinolin-4-ylamino)benzamide | yellow solid | 501.26 |
| 140 | 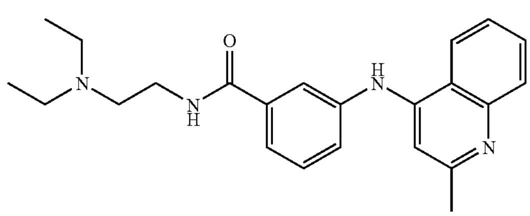 | N-(2-Diethylaminoethyl)-3-(2-methylquinolin-4-benzamide | yellow solid | 378.09 |
| 141 | 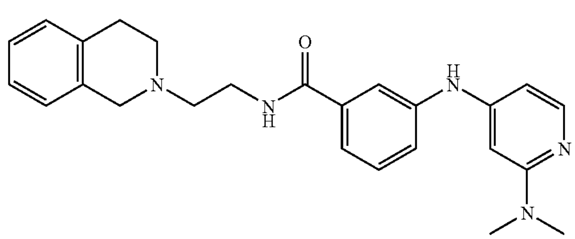 | N-[2-(3,4-Dihydro-1H-isoquinolin 2-yl)ethyl]-3-(2-dimethylamino pyridin-4-ylamino)benzamide | pale orange solid | 416.26 |

TABLE 3-continued

| Example | Structure | Chemical Name | Physical Description[a] | [M + H]+ |
|---|---|---|---|---|
| 142 | 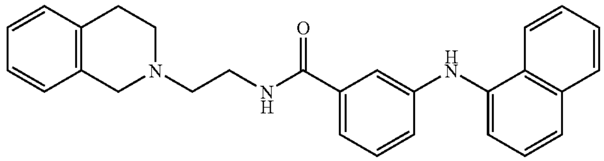 | N-[2-(3,4-Dihydro-1H-isoquinolin-2-yl)ethyl]-3-(naphthalen-1-yl amino)benzamide | brown solid[d] | 422.23 |
| 143 | 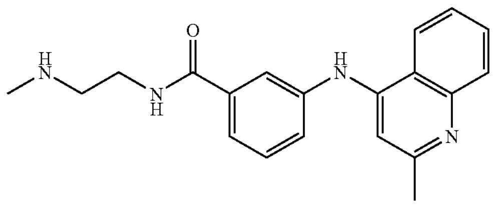 | N-(2-Methylaminoethyl)-3-(2-methyl quinolin-4-ylamino)benzamide | pale yellow solid[b] | 335.21 |
| 144 | 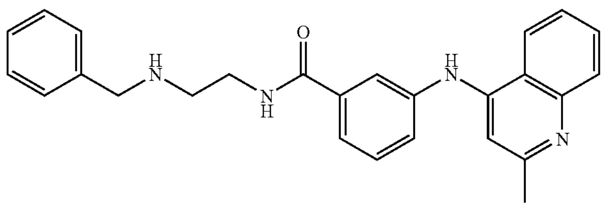 | N-(2-Benzylaminoethyl)-3-(2-methyl quinolin-4-ylamino)benzamide | yellow solid | 411.24 |
| 145 | 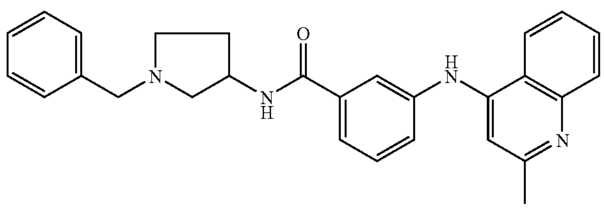 | N-(1-Benzylpyrrolidin-3-yl)-3-(2-methylquinolin-4-ylamino) benzamide | yellow solid | 437.28 |
| 146 | 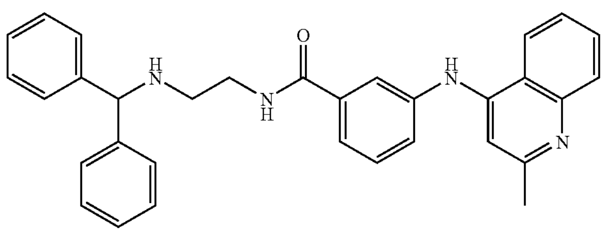 | N-[2-(Benzhydryl-amino)ethyl]-3-(2-methylquinolin-4-ylamino) benzamide | off-white solid | 487.18 |
| 147 | 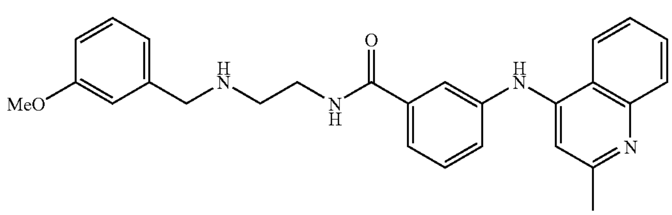 | N-[2-(3-Methoxybenzylamino) ethyl]-3-(2-methylquinolin-4-yl amino)benzamide | pale yellow solid | 441.26 |
| 148 | 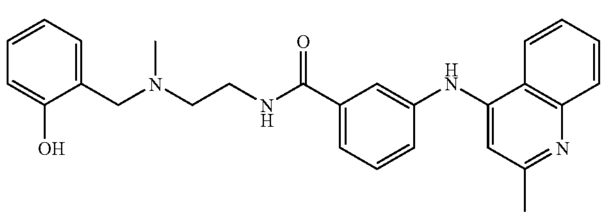 | N-{2-[(2-Hydroxybenzyl)methyl amino]ethyl}-3-(2-methyl quinolin-4-ylamino)benzamide | pale yellow solid[b] | 441.11 |

TABLE 3-continued

| Example | Structure | Chemical Name | Physical Description[a] | [M + H]+ |
|---|---|---|---|---|
| 149 | 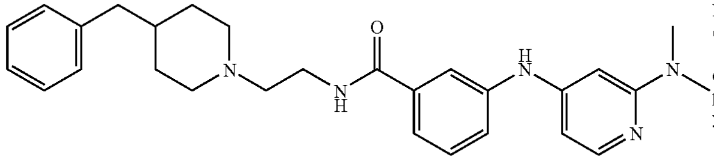 | N-[2-(4-Benzylpiperidin-1-yl)ethyl]-3-(2-dimethylamino pyridin-4-ylamino)benzamide | orange solid | 458.26 |
| 150 | 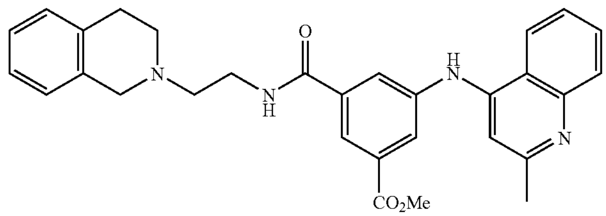 | MethylN-[2-(3,4-dihydro-1H-isoquinolin-2-yl)ethyl]-5-(2-methylquinolin-4-ylamino)iso-phthalamate | off-white solid | 495.23 |
| 151 | 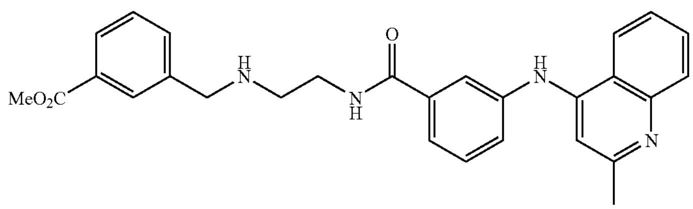 | Methyl3-({2-[3-(2-methyl quinolin-4-ylamino)benzoyl-amino] ethylamino}-methyl)benzoate | pale yellow solid | 469.29 |
| 152 | 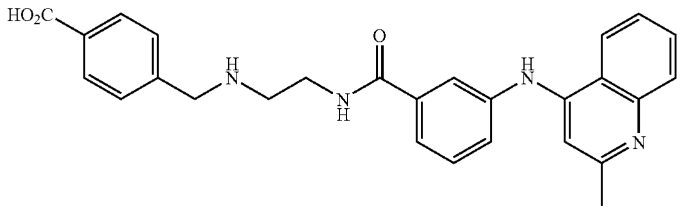 | 4-{2-[3-(2-Methylquinolin-4-yl amino)-benzoylamino] ethylamino} methyl)benzoic acid | pale yellow solid[e] | 455.30 |
| 153 | 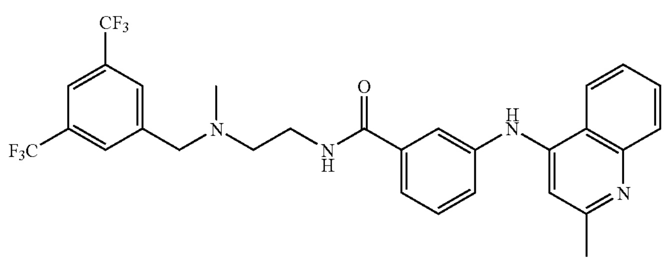 | N-{2-[(3,5-Bis-trifluoromethyl benzyl)methylamino] ethyl}-3-(2-methylquinolin-4-ylamino)benzamide | pale yellow solid | 561.28 |
| 154 | 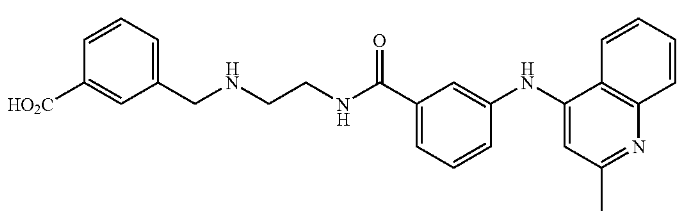 | 3-({2-[3-(2-Methyl quinolin-4-ylamino)benzoyl-amino]ethylamino}-methyl)benzoic acid | pale yellow solid[e] | 455.27 |
| 155 | 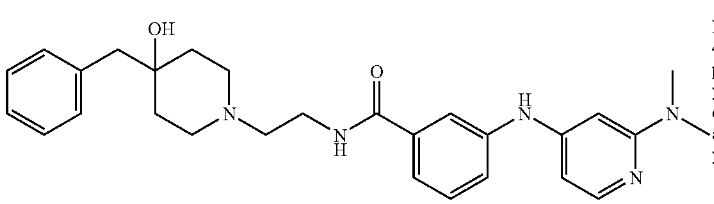 | N-[2-(4-Benzyl-4-hydroxy piperidin-1-yl)ethyl]-3-(2-dimethyl aminopyridin-4-ylamino)benzamide | pale yellow solid | 474.28 |

TABLE 3-continued

| Example | Structure | Chemical Name | Physical Description[a] | [M + H]+ |
|---|---|---|---|---|
| 156 | 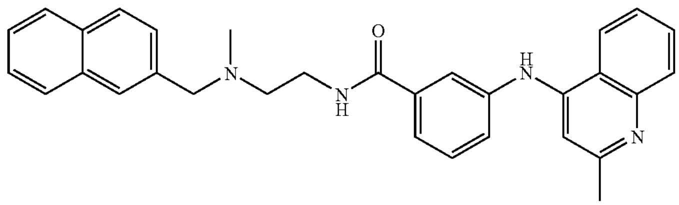 | N-[2-(Methyl-naphthalen-2-ylmethyl amino)ethyl]-3-(2-methyl quinolin-4-ylamino)benzamide | yellow solid | 475.24 |
| 157 | 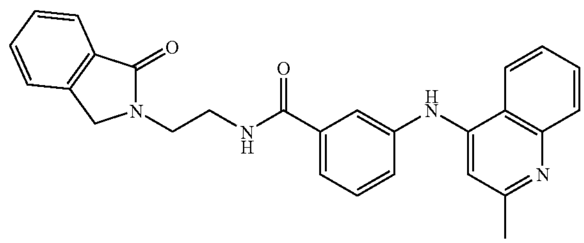 | 3-(2-Methylquinolin-4-ylamino)-N-[2-(1-oxo-1,3-dihydro isoindol-2-yl)-ethyl]benzamide | off-white solid[d] | 437.24 |
| 158 | 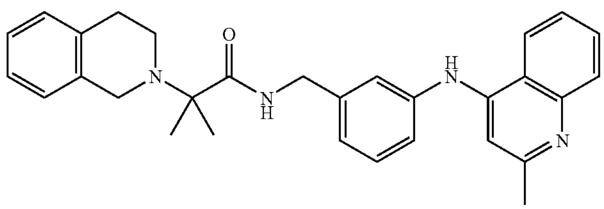 | 2-(3,4-Dihydro-1H-isoquinolin-2-yl)-N-[3-(2-methylquinolin-4-benzyl]isobutyramide | yellow solid | 465.28 |
| 159 | 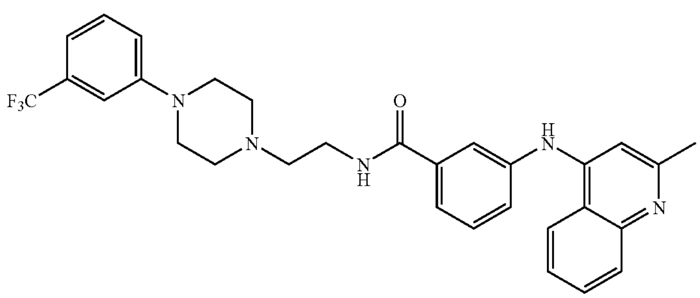 | 3-(2-Methylquinolin-4-ylamino)-trifluoro-methylphenyl)piperazin-1-yl]-ethyl}benzamide | light yellow solid | 534.30 |
| 160 | 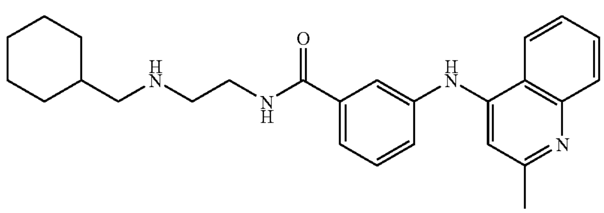 | N-[2-(Cyclohexylmethyl-amino)ethyl]-3-(2-methylquinolin-4-yl amino)benzamide | pale yellow solid | 417.29 |
| 161 | 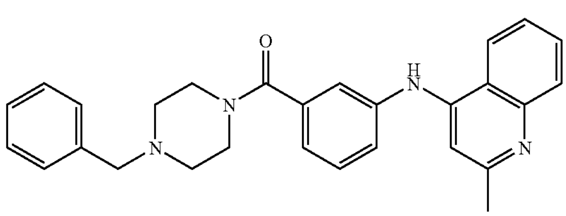 | 1-Benzyl-4-[3-(2-methylquinolin-4-ylamino)benzoyl]piperazine | brown solid | 437.30 |

TABLE 3-continued

| Example | Structure | Chemical Name | Physical Description[a] | [M + H]+ |
|---|---|---|---|---|
| 162 | 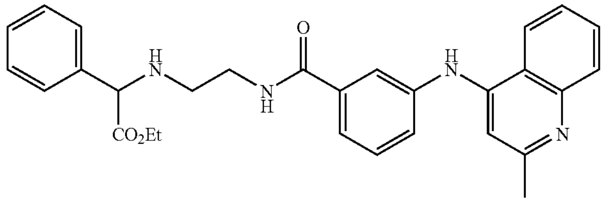 | Ethyl{2-[3-(2-methylquinolin-4-ylamino)benzoylamino]ethylamino}phenylacetate | pale yellow solid | 483.25 |
| 163 | 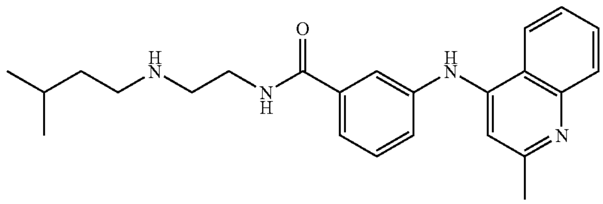 | N-[2-(3-Methylbutylamino)ethyl]-3-(2-methylquinolin-4-ylamino)benzamide | pale yellow solid | 391.23 |
| 164 | 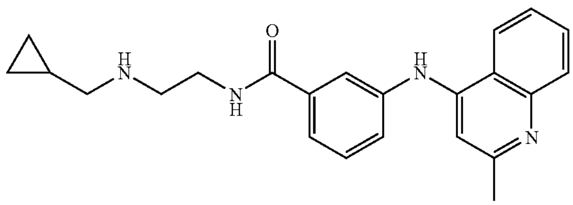 | N-[2-(Cyclopropylmethylamino)ethyl]-3-(2-methylquinolin-4-ylamino)benzamide | pale yellow solid | 374.27 |
| 165 | 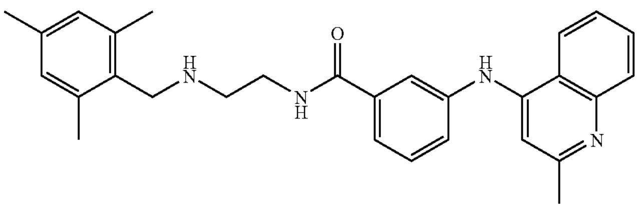 | 3-(2-Methylquinolin-4-ylamino)-N-[2-(2,4,6-trimethylbenzylamino)ethyl]benzamide | pale yellow solid | 453.25 |
| 166 | 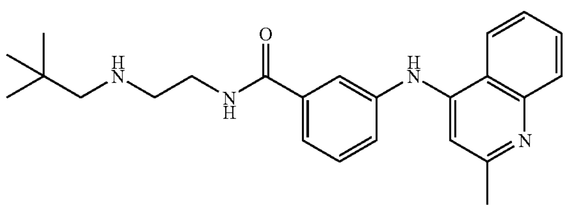 | N-[2-(2,2-methylpropylamino)ethyl]-3-(2-methylquinolin-4-ylamino)benzamide | pale yellow solid | 391.27 |
| 167 | 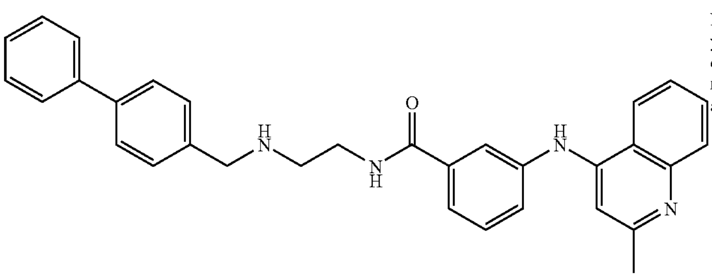 | N-{2-[(Biphenyl-4-ylmethyl)amino]ethyl}-3-(2-methylquinolin-4-ylamino)benzamide | pale yellow solid | 487.20 |
| 168 | 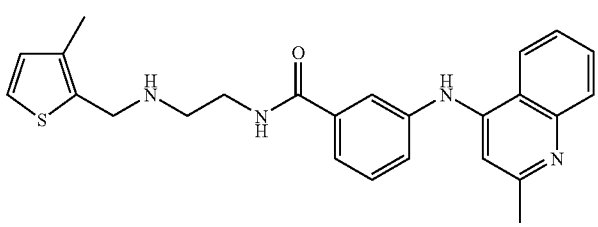 | 3-(2-Methylquinol-4-ylamino)-N-{2-[(3-methylthiophen-2-yl)amino]methyl}ethyl}benzamide | pale yellow solid | 431.11 |

TABLE 3-continued

| Example | Structure | Chemical Name | Physical Description[a] | [M + H]+ |
|---|---|---|---|---|
| 169 | 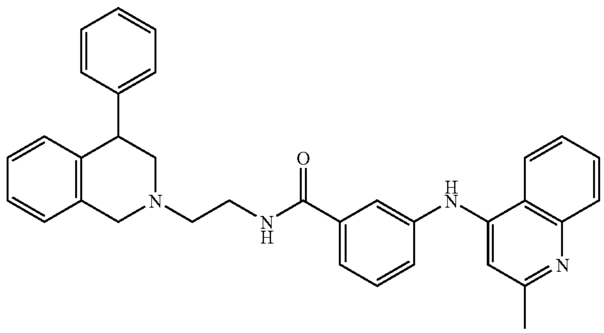 | 3-(2-Methylquinolin-4-ylamino)-N-[2-(4-phenyl-3,4-dihydro-1H-isoquinolin-2-yl)ethyl]benzamide | off-white solid | 513.26 |
| 170 | 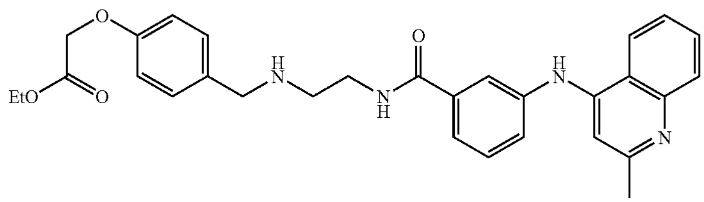 | Ethyl[4-({2-[3-(2-methylquinolin-4-ylamino)benzoyl-amino]ethylamino}methyl)phenoxy]acetate | off-white solid[b] | 513.15 |
| 171 | 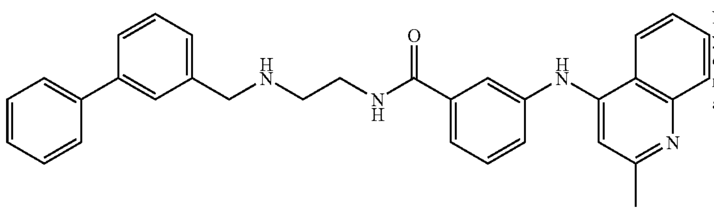 | N-{2-[(Biphenyl-3-ylmethyl)amino]ethyl}-3-(2-methylquinolin-4-ylamino)benzamide | off-white solid[b] | 487.26 |
| 172 | 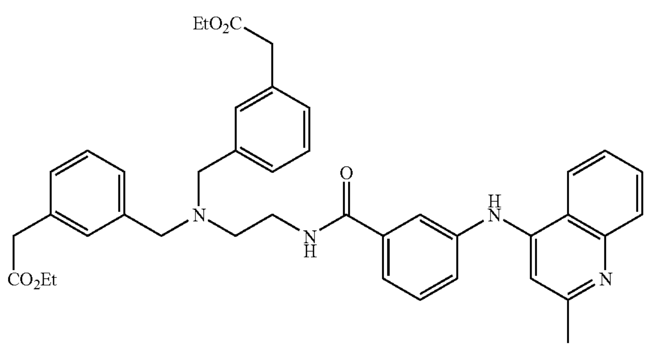 | Ethyl{3-[((3-ethoxycarbonylmethylbenzyl)-{2-[3-(2-methylquinolin-4-ylamino)benzoylamino[ethyl}amino)methyl]phenyl}acetate | pale yellow solid[b] | 673.34 |
| 173 | 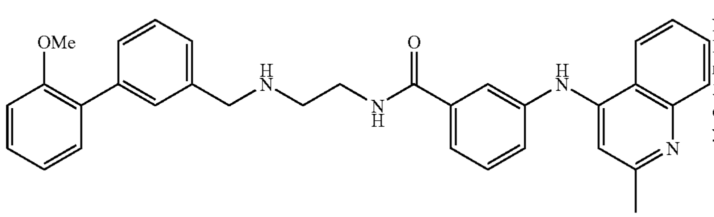 | N-{2-[(2'-Methoxybiphenyl-3-ylmethyl)amino]ethyl}-3-(2-methylquinolin-4-ylamino)benzamide | pale yellow solid[b] | 517.29 |

[a]DiHCl salt unless otherwise noted.
[b]Parent compound
[d]HCl salt
[c]Na salt

The compound of Example 174 was synthesized in the same manner as the compound of Example 1.

The compound of Example 175 was synthesized in the same manner as the compound of Example 177.

The preparation of the compounds of Examples 176 and 177 are shown.

The compound of Example 178 was synthesized in the same manner as the compound of Example 1.

The preparation of the compound of Example 179 is shown.

The compound of Example 180 was synthesized in the same manner as the compound of Example 179.

The preparation of the compound of Example 181 is shown.

The compound of Example 182 was synthesized in the same manner as the compound of Example 178 except that N-[2-(3,4-dihydro-1H-isoquinolin-2-yl)ethyl]-3-nitrobenzenesulfonamide was methylated using a standard method (NaH/MeI/DMF) before carried on to the next step.

The preparation of the compounds of Examples 183 and 184 are shown.

The compound of Example 185 was synthesized in the same manner as the compound of Example 184.

The preparation of the compound of Example 186 is shown.

The compounds of Examples 187 and 188 were synthesized in the same manner as the compound of Example 184.

The preparation of the compounds of Examples 189 to 191 are shown.

The compounds of Examples 192 to 194 were synthesized in the same manner as the compound of Example 186.

The compound of Example 195 was synthesized in the same manner as the compound of Example 190.

The compound of Example 196 was synthesized in the same manner as the compound of Example 186.

The compound of Example 197 was synthesized in the same manner as the compound of Example 191.

The preparation of the compound of Example 198 is shown.

The compound of Example 199 was synthesized in the same manner as the compound of Example 198.

The compound of Example 200 was synthesized in the same manner as the compound of Example 191.

The compound of Example 201 was synthesized via reduction (see Example 112 step 3) of the compound of Example 134.

The preparation of the compounds of Examples 202 and 203 are shown.

The compound of Example 204 was synthesized in the same manner as the compound of Example 198.

The compounds of Examples 205 and 206 were synthesized in the same manner as the compound of Example 2.

The compound of Example 207 was synthesized via reduction (see Example 112 step 3) of the compound of Example 144.

The preparation of the compounds of Examples 208 to 210 are shown.

The compound of Example 211 was synthesized in the same manner as the compound of Example 210.

The structures, chemical names, physical descriptions and M+H data for the compounds of Examples 174–211 are set forth in Table 4.

Example 176

N-(2-Dimethylaminoethyl)-N'-(2-methylquinolin-4-yl)phenylene-1,3-diamine

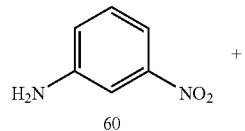

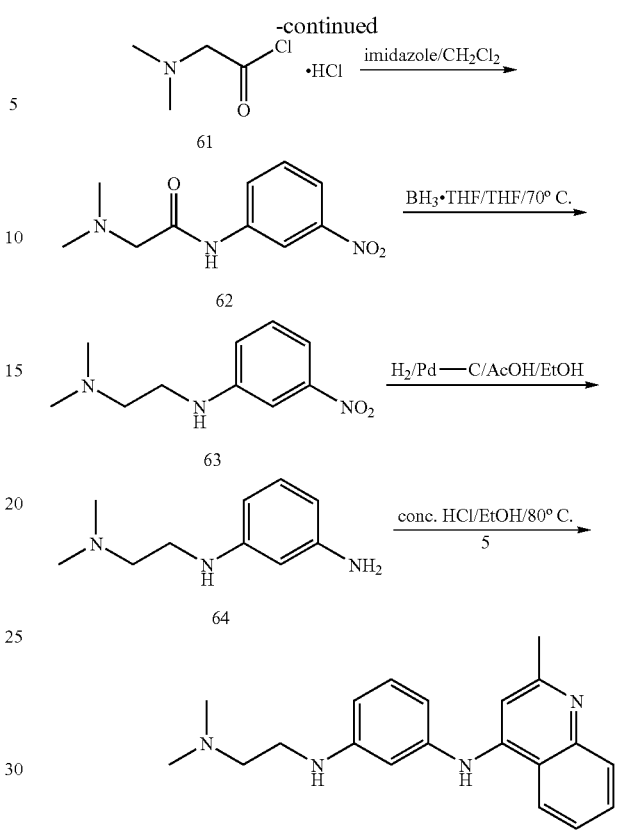

Example 176

Step 1. 2-Dimethylamino-N-(3-nitrophenyl)acetamide (62).

To a heterogeneous mixture of 61 (186 mg, 1.18 mmol) in dichloromethane (6 mL) were sequentially added imidazole (281 mg, 4.13 mmol) and a solution of 60 (214 mg, 1.55 mmol) in dichloromethane (6 mL). The reaction was stirred at room temperature for 16 hours before it was extracted with ethyl acetate (40 mL, 30 mL) and washed with water (30 mL). The ethyl acetate extracts were dried over anhydrous magnesium sulfate and concentrated. The residue was chromatographed on silica gel (1:1 hexanes/ethyl acetate to 10:1 dichloromethane/methanol) to give 62 as a yellow oil.

Step 2. N,N-Dimethyl-N'-(3-nitrophenyl)ethane-1,2-diamine (63).

To a solution of 62 (482 mg, 2.05 mmol) in THF (2.8 mL) under a $N_2$ atmosphere was added $BH_3$.THF (1.0 M solution in THF, 2.8 mL, 2.80 mmol). The reaction was heated at 70° C. for 1.5 hours before it was allowed to cool to room temperature.

The mixture was treated with 2 N HCl (aq. 3 mL) (moderate bubbling) and then the solvent was evaporated. The aqueous residue was extracted with chloroform (2×40 mL) and washed with sat. $NaHCO_3$ (aq.), water, and brine (20 mL each). The chloroform extracts were dried over anhydrous magnesium sulfate and concentrated. The residue was chromatographed on Florisil® (1:1 hexanes/ethyl acetate to 10:1 dichloromethane/methanol) to afford 63 as a yellow oil (124 mg, 28.9%).

Step 3. N-(2-Dimethylaminoethyl)benzene-1,3-diamine (64).

64 is prepared from 63 by the procedure of Example 1 Step 2.

Step 4. N-(2-Dimethylaminoethyl)-N'-(2-methylquinolin-4-yl)phenylene-1,3-diamine The title compound is prepared from 64 by the procedure of Example 1 Step 3.

EXAMPLE 177

[3-(3-Dimethylaminopropyl)phenyl]-(2-methylquinolin-4-yl)amine

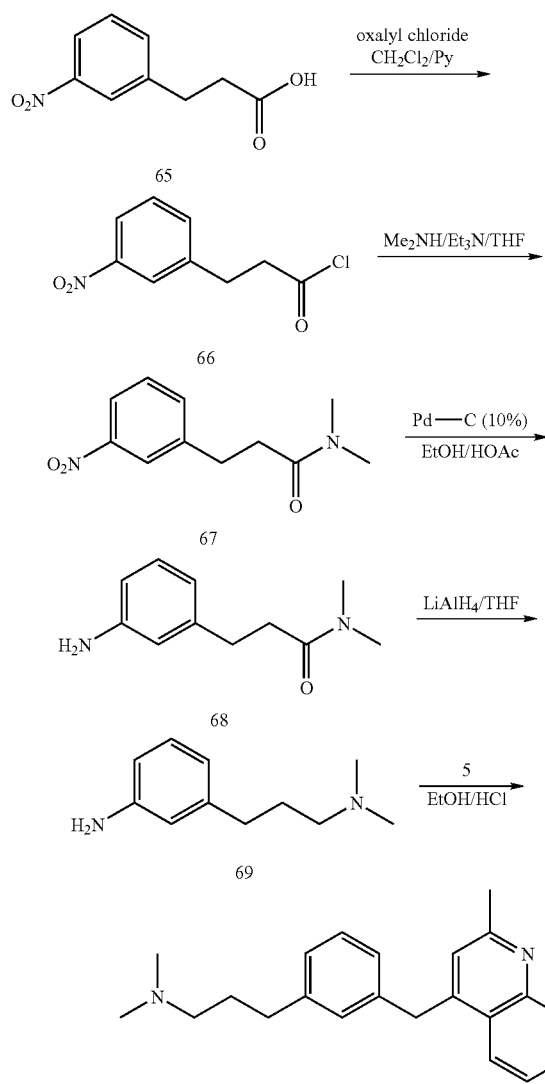

Example 177

Step 1. N,N-Dimethyl-3-(3-nitrophenyl)propionamide (67).

To a suspension of 65 (2.04 g, 10.45 mmol) in anhydrous dichloromethane (15 mL) under nitrogen were sequentially added anhydrous pyridine (2 drops) and oxalyl chloride (2 M in CH$_2$Cl$_2$, 11.5 mL, 23 mmol) dropwise. The resulting mixture was heated at 50° C. for 1.5 hours before it was concentrated. The residue was dissolved in anhydrous THF (20 mL) under nitrogen followed by the sequential addition of triethylamine (1.16 mL, 11.55 mmol) and dimethylamine (2 M in THF, 7.87 mL, 15.68 mmol). The reaction was stirred at room temperature overnight before it was diluted with EtOAc (150 mL), and washed with water (150 mL) and brine (150 mL). The organic layer was dried over Na$_2$SO$_4$ and evaporated under reduced pressure to give 67 as a yellowish oil (977 mg, 43%).

Step 2. 3-(3-Aminophenyl)-N,N-dimethylpropionamide (68).

68 was prepared from 67 by the procedure of Example 1 Step 2.

Step 3. 3-(3-Dimethylaminopropyl)phenylamine (69).

69 was prepared from 68 by the procedure of Example 112 Step 3.

Step 4. [3-(3-Dimethylaminopropyl)phenyl]-(2-methylquinolin-4-yl)amine.

The title compound is prepared from 69 by the procedure of Example 1 Step 3.

EXAMPLE 179

[3'-(3,4-Dihydro-1H-isoquinolin-2-ylmethyl)biphenyl-3-yl]-(2-methylquinolin-4-yl)amine.

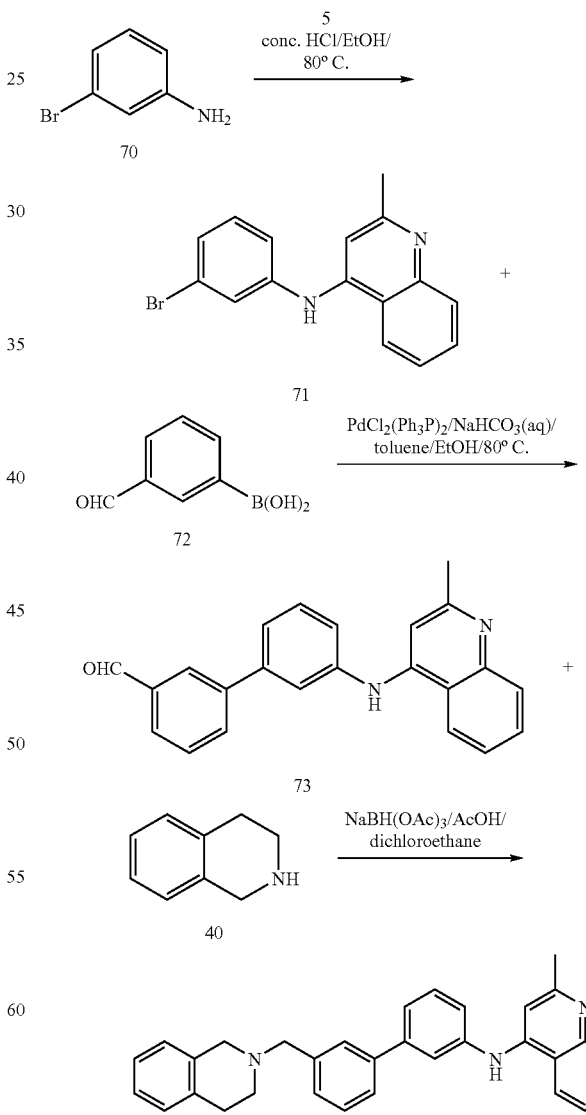

Example 179

Step 1. (3-Bromophenyl)-(2-methylquinolin-4-yl)amine (71).

71 is prepared from 70 by the procedure of Example 1 Step 3.

Step 2. 3'-(2-Methylquinolin-4-ylamino)biphenyl-3-carbaldehyde (73).

To a suspension of 71 (294 mg, 0.94 mmol) in toluene (9.6 mL) under N$_2$ were sequentially added saturated NaHCO$_3$ (aq. 3.8 mL), a solution of 72 (199 mg, 1.33 mmol) in EtOH (6.7 mL), and PdCl$_2$(Ph$_3$P)$_3$ (32 mg, 0.046 mmol). The reaction was heated at 80° C. for 21 hours before it was allowed to cool to room temperature. The reaction mixture was extracted with ethyl acetate (40 mL) and washed with water (15 mL), brine (15 mL). The ethyl acetate extracts were dried over anhydrous magnesium sulfate and concentrated. The residue was chromatographed on silica gel (dichloromethane to 20:1 dichloromethane/methanol) to give 73 as a yellow solid (219 mg, 68.9%).

Step 3. 3'-(3,4-Dihydro-1H-isoquinolin-2-ylmethyl)biphenyl-3-yl]-(2-methylquinolin-4-yl)amine.

To a solution of 73 (102 mg, 0.301 mmol) in dichloroethane (3.0 mL) under N$_2$ was added 40 (0.04 mL, 0.315 mmol). The reaction was stirred for 24 minutes before the sequential addition of NaBH(OAc)$_3$ (94 mg, 0.444 mmol) and AcOH (0.02 mL, 0.349 mmol). The reaction was stirred for 19 hours and then extracted with ethyl acetate (2×30 mL). The ethyl acetate extracts were washed with 2 N NaOH (aq. 15 mL), brine (15 mL), dried (MgSO$_4$), and concentrated. The residue was chromatographed on silica gel (dichloromethane to 30:1 to 20:1 dichloromethane/methanol) to give the desired product as a yellow solid (75 mg, 55%).

EXAMPLE 181

2-Dimethylaminoethyl 3-(2-methylquinolin-4-ylamino)benzoate

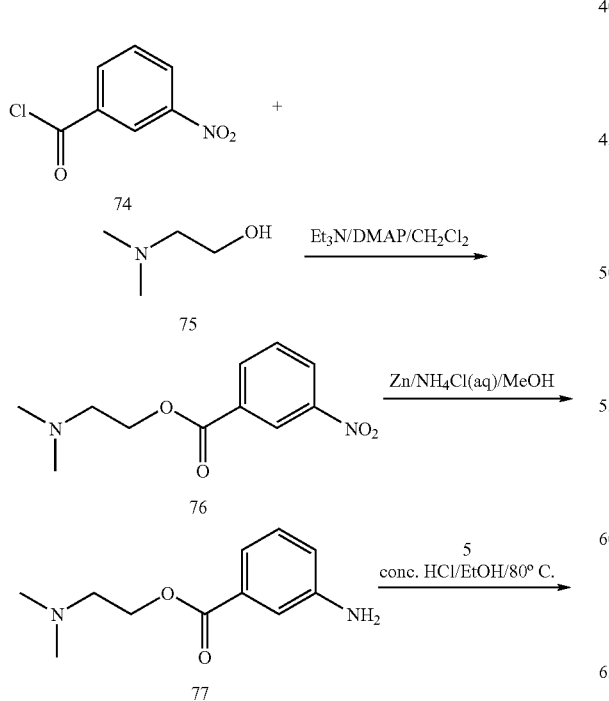

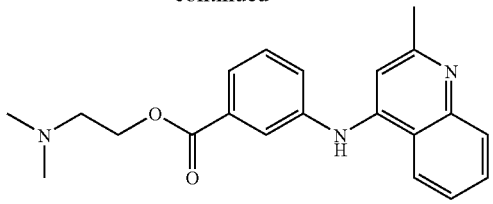

Example 181

Step 1. 2-Dimethylaminoethyl 3-nitrobenzoate (76).

To a solution of 74 (835 mg, 4.50 mmol) in dichloromethane (50 mL) were sequentially added triethylamine (0.63 mL, 6.75 mmol), a solution of 75 (800 mg, 8.97 mmol) in dichloromethane (10 mL) and a catalytic amount of DMAP. The reaction was stirred for 16 hours before it was extracted with dichlormethane. The dichloromethane extracts were washed with water and brine, dried (MgSO$_4$), and concentrated to give the crude product 76.

Step 2. 2-Dimethylaminoethyl 3-aminobenzoate (77).

77 was prepared from 76 by the procedure of Example 110 Step 4.

Step 3. 2-Dimethylaminoethyl 3-(2-methylquinolin-4-ylamino)benzoate.

The title compound was prepared from 77 by the procedure of Example 1 Step 3.

EXAMPLE 183

{3-[5-(3,4-Dihydro-1H-isoquinolin-2-ylmethyl)isoxazol-3-yl]phenyl}-(2-methyl-quinolin-4-yl)amine

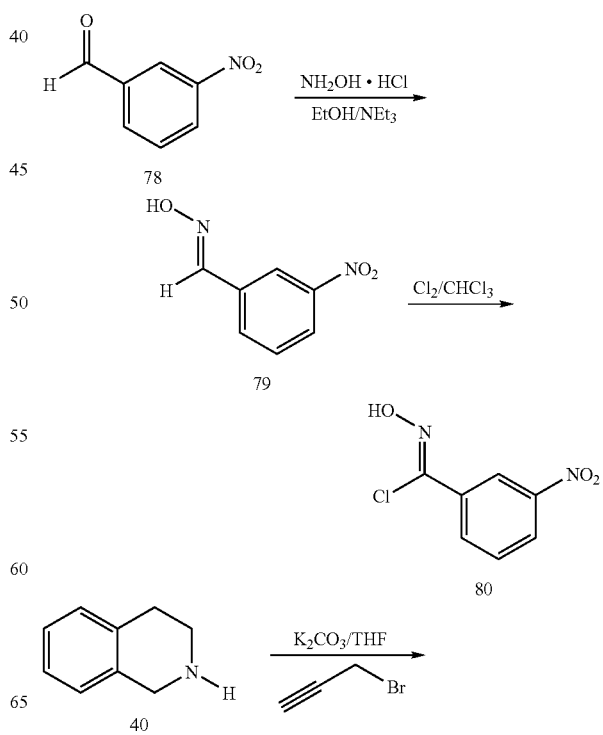

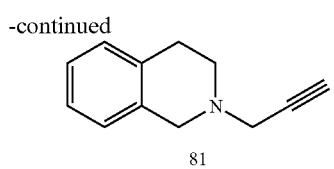

81

80 + 81 →(toluene, Δ)

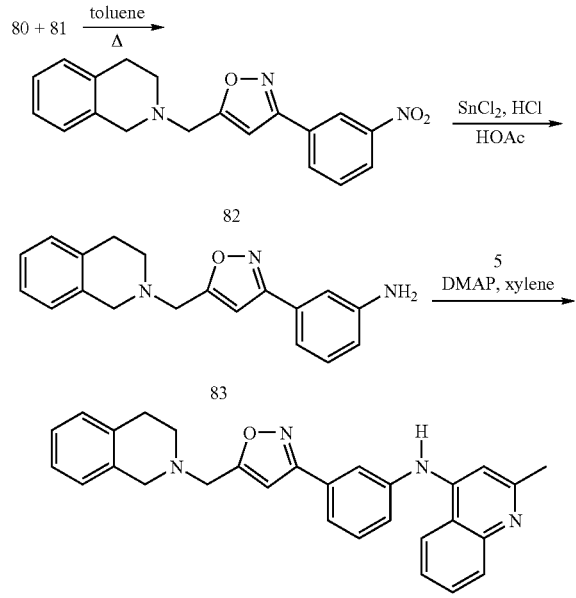

Example 183

Step 1. 3-Nitrobenzaldehyde oxime (79).

To a solution of 78 (6.04 g, 40 mmol) in ethanol (135 mL) were sequentially added hydroxylamine hydrochloride (2.92 g, 42 mmol) and triethylamine (4.6 g, 54 mmol). The mixture was heated at reflux overnight and concentrated under reduced pressure. The residue was mixed with ethyl acetate (100 mL) and washed with water (3×100 mL), brine (100 mL). The ethyl acetate solution was dried ($MgSO_4$) and concentrated under reduced pressure to give 79 (5.67 g, ~100%).

Step 2. 3-Nitrobenzonitrile oxide hydrogen chloride (80).

To a solution of 79 (1.66 g, 10 mmol) in chloroform (50 mL) was introduced chlorine gas at −5° C. over 15 minutes. The color of the reaction mixture changed from colorless to light blue, green, and finally yellow. After an additional 15 minutes, the reaction mixture was concentrated under reduced pressure to give 80 (2.0 g, 100%) as a yellow oil.

Step 3. 2-Propargyl-1,2,3,4-tetrahydroisoquinoline (81).
See Example 13 Step 2.

Step 4. 2-[3-(3-Nitrophenyl)isoxazol-5-ylmethyl]-1,2,3,4-tetrahydroisoquinoline (82).

A solution of 80 (0.2 g, 1.0 mmol) and 81 (0.2 g, 1.17 mmol) in toluene (5 mL) was heated at reflux for 4 hours. The reaction was cooled and mixed with 0.5 N NaOH (5 mL), then extracted with ethyl acetate (2×10 mL). The organic material was combined, dried ($K_2CO_3$) then concentrated under reduced pressure. The residue was purified by flash chromatography ($SiO_2$, gradient elution, hexane to 3:1 hexane/ethyl acetate) to give 82 (228 mg, 68%) as a yellow oil.

Step 5. 3-[5-(3,4-Dihydro-1H-isoquinolin-2-ylmethyl)isoxazol-3-yl]phenylamine (83).

83 was prepared from 82 by the procedure of Example 12 Step 2.

Step 6. {3-[5-(3,4-Dihydro-1H-isoquinolin-2-ylmethyl)isoxazol-3-yl]phenyl}-(2-methyl-quinolin-4-yl)amine.

The title compound was prepared from 83 by the procedure of Example 1 Step 3.

EXAMPLE 184

{3-[3-(3,4-Dihydro-1H-isoquinolin-2-yl)propyl]phenyl}-(2-methylquinolin-4-yl)amine.

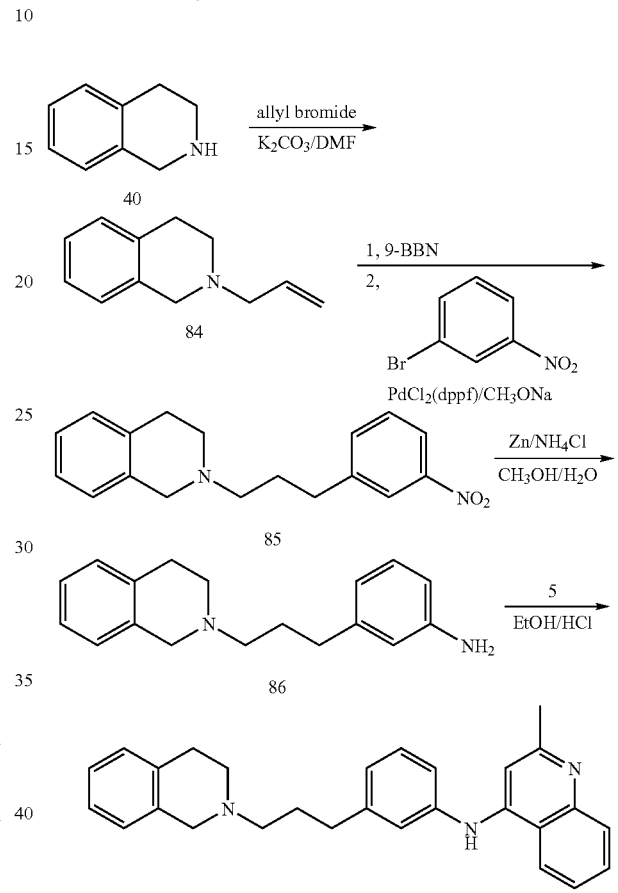

Example 184

Step 1. 2-Allyl-1,2,3,4-tetrahydroisoquinoline (84).

84 was prepared from 40 by the procedure of Example 13 Step 2.

Step 2. 2-[3-(3-Nitrophenyl)propyl]-1,2,3,4-tetrahydroisoquinoline (85).

To a solution of 84 (488 mg, 2.82 mmol) in anhydrous THF (3 mL) was added 9-BBN (0.5 M in THF, 5.64 mL, 2.82 mmol) under $N_2$. The mixture was stirred at room temperature for 3 hours to give mixture I.

To a solution of 1-bromo-3-nitrobenzene (518 mg, 2.56 mmol) in anhydrous THF (8 mL) were sequentially added $PdCl_2$(dppf) (63 mg, 0.0077 mmol) and sodium methoxide (416 mg, 7.68 mmol) to mixture II.

To mixture II was added dropwise mixture I under $N_2$ and the resulting mixture was heated at 75° C. for 17 hours. Upon cooling to room temperature, the reaction mixture was filtered, and the filtrate diluted with EtOAc (150 mL). The organic solution was washed with water (100 mL) and brine (100 mL), dried over $Na_2SO_4$, and concentrated under reduced pressure. The residue was purified through column

EXAMPLE 186

1-[2-(3,4-Dihydro-1H-isoquinolin-2-yl)ethyl]-3-[3-(2-methylquinolin-4-ylamino)phenyl]urea flash chromatography (silica gel) eluting with 8:1 hexanes/EtOAc to give 85 as an orange oil (226 mg, 27%).

Step 3. 3-[3-(3,4-Dihydro-1H-isoquinolin-2-yl)propyl]phenylamine (86).

86 was prepared from 85 by the procedure of Example 110 Step 4.

Step 4. {3-[3-(3,4-Dihydro-1H-isoquinolin-2-yl)propyl]phenyl}-(2-methylquinolin-4-yl)amine.

The title compound was prepared from 86 by the procedure of Example 1 Step 3.

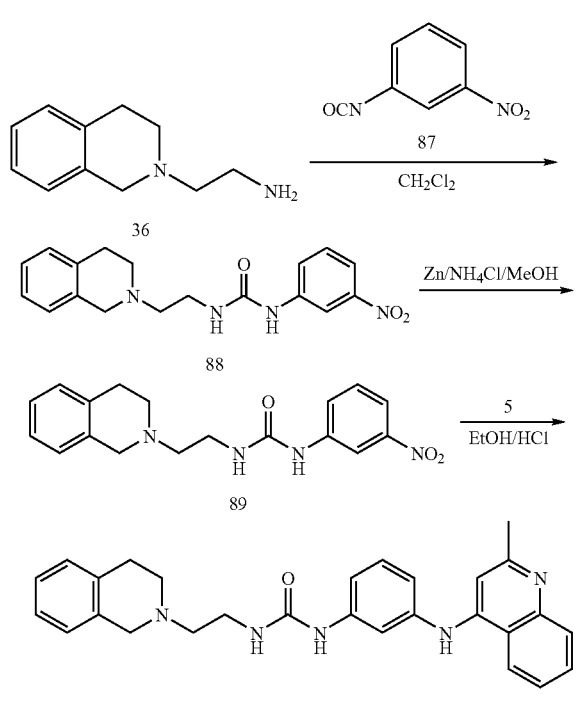

Example 186

Step 1. 1-[2-(3,4-Dihydro-1H-isoquinolin-2-yl)ethyl]-3-(3-nitrophenyl)urea (88).

To a solution of 36 (0.35 g, 2.0 mmol) in dichloromethane (10 mL) was added 3-nitrophenyl isocyanate (87) (0.35 g, 2.0 mmol). The mixture was stirred at room temperature overnight before it was partitioned between water (100 mL) and dichloromethane (100 mL). The organic layer was washed with 88 (0.56 g, 82%).

Step 2. 1-(3-Aminophenyl)-3-[2-(3,4-dihydro-1H-isoquinolin-2-yl)ethyl]urea (89).

89 is prepared from 88 by the procedure of Example 110 Step 4.

Step 3. 1-[2-(3,4-Dihydro-1H-isoquinolin-2-yl)ethyl]-3-[3-(2-methylquinolin-4-ylamino)phenyl]urea.

The title compound is prepared from 89 by the procedure of Example 1 Step 3.

EXAMPLE 189

{3-[5-(3,4-Dihydro-1H-isoquinolin-2-ylmethyl)-[1,3,4]oxadiazol-2-yl]phenyl}-(2-methylquinolin-4-yl)amine.

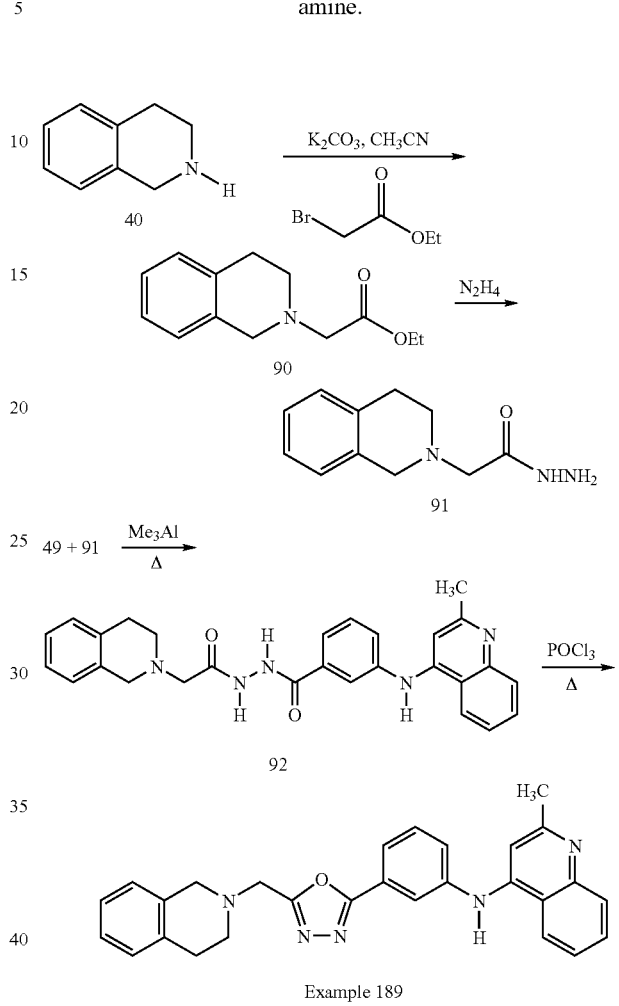

Example 189

Step 1. Ethyl (3,4-dihydro-1H-isoquinolin-2-yl)acetate (90).

To a solution of 40 (1.33 g, 10.0 mmol) in acetonitrile (50 mL) were sequentially added potassium carbonate (5.53 g, 40.0 mmol) and ethyl bromoacetate (1.67 g, 10.0 mmol). The reaction mixture was stirred at room temperature overnight, then partitioned between EtOAc (200 mL) and water (150 mL). The organic layer was dried (MgSO$_4$) and concentrated under reduced pressure to give 90 (2.1 g, 99%).

Step 2. (3,4-Dihydro-1H-isoquinolin-2-yl)acetic hydrazide (91).

A solution of 90 (2.0 g, 9.12 mmol) and hydrazine (5.1 g, 91 mmol) in ethanol (30 mL) was heated at reflux overnight. The mixture was concentrated under reduced pressure to give 91 (1.87 g ~100%) which was used without further purification.

Step 3. 3-(2-Methylquinolin-4-ylamino)-N'-(2-3,4-dihydro-1H-isoquinolin-2-yl-acetyl)benzoic hydrazide (92).

To a solution of 91 (205 mg, 1.0 mmol) in xylene (5 mL) was added trimethyl aluminum (2 M solution in hexanes, 0.75 mL, 1.5 mmol). The mixture was stirred under nitrogen for 10 minutes before the addition of methyl 3-(2-methylquinolin-4-ylamino)benzoate (49) (150 mg, 0.5 mmol).

The reaction was heated at reflux overnight, quenched with water (2 mL), basified to pH 9 (2 N NaOH), and extracted with 7:3 CH$_2$Cl$_2$/MeOH. The organic layer was dried (K$_2$CO$_3$) and concentrated under reduced pressure, and the residue was purified by flash chromatography (SiO$_2$, gradient elution) to give 92 as a pale yellow oil (147 mg, 63%).

Step 4. {3-[5-(3,4-Dihydro-1H-isoquinolin-2-ylmethyl)-[1,3,4]oxadiazol-2-yl]phenyl}-(2-methylquinolin-4-yl)amine.

A mixture of 92 (195 mg, 0.42 mmol) in phosphorous oxychloride (0.5 mL) was heated overnight before mixing cautiously with ice water (2 mL). The mixture was extracted with 7:3 CH$_2$Cl$_2$/MeOH, and the organic layer was dried (MgSO$_4$) and concentrated under reduced pressure. The residue was purified by flash chromatography (SiO$_2$, gradient elution) to give the desired product as a pale yellow solid (69 mg, 37%).

EXAMPLE 190

{3-[3-(3,4-Dihydro-1H-isoquinolin-2-yl)prop-1-ynyl]phenyl}-(2-methylquinolin-4-yl)amine.

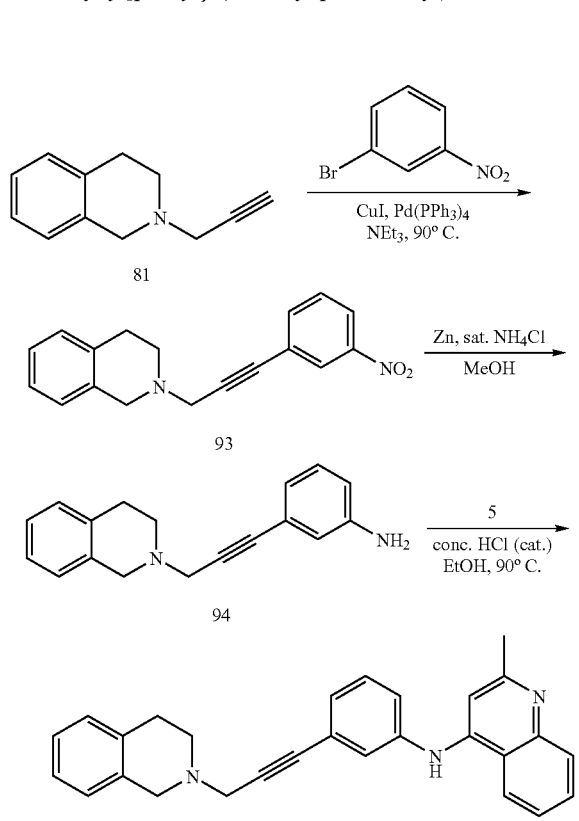

Example 190

Step 1. 2-[3-(3-Nitrophenyl)prop-2-ynyl]-1,2,3,4-tetrahydroisoquinoline (93).

To a solution of 81 (2.06 g, 10.2 mmol) in anhydrous triethylamine (30 mL) were sequentially added 1-bromo-3-nitrobenzene (1.83 g, 10.67 mmol), CuI (0.39 g, 2.05 mmol) and Pd(PPh$_3$)$_4$ (1.17 g, 1.0 mmol). The mixture was heated at 90° C. for 1 hour before it was filtered through Celite® and the filtrate was diluted with EtOAc (150 mL). The resulting solution was washed with water (100 mL), brine (100 mL), dried over Na$_2$SO$_4$ and concentrated. The residue was purified via flash silica gel chromatography to provide 93 (1.97 g, 66%).

Step 2. 3-[3-(3,4-Dihydro-1H-isoquinolin-2-yl)prop-1-ynyl]phenylamine (94).

94 was prepared from 93 by the procedure of Example 110 Step 4.

Step 3. {3-[3-(3,4-Dihydro-1H-isoquinolin-2-yl)prop-1-ynyl]phenyl}-(2-methylquinolin-4-yl)amine.

The title compound was prepared from 94 by the procedure of Example 1 Step 3.

EXAMPLE 191

N$^1$-[2-(3,4-Dihydro-1H-isoquinolin-2-yl)ethyl]-N$^7$-(2-methylquinolin-4-yl)-1,2,3,4-tetrahydronaphthalene-1,7-diamine.

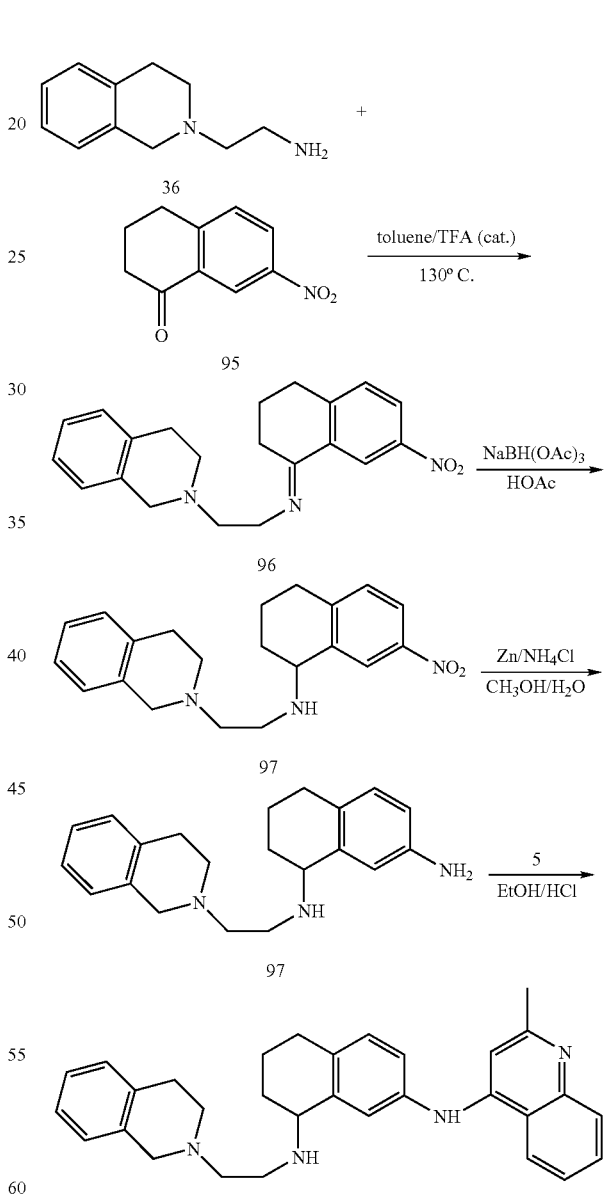

Example 191

Step 1. [2-(3,4-Dihydro-1H-isoquinolin-2-yl)ethyl]-(7-nitro-3,4-dihydro-2H-naphthalen-1-ylidene)amine (96).

To a solution of 36 (964 mg, 5.48 mmol) and 7-nitro-3,4-dihydro-2H-naphthalen-1-one (95) (1.05 g, 5.48 mmol) in toluene (30 mL) was added a catalytic amount of TFA. The reaction was heated at 130° C. overnight before it was allowed to cool to room temperature and diluted with EtOAc (100 mL). The organic solution was sequentially washed with saturated NaHCO₃ (aq. 100 mL), brine (100 mL), dried over Na₂SO₄, and concentrated to give 96 as a brown oil (1.8 g, 94%).

Step 2. [2-(3,4-Dihydro-1H-isoquinolin-2-yl)ethyl]-(7-nitro-1,2,3,4-tetrahydro-naphthalen-1-yl)amine (97).

To a solution of 96 (1.42 g, 4.07 mmol) in anhydrous dichloroethane (10 mL) were sequentially added acetic acid (267 mg, 4.48 mmol) and NaBH(OAc)₃ (1.12 g, 5.29 mmol) under N₂. The reaction was stirred at room temperature for 2 hours before it was quenched by slow addition of water (100 mL). The mixture was extracted with dichloromethane (100 mL) and the organic layer was sequentially washed with water (100 mL), saturated aq. NaHCO₃ (100 mL), and water (100 mL). The residue, from drying (Na₂SO₄) and concentrating the organic layer, was chromatographed on silica gel (EtOAc to 5:1 EtOAc/CH₃OH) to yield 97 as a brown oil (755 mg, 53%).

Step 3. $N^1$-[2-(3,4-Dihydro-1H-isoquinolin-2-yl)ethyl]-1,2,3,4-tetrahydronaphthalene-1,7-diamine (98).

98 was prepared from 97 by the procedure of Example 110 Step 4.

Step 4. $N^1$-[2-(3,4-Dihydro-1H-isoquinolin-2-yl)ethyl]-$N^7$-(2-methylquinolin-4-yl)-1,2,3,4-tetrahydronaphthalene-1,7-diamine.

The title compound was prepared from 98 by the procedure of Example 1 Step 3.

EXAMPLE 198

[2'-(3,4-Dihydro-1H-isoquinolin-2-ylmethyl)biphenyl-3-yl]-(2-methylquinolin-4-yl)amine

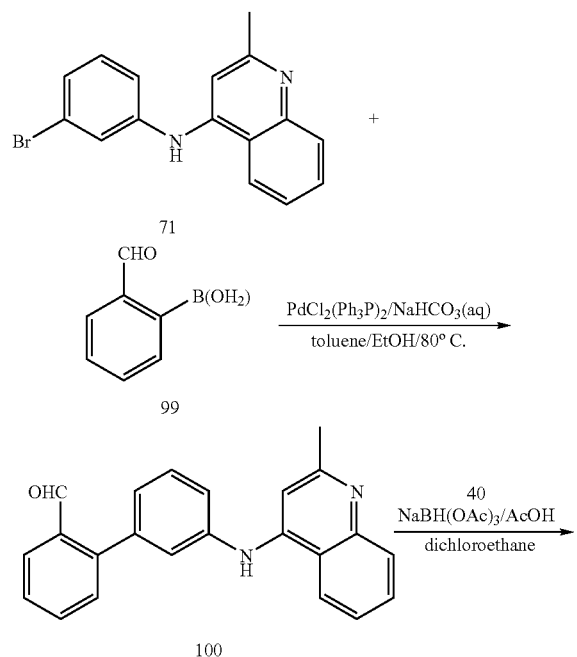

Example 198

Step 1. 3'-(2-Methylquinolin-4-ylamino)biphenyl-2-carbaldehyde (100).

To a stirred suspension of 71 (411 mg, 1.31 mmol) in toluene (12.8 mL) under N₂ were sequentially added saturated NaHCO₃ (aq. 0.5 mL), a solution of 99 (303 mg, 2.02 mmol) in EtOH (8.9 mL), and PdCl₂(Ph₃P)₃ (52 mg, 0.07 mmol). The reaction was heated at 80° C. for 41 hours before it was allowed to cool to room temperature and extracted with ethyl acetate (50 mL). The ethyl acetate extracts were washed with water (30 mL), brine (30 mL), dried (MgSO₄), and concentrated. The residue was chromatographed on silica gel (dichloromethane to 20:1 dichloromethane/methanol) to give 100 as a yellow solid (166 mg, 37.4%).

Step 2. [2'-(3,4-Dihydro-1H-isoquinolin-2-ylmethyl)biphenyl-3-yl]-(2-methylquinolin-4-yl)amine.

To a solution of 100 (166 mg, 0.49 mmol) and 40 (0.06 mL, 0.473 mmol) in dichloroethane (4.9 mL) were sequentially added NaBH(OAc)₃ (155 mg, 0.73 mmol) and HOAc (0.03 mL, 0.52 mmol). The reaction was stirred for 48 hours and then extracted with dichloromethane (2×30 mL). The dichloromethane extracts were washed with 2 N NaOH (aq. 15 mL), brine (15 mL), dried (MgSO₄), and concentrated. The residue was chromatographed on silica gel (ethyl acetate) to give desired product as a yellow solid (51 mg, 23.7%).

EXAMPLE 202

{3-[2-(4-Benzylpiperidin-1-yl)ethanesulfonyl]phenyl}-(2-methylquinolin-4-yl)amine.

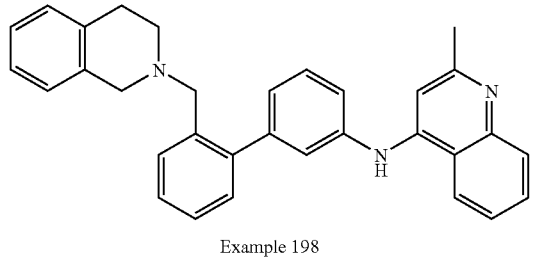

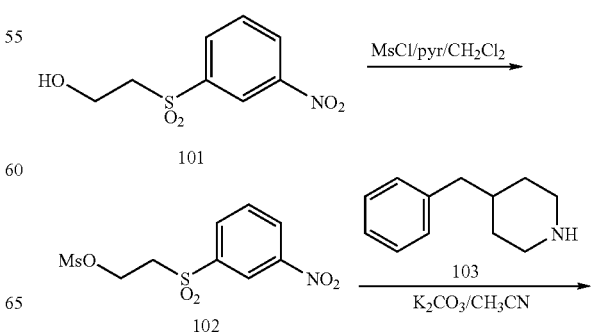

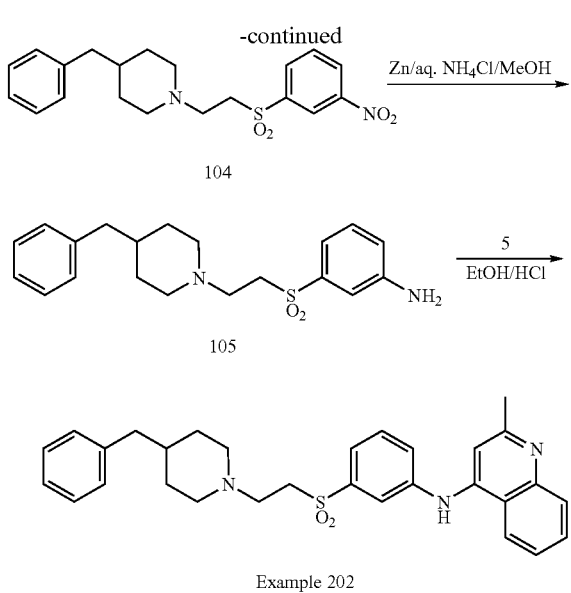

Example 202

Step 1. 2-(3-Nitro-benzenesulfonyl)ethyl methanesulfonate (102).

To a solution of 2-(3-nitrobenzenesulfonyl)ethanol (101) (5.0 g, 21.6 mmol) in dichloromethane (31.5 mL) and pyridine (7 mL) was added methanesulfonyl chloride (4.9 g, 43 mmol). The mixture was stirred at room temperature overnight before it was partitioned between dichloromethane (200 mL) and 0.5 N HCl (200 mL). The organic layer was dried over MgSO$_4$ and concentrated on a rotavap to give 102 (4.78 g, 71%).

Step 2. 4-Benzyl-1-[2-(3-nitrobenzenesulfonyl)ethyl]piperidine (104).

A mixture of 102 (1.0 g, 3.2 mmol), 4-benzylpiperidine (103) (0.62 g, 3.5 mmol), and potassium carbonate (1.1 g, 8.0 mmol) in acetonitrile (10 ml) was heated at 70° C. overnight. It was allowed to cool to room temperature and partitioned between EtOAc (150 mL) and water (150 mL). The organic layer was washed with water (100 ml), brine (100 ml), dried over MgSO$_4$, and concentrated. The residue was chromatographed on silica gel (8:1 to 4:1 to 2:1 hexanes/EtOAc) to give 104 (0.26 g, 21%).

Step 3. 3-[2-(4-Benzylpiperidin-1-yl)ethanesulfonyl]phenylamine (105).

See Example 110 Step 4.

Step 4. {3-[2-(4-Benzylpiperidin-1-yl)ethanesulfonyl]phenyl}-(2-methylquinolin-4-yl)amine.

The title compound was prepared from 105 by the procedure of Example 1 Step 3.

EXAMPLE 203

(3-{[2-(4-Benzylpiperidin-1-yl)ethylamino]methyl}phenyl)-(2-methylquinolin-4-yl)amine

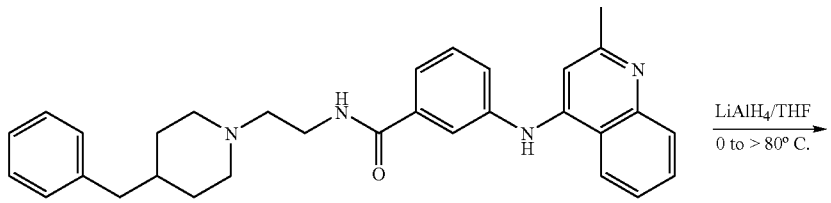

Example 134

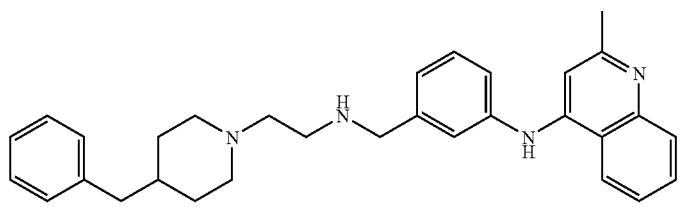

Example 203

To a solution of Example 134 (0.62 g, 1.30 mmol) in THF (20 mL) was added LiAlH$_4$ (1 M in THF, 4.0 mL, 3.90 mmol) at 0° C. The mixture was warmed to room temperature and then heated at 80° C. for 16 hours. The reaction was allowed to cool to room temperature and quenched with Na$_2$SO$_4$.10H$_2$O. The resulting slurry was filtered, rinsed with ethyl acetate, and the filtrate concentrated. The residue was chromatographed on silica gel (dichloromethane to 10:1 to 5:1 dichloromethane/methanol) to give the desired product as a yellow solid (170 mg, 28.3%).

Example 208

N-[2-(4-Benzylpiperidin-1-yl)ethyl]-N'-(2-methylquinolin-4-yl)pyrimidine-4,6-diamine.

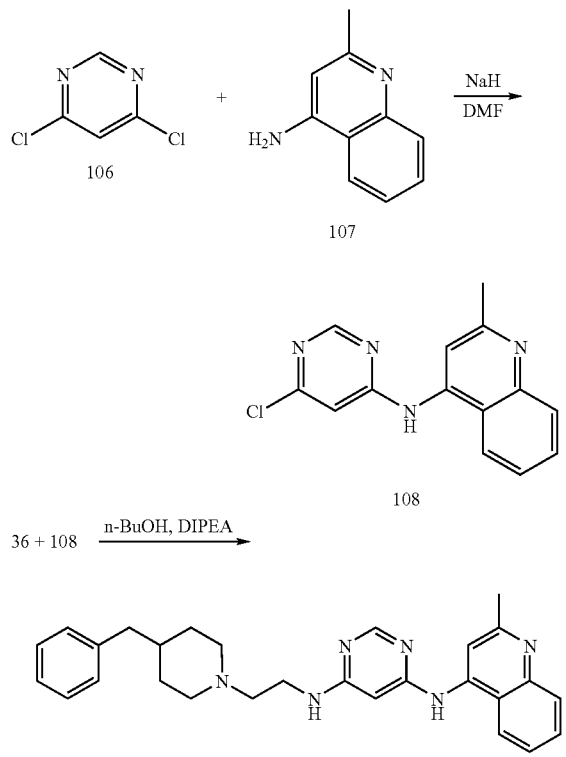

Example 208

EXAMPLE 209

3-(4-Benzylpiperidin-1-yl)-1-[3-(2-methylquinolin-4-ylamino)phenyl]propan-1-one.

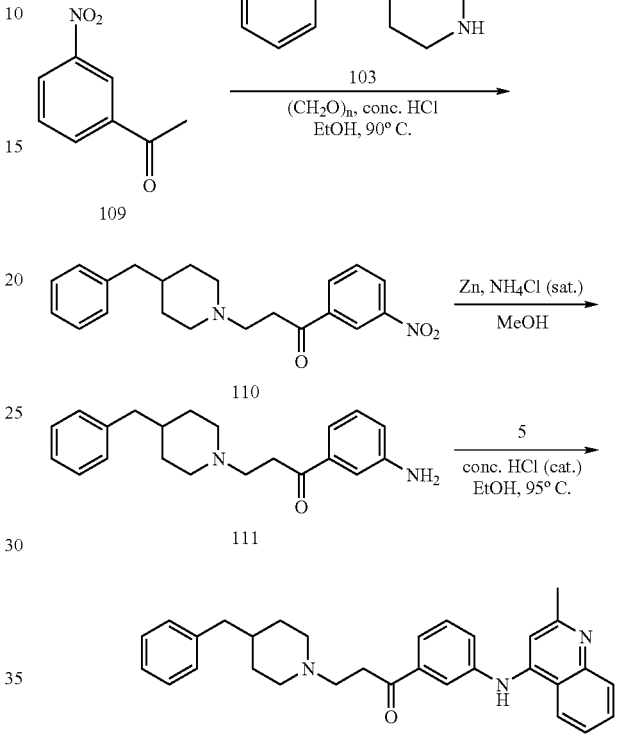

Example 209

Step 1. (6-Chloropyrimidin-4-yl)-(2-methylquinolin-4-yl)amine (108).

To a solution of 4-amino-2-methylquinoline (107) (1.0 g, 6.7 mmol) in anhydrous DMF (60 mL) was added NaH (60% in mineral oil, 0.32 g, 8.0 mmol). The mixture was stirred for 1 hour followed by the addition of 4,6-dichloropyrimidine (106) (1.0 g, 6.7 mmol). The reaction was heated at 90° C. overnight before it was poured into ice water (100 mL). The mixture was extracted with ether (3×100 mL) and the combined organic layers were dried (MgSO$_4$), concentrated under reduced pressure. The residue was purified by flash chromatrography (SiO$_2$, gradient elution, hexanes to 3:1 hexanes/ethyl acetate to 7:3 CH$_2$Cl$_2$/MeOH) to provide 108 (80 mg, 5%) as a white solid.

Step 2. N-[2-(4-Benzylpiperidin-1-yl)ethyl]-N'-(2-methylquinolin-4-yl)pyrimidine-4,6-diamine.

To a solution of diamine 36 (0.05 g, 0.21 mmol) in n-BuOH (2 mL) were sequentially added 108 (0.05 g, 0.18 mmol) and diisopropylethylamine (37 mg, 0.27 mmol). The mixture was heated at 100° C. overnight before the volatiles were removed under reduced pressure. The residue was purified by flash chromatography (SiO$_2$, gradient elution, 3:1 hexanes/ethyl acetate to 7:3 CH$_2$Cl$_2$/MeOH) to yield the desired product (20 mg, 25%) as a yellow oil.

Step 1. 3-(4-Benzylpiperidin-1-yl)-1-(3-nitrophenyl)propan-1-one (110).

To a solution of 3-nitroacetophenone (109) (0.60 g, 3.63 mmol) and 4-benzylpiperidine (103) (0.64 g, 3.63 mmol) in absolute ethanol (5 mL) was added concentrated hydrochloric acid (0.30 mL, 3.60 mmol). The mixture was heated under reflux and paraformaldehyde (0.32 g, 10.96 mmol) was added in four portions over a period of 40 minutes. The resulting mixture was heated under reflux overnight before it was allowed to cool to room temperature and diluted with EtOAc (100 mL). Following sequential washings with 1 N NaOH (2×100 mL), water (100 mL), and brine (100 mL), the organic solution was dried (Na$_2$SO$_4$) and concentrated. The residue was purified via flash silica gel chromatography to provide 110 (0.26 g, 20%) as a dark syrup.

Step 2. 1-(3-Amino-phenyl)-3-(4-benzyl-piperidin-1-yl)-propan-1-one (111).

111 was prepared from 110 by the procedure of Example 110 Step 4.

Step 3. 3-(4-Benzylpiperidin-1-yl)-1-[3-(2-methylquinolin-4-ylamino)phenyl]propan-1-one.

The title compound was prepared from 111 by the procedure of Example 1 Step 3.

EXAMPLE 210

3-(4-Benzylpiperidin-1-yl)-1-[3-(2-methylquinolin-4-ylamino)phenyl]propan-1-one O-methyloxime.

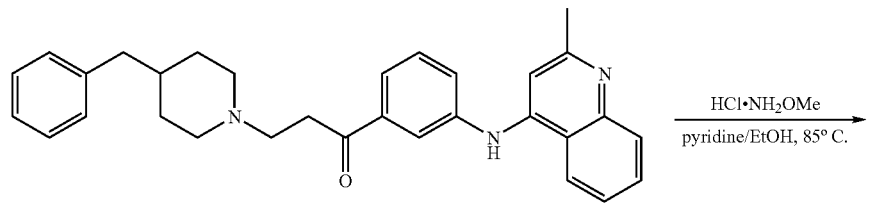

Example 209

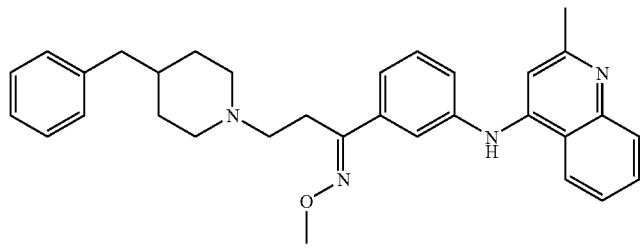

Example 210

A mixture of Example 209 (0.40 g, 0.86 mmol), ethoxyamine hydrochloric acid (0.22 g, 2.63 mmol,) and pyridine (0.19 g, 2.47 mmol) in anhydrous ethanol (3.0 mL) was heated under reflux overnight. The reaction was allowed to cool to room temperature and diluted with EtOAc (100 mL). Upon sequential washings with 1 N NaOH (2×100 mL) and brine (100 mL), the organic solution was dried over $Na_2SO_4$ and evaporated to dryness. The resulting residue was purified via flash silica gel chromatography to give the desired product (100 mg, 24%) as a white foam.

TABLE 4

| Example # | Structure | Chemical Name | Physical Description[a] | [M + H]+ |
|---|---|---|---|---|
| 174 | 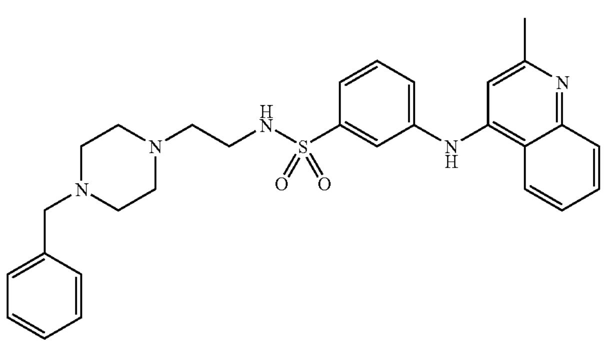 | N-[2-4-Benzylpiperazin-1-yl)ethyl]-3-(2-methylquinolin-4-yl amino)benzenesulfonamide | pale yellow solid[b] | 516.39 |

TABLE 4-continued

| Example # | Structure | Chemical Name | Physical Description[a] | [M + H]+ |
|---|---|---|---|---|
| 175 | 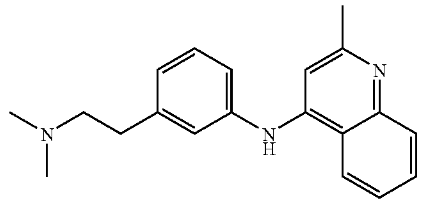 | [3-(2-Dimethylaminoethyl)phenyl]-(2-methyl quinolin-4-yl)amine | yellowish solid[b] | 306.27 |
| 176 | 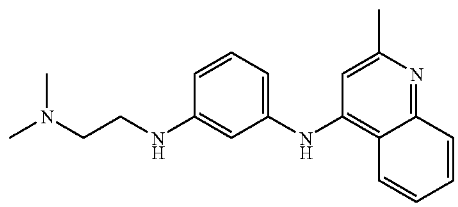 | N-(2-Dimethylaminoethyl)N'-(2-methylquinolin-4-yl)phenylene-1,3-diamine | yellow solid[b] | 321.29 |
| 177 | 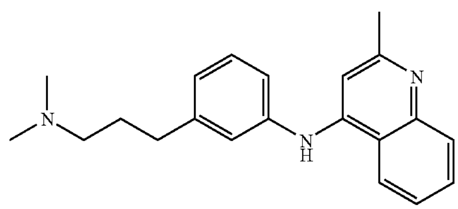 | [3-(3-Dimethylaminopropyl)phenyl]-(2-methyl quinolin-4-yl)amine | yellow solid | 320.35 |
| 178 | 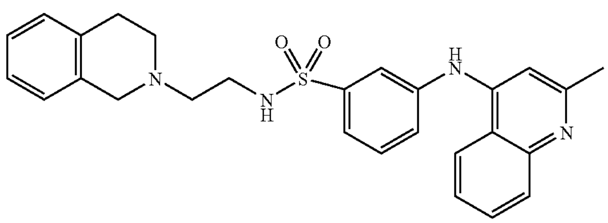 | N-[2-(3,4-Dihydro-1H-isoquinolin-2-yl)ethyl]-3-(2-methylquinolin-4-ylamino)benzenesulfonamide | yellow solid | 222.14 |
| 179 | 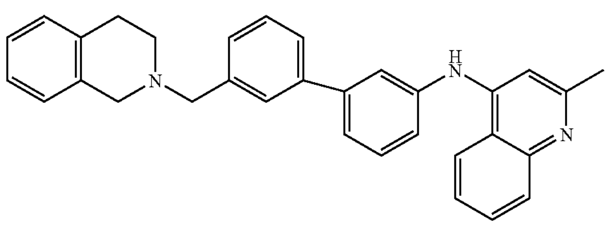 | [3'-(3,4-Dihydro-1H-isoquinolin-2-ylmethyl)biphenyl-3-yl](2-methylquinolin-4-yl)amine | yellow solid | 456.18 |
| 180 | 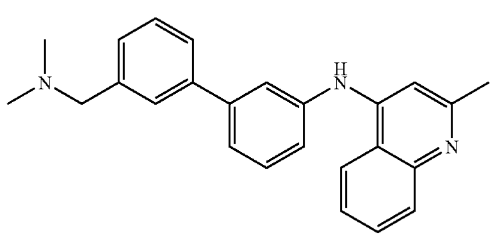 | (3'-Dimethylaminomethyl biphenyl-3-yl)-(2-methylquinolin-4-yl)amine | yellow solid[b] | 368.00 |

TABLE 4-continued

| Example # | Structure | Chemical Name | Physical Description[a] | [M + H]+ |
|---|---|---|---|---|
| 181 | 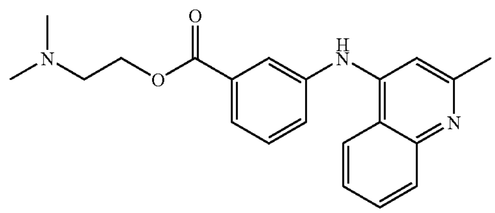 | 2-Dimethylaminoethyl 3-(2-methylquinolin-4-ylamino) benzoate | yellow solid | |
| 182 | 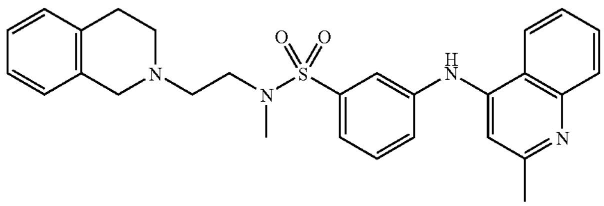 | N-[2-(3,4-Dihydro-1H-isoquinolin-2-yl)-ethyl]-N-methyl-3-(2-methyl quinolin-4-ylamino) benzenesulfonamide | yellow solid | 487.21 |
| 183 | 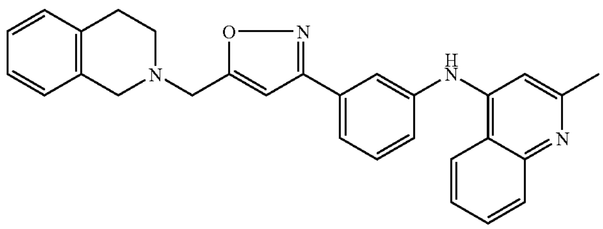 | {3-[5-(3,4-Dihydro-1H-isoquinolin-2-ylmethyl)isoxazol 3-yl]phenyl}-(2-methylquinolin-4-yl)amine | pale yellow solid[b] | 447.21 |
| 184 | 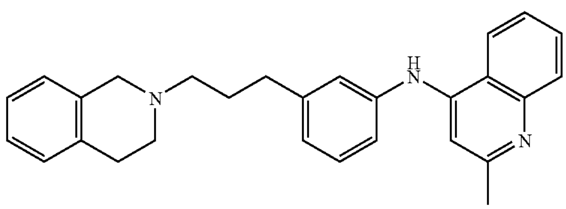 | {3-[3-(3,4-Dihydro-1H-isoquinolin-2-yl)propyl]phenyl}-(2-methyl quinolin-4-yl)amine | yellow solid | 408.29 |
| 185 | 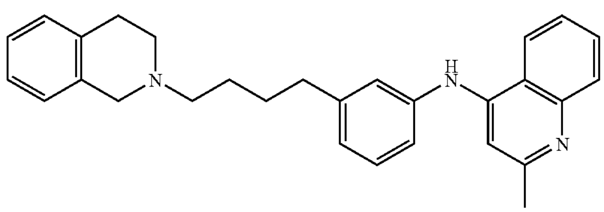 | {3-[4-(3,4-Dihydro-1H-isoquinolin-2-yl)butyl]phenyl}-(2-methyl quinolin-4-yl)amine | yellow solid | 422.30 |
| 186 | 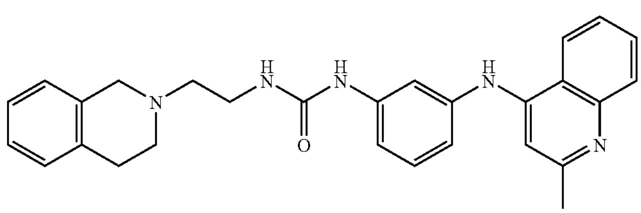 | 1-[2-(3,4-Dihydro-1H-isoquinolin-2-yl)ethyl]-3-[3-(2-methyl quinolin-4-ylamino)phenyl]urea | yellow solid | 452.08 |
| 187 | 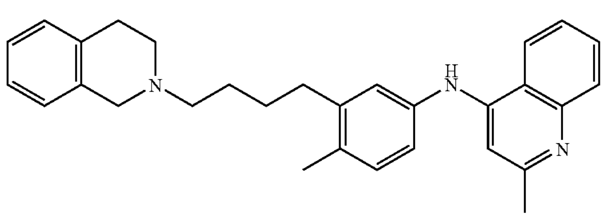 | {3-[4-(3,4-Dihydro-1H-isoquinolin-2-yl)butyl]-4-methylphenyl}-(2-methylquinolin-4-yl)amine | yellow solid | 436.31 |

| Example # | Structure | Chemical Name | Physical Description[a] | [M + H]+ |
|---|---|---|---|---|
| 188 | 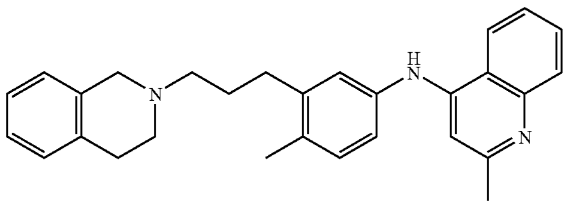 | {3-[3-(3,4-Dihydro-1H-isoquinolin-2-yl)propyl]-4-methylphenyl}-(2-methylquinolin-4yl)amine | yellow solid | 422.30 |
| 189 | 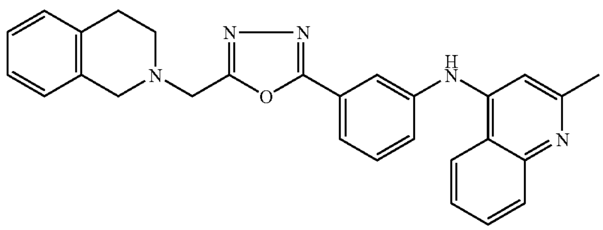 | {3-[5-(3,4-Dihydro-1H-isoquinolin-2-ylmethyl)-[1,3,4]oxadiazol-2-yl]phenyl}-(2-methylquinolin-4-yl)amine | pale yellow solid[b] | 448.20 |
| 190 | 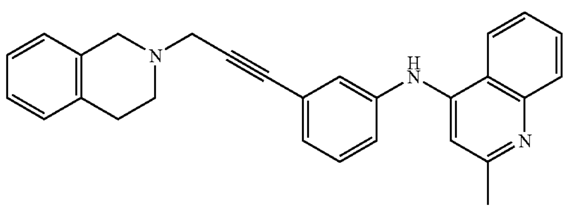 | {3-[3-(3,4-Dihydro-1H-isoquinolin-2-yl)prop-1-ynyl]phenyl}-(2-methylquinolin-4-yl)amine | off-white solid | 401.19 |
| 191 | 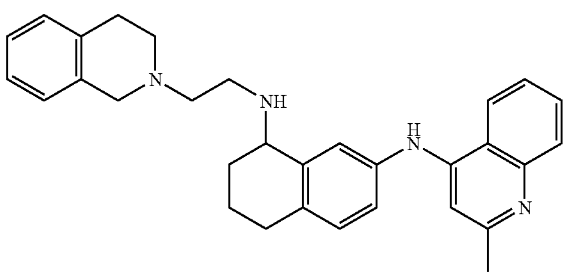 | $N^1$-[2-(3,4-Dihydro-1H-isoquinolin-2-yl)ethyl]-$N^7$-(2-methylquinolin-4-yl)-1,2,3,4-tetrahydro naphthalene-1,7-diamine | yellow solid | 463.20 |
| 192 | 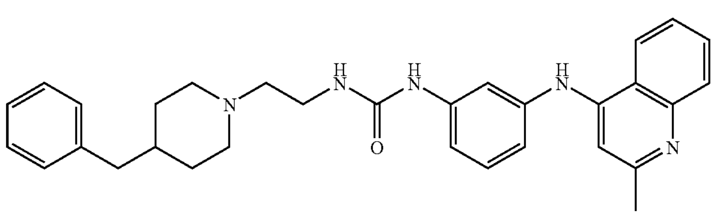 | 1-[2-(4-Benzylpiperidin-1-yl)ethyl]-3-[3-(2-methylquinolin-4-yl amino)phenyl]urea | green solid | 494.14 |
| 193 | 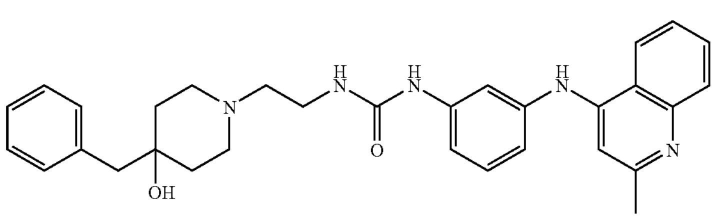 | 1-[2-(4-Benzyl-4-hydroxypiperidin-1-yl)ethyl]-3-[3-(2-methylquinolin-4-ylamino)-phenyl]urea | light brown solid | 510.18 |

TABLE 4-continued

| Example # | Structure | Chemical Name | Physical Description[a] | [M + H]+ |
|---|---|---|---|---|
| 194 | 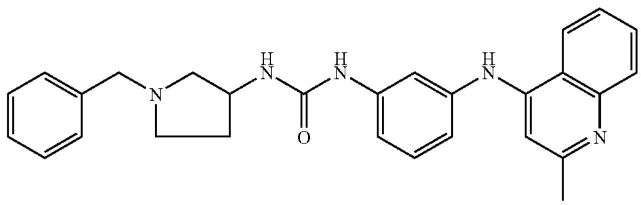 | 1-(1-Benzylpyrrolidin-3-yl)-3-[3-(2-methylquinolin-4-ylamino)phenyl]urea | pale yellow solid | 452.25 |
| 195 | 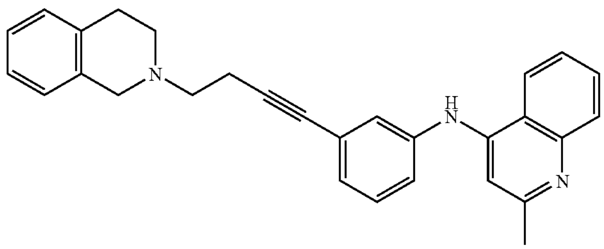 | {3-[4-(3,4-Dihydro-1H-isoquinolin-2-yl)but-1-ynyl]phenyl}-(2-methylquinolin-4-yl)amine | pale yellow solid[b] | 418.31 |
| 196 | 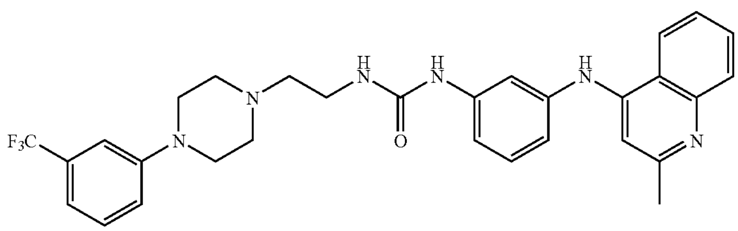 | 1-[3-(2-Methylquinolin-4-ylamino)phenyl]-3-{2-[4-(3-trifluoromethylphenyl)piperazin-1-yl]ethyl}urea | yellow solid[f] | 549.15 |
| 197 | 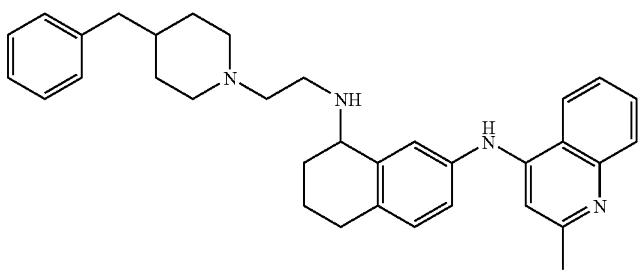 | N1-[2-(4-Benzylpiperidin-1-yl)ethyl]-N7-(2-methylquinolin-4-yl)-1,2,3,4-tetrahydronaphthalene-1,7-diamine | yellow solid[b] | 505.24 |
| 198 | 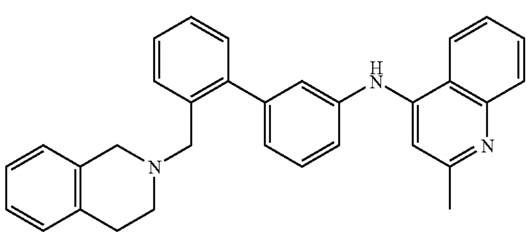 | [2'-(3,4-Dihydro-1H isoquinolin-2-ylmethyl)biphenyl-3-yl]-(2-methylquinolin-4-yl)amine | yellow solid | 456.24 |
| 199 | 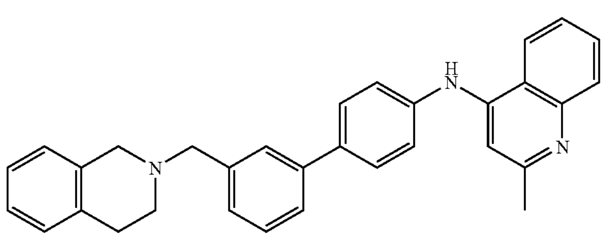 | [3'-(3,4-Dihydro-1H-isoquinolin-2-ylmethyl)biphenyl-4-yl]-(2-methylquinolin-4-yl)amine | yellow solid | 456.34 |

TABLE 4-continued

| Example # | Chemical Name | Physical Description[a] | [M + H]+ |
|---|---|---|---|
| 200 | N[1]-(2-Benzylaminoethyl)-N[7]-(2-methylquinolin-4-yl)-1,2,3,4-tetrahydro naphthalene-1,7-diamine | brownish oil[b] | 437.18 |
| 201 | (3-{[2-(3,4-Dihydro-1H-isoquinolin-2-yl)ethylamino]methyl}phenyl)-(2-methyl-quinolin-4-yl)amine | yellow solid[b] | 423.29 |
| 202 | {3-[2-(4-Benzylpiperidin-1-yl)ethanesulfonyl]-phenyl}-(2-methylquinolin-4-yl)amine | yellow solid | 500.27 |
| 203 | (3-{[2-(4-Benzylpiperidin-1-yl)ethylamino]methyl}phenyl)-(2-methylquinolin-4-yl)amine | yellow solid | 465.28 |
| 204 | [3'-(4-Benzylpiperidin-1-yl methyl)biphenyl-4-yl]-(2-methylquinolin-4-yl)amine | pale yellow solid | 498.37 |
| 205 | 4-Benzyl-1-{[3-(2-methyl quinolin-4-ylamino) phenyl]acetyl} piperidine | yellow solid[b] | 450.35 |

TABLE 4-continued

| Example # | Structure | Chemical Name | Physical Description[a] | [M + H]+ |
|---|---|---|---|---|
| 206 | 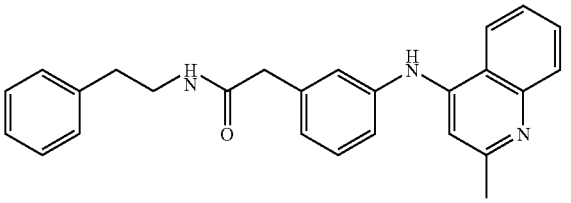 | 2-[3-2-Methylquinolin-4-yl amino)phenyl]-N-phenethyl acetamide | yellow solid[b] | 396.30 |
| 207 | 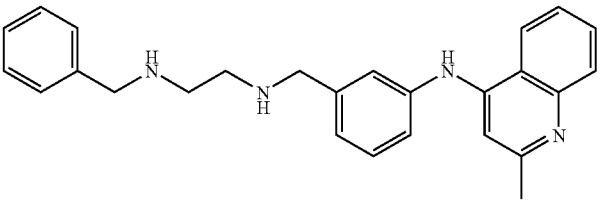 | N-Benzyl-N'-[3-(2-methyl quinolin-4-ylamino)benzyl] ethane-1,2-diamine | pale yellow solid | 397.24 |
| 208 | 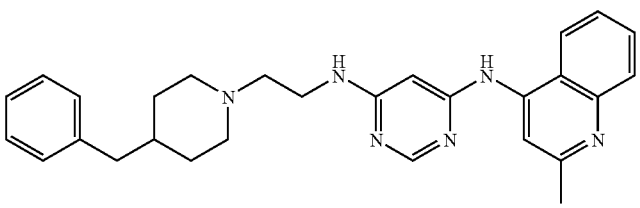 | N-[2-(4-Benzylpiperidin-1-yl) ethyl]-N'-(2-methylquinolin-4-yl)pyrimidine-4,6-diamine | off-white solid[b] | 453.29 |
| 209 | 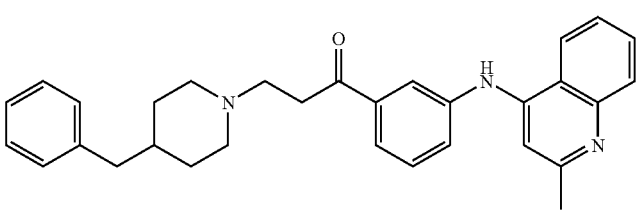 | 3-(4-Benzylpiperidin-1-yl)-1-[3-(2-methylquinolin-4-ylamino) phenyl]propan-1-one | yellow solid | 464.26 |
| 210 | 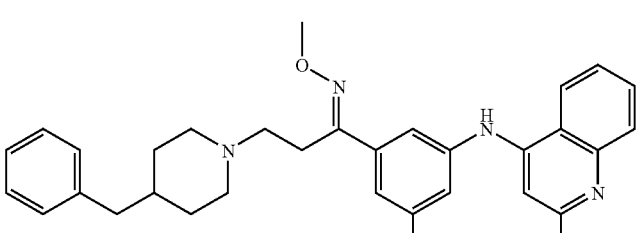 | 3-(4-Benzylpiperidin-1-yl)-1 [3-(2-methylquinolin-4-ylamino) phenyl]propan-1-one O-methyl oxime | pale yellow solid | 493.28 |
| 211 | 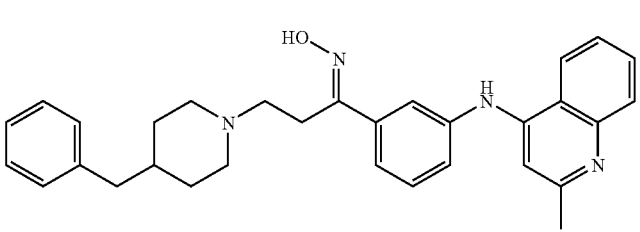 | 3-(4-Benzylpiperidin-1-yl)-1 [3-(2-methylquinolin-4-ylamino) phenyl]propan-1-one oxime | white solid | 479.28 |

[a]DiHCl salt unless otherwise noted.
[b]Parent compound
[f]TriHCl salt

The invention claimed is:
1. A compound of the formula

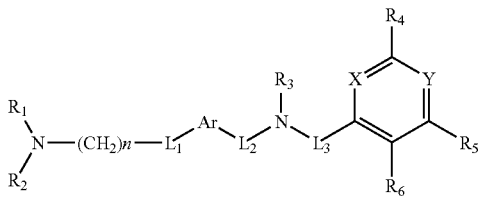

wherein Ar is selected from the group consisting of aryl, heteroaryl, benzoheteroaryl, pyridone, pyridazinone, and pyrimidone;
n is 1–6;
$R_1$ and $R_2$ along with N form a pyrrolidine, piperadine, piperazine, morpholine, benzopyrrolidine, benzopiperadine or benzopiperazine ring;
$R_3$ is H, alkyl or aralkyl;
X is C or N;
Y is N;
$R_4$ is selected from the group consisting of alkyl, aralkyl, aryl, heteroaryl, benzoheteroaryl, hydroxyl, halo, haloalkyl, alkoxy, aminocarbonyl and aminosulfonyl; or
$R_5$ and $R_6$ together form a 5–6 membered aromatic ring or a 5–7 membered aliphatic ring; $L_1$ is selected from the group consisting of, O, $NR_7$, and $SO_2$;
$L_2$ and $L_3$ are a single bond; and
$R_7$–$R_{14}$ are independently selected from the group consisting of H, alkyl, aryl and aralkyl or $R_8$ and CO and Ar can form pyridone, pyridazinone, and pyrimidone, or a pharmaceutically acceptable salt thereof.
2. A compound of claim 1 of the formula:

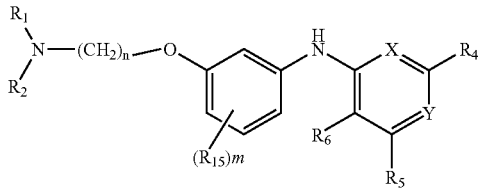

wherein each $R_{15}$ is independently H, alkyl, aralkyl, haloalkyl, aryl, heteroaryl, benzoheteroaryl, alkoxy, aminocarbonyl or aminosulfonyl and two of $R_{15}$ can form a 5–6 membered aromatic ring or a 5–7 membered aliphatic ring;
m is 0–3; and
$R_1$, $R_2$, $R_4$, $R_5$, $R_6$, n, X and Y are as defined in claim 1, or a pharmaceutically acceptable salt thereof.
3. A compound of claim 1 selected from the group consisting of:
{4-Chloro-3-[2-(3,4-dihydro-1H-isoquinolin-2-yl)ethoxy]phenyl}-(2-methylquinolin-4-yl)amine;
{3-[2-(4-Benzyl-piperidin-1-yl)ethoxy]phenyl}-(2-methylquinolin-4-yl)amine;
{4-Chloro-3-[2-(4-phenylpiperidin-1-yl)ethoxy]phenyl}-(2-methylquinolin-4-yl)amine;
{3-[2-(4-Benzylpiperazin-1-yl)ethoxy]phenyl}-(2-methylquinolin-4-yl)amine;
{3-[2-(4-Benzylpiperidin-1-yl)ethoxy]-5-trifluoromethylphenyl}-(2-methylquinolin-4-yl)amine;
{3-[3-(4-Benzylpiperidin-1-yl)propoxy]phenyl}-(2-methylquinolin-4-yl)amine;
1-(1-{2-[3-(2-Methylquinolin-4-ylamino)phenoxy]ethyl}4-phenylpiperidin-4-yl)ethanone;
(1-{2-[3-(2-Methylquinolin-4-ylamino)phenoxy]ethyl}piperidin-4-yl)diphenylmethanol;
4-Benzyl-1-{2-[3-(2-tert-butylquinolin-4-ylamino)phenoxy]ethyl}piperidin-4-ol;
4-Benzyl-1-{2-[3-(2-methylquinolin-4-ylamino)-5-trifluoromethylphenoxy]ethyl}piperidin-4-ol;
{3-[2-(4-Benzylpiperazin-1-yl)ethoxy]-5-trifluoromethylphenyl}-(2-methylquinolin-4-yl)amine;
(2-Methylquinolin-4-yl)-{3-[2-(4-phenylpiperidin-1-yl)ethoxy]-5-trifluoromethyl phenyl}amine;
{3-[2-(4-Benzylpiperidin-1-yl)ethanesulfonyl]phenyl}-(2-methylquinolin-4-yl)amine;
N-[2-(4-Benzylpiperidin-1-yl)ethyl]-N'-(2-methylquinolin-4-yl)pyrimidine-4,6-diamine; and.
4. A pharmaceutical composition comprising a compound of claim 1 and a pharmaceutically acceptable carrier or excipient.

* * * * *